United States Patent
Klaassen et al.

(10) Patent No.: US 10,772,512 B2
(45) Date of Patent: Sep. 15, 2020

(54) BLOOD PRESSURE MONITORING USING A MULTI-FUNCTION WRIST-WORN DEVICE

(71) Applicant: Apple Inc., Cupertino, CA (US)

(72) Inventors: Erno H. Klaassen, Cupertino, CA (US); Wren Nancy Dougherty, San Francisco, CA (US); Richard C. Kimoto, Cupertino, CA (US); Ravi Narasimhan, Sunnyvale, CA (US); Thomas J. Sullivan, Cupertino, CA (US); Stephen J. Waydo, Cupertino, CA (US); Todd K. Whitehurst, Cupertino, CA (US); Santiago Quijano, Cupertino, CA (US); Derek Park-Shing Young, Cupertino, CA (US); Zijing Zeng, Cupertino, CA (US)

(*) Notice: Subject to any disclaimer, the term of this patent is extended or adjusted under 35 U.S.C. 154(b) by 304 days.

(21) Appl. No.: 15/680,931

(22) Filed: Aug. 18, 2017

(65) Prior Publication Data
US 2017/0340209 A1    Nov. 30, 2017

Related U.S. Application Data

(63) Continuation of application No. 15/506,932, filed as application No. PCT/US2015/048836 on Sep. 8, 2015, now abandoned.
(Continued)

(51) Int. Cl.
*A61B 5/021* (2006.01)
*A61B 5/00* (2006.01)
(Continued)

(52) U.S. Cl.
CPC ............... *A61B 5/021* (2013.01); *A61B 5/11* (2013.01); *A61B 5/681* (2013.01); *A61B 5/6824* (2013.01);
(Continued)

(58) Field of Classification Search
CPC ..... A61B 5/02; A61B 5/02028; A61B 5/0205; A61B 5/021; A61B 5/02108;
(Continued)

(56) References Cited

U.S. PATENT DOCUMENTS

| 6,176,831 B1 | 1/2001 | Voss et al. |
| 6,228,034 B1 | 5/2001 | Voss et al. |

(Continued)

FOREIGN PATENT DOCUMENTS

| CN | 102008296 | 4/2011 |
| CN | 102499669 | 6/2012 |

(Continued)

OTHER PUBLICATIONS

"National, State, and Local Area Vaccination Coverage Among Children Aged 19-35 Months—United States, 2011", Morbidity Mortality Weekly Report Weekly, vol. 61 No. 35, Sep. 7, 2012, 24 pages.
(Continued)

*Primary Examiner* — Matthew Kremer
*Assistant Examiner* — Avery M Foley
(74) *Attorney, Agent, or Firm* — Kilpatrick Townsend & Stockton LLP

(57) ABSTRACT

The present invention provides non-invasive devices, methods, and systems for determining a pressure of blood within a cardiovascular system of a user, the cardiovascular system including a heart and the user having a wrist covered by skin. More particularly, the present invention discloses a variety of wrist-worn devices having a variety of sensors configured to non-invasively engage the skin on the wrist of the user for sensing a variety of user signals from the cardiovascular system of the user. Generally, approaches disclosed herein may passively track blood pressure values without any interaction required on the part of the user or may allow for (Continued)

on demand or point measurements of blood pressure values by having a user actively interact with the sensors of the wrist-worn device. Approaches disclosed herein further allow for absolute blood pressure values to be determined directly without the requirement for any periodic calibrations or for relative blood pressure values to be tracked so as to provide relative blood pressure indices.

7 Claims, 39 Drawing Sheets

Related U.S. Application Data

(60) Provisional application No. 62/047,452, filed on Sep. 8, 2014.

(51) Int. Cl.
*A61B 5/11* (2006.01)
*A61B 5/1455* (2006.01)
*G06F 19/00* (2018.01)

(52) U.S. Cl.
CPC .......... *A61B 5/0002* (2013.01); *A61B 5/02125* (2013.01); *A61B 5/14551* (2013.01); *G06F 19/34* (2013.01)

(58) Field of Classification Search
CPC ............ A61B 5/02116; A61B 5/02125; A61B 5/02133; A61B 5/02141; A61B 5/02154; A61B 5/02158; A61B 5/11; A61B 5/1107; A61B 5/681; A61B 5/6813; A61B 5/6824; A61B 5/0002; A61B 5/0004; A61B 5/0006; A61B 5/0015; A61B 5/0017; A61B 5/0022; A61B 5/1455; A61B 5/14551; G06F 19/34
See application file for complete search history.

(56) References Cited

U.S. PATENT DOCUMENTS

| | | | |
|---|---|---|---|
| 6,443,906 B1 | 9/2002 | Ting et al. | |
| 6,514,211 B1 | 2/2003 | Baura | |
| 6,554,774 B1 | 4/2003 | Miele | |
| 6,676,600 B1 | 1/2004 | Conero et al. | |
| 6,705,990 B1 | 3/2004 | Gallant et al. | |
| 6,730,038 B2 | 5/2004 | Gallant et al. | |
| 6,918,879 B2 | 7/2005 | Ting et al. | |
| 6,932,772 B2 | 8/2005 | Kan | |
| 6,974,419 B1 | 12/2005 | Voss et al. | |
| 7,048,691 B2 | 5/2006 | Miele et al. | |
| 7,144,372 B2 | 12/2006 | Ng et al. | |
| 7,291,112 B2 | 11/2007 | Martin et al. | |
| 7,317,409 B2 | 1/2008 | Conero | |
| 7,318,807 B2 | 1/2008 | Ng | |
| 7,361,147 B2 | 4/2008 | Ng | |
| 7,503,896 B2 | 3/2009 | Miele et al. | |
| 7,503,897 B2 | 3/2009 | Ng et al. | |
| 7,867,170 B2 | 1/2011 | Gallant et al. | |
| 7,871,381 B2 | 1/2011 | Ng et al. | |
| 7,871,382 B2 | 1/2011 | Ng | |
| 7,946,994 B2 | 5/2011 | Finburgh et al. | |
| 7,976,471 B2 | 7/2011 | Martin et al. | |
| 8,086,301 B2 | 12/2011 | Cho et al. | |
| 8,157,730 B2 | 4/2012 | Leboeuf et al. | |
| 8,204,786 B2 | 6/2012 | Leboeuf et al. | |
| D666,169 S | 8/2012 | Tucker et al. | |
| 8,251,903 B2 | 8/2012 | Leboeuf et al. | |
| 8,323,982 B2 | 12/2012 | LeBoeuf et al. | |
| 8,328,727 B2 | 12/2012 | Miele et al. | |
| 8,469,895 B2 | 6/2013 | Ting et al. | |
| 8,506,497 B2 | 8/2013 | Katayama et al. | |
| 8,512,242 B2 | 8/2013 | Leboeuf et al. | |
| 8,597,195 B2 | 12/2013 | Gallant et al. | |
| 8,647,270 B2 | 2/2014 | Leboeuf et al. | |
| 8,652,040 B2 | 2/2014 | Leboeuf et al. | |
| 8,652,409 B2 | 2/2014 | LeBoeuf et al. | |
| 8,657,753 B2 | 2/2014 | Ting et al. | |
| 8,672,854 B2 | 3/2014 | Mccombie et al. | |
| 8,700,111 B2 | 4/2014 | Leboeuf et al. | |
| 8,702,607 B2 | 4/2014 | Leboeuf et al. | |
| 8,777,862 B2 | 7/2014 | Finburgh et al. | |
| 8,788,002 B2 | 7/2014 | LeBoeuf et al. | |
| 9,408,542 B1* | 8/2016 | Kinast | A61B 5/02125 |
| 2007/0100666 A1* | 5/2007 | Stivoric | G05B 1/01 705/3 |
| 2008/0146890 A1 | 6/2008 | LeBoeuf et al. | |
| 2008/0146892 A1 | 6/2008 | Leboeuf et al. | |
| 2008/0220535 A1 | 9/2008 | LeBoeuf et al. | |
| 2009/0112071 A1 | 4/2009 | LeBoeuf et al. | |
| 2010/0298650 A1* | 11/2010 | Moon | A61B 5/0002 600/301 |
| 2011/0009718 A1 | 1/2011 | Gavish | |
| 2011/0213254 A1 | 9/2011 | Ting | |
| 2013/0059396 A1 | 3/2013 | LeBoeuf et al. | |
| 2013/0131519 A1 | 5/2013 | LeBoeuf et al. | |
| 2013/0144176 A1 | 6/2013 | Lec et al. | |
| 2013/0304112 A1 | 11/2013 | Ting et al. | |
| 2014/0031662 A1* | 1/2014 | Chou | A61B 5/6838 600/384 |
| 2014/0114147 A1 | 4/2014 | Romesburg | |
| 2014/0128690 A1 | 5/2014 | LeBoeuf | |
| 2014/0135596 A1 | 5/2014 | LeBoeuf et al. | |
| 2014/0140567 A1 | 5/2014 | LeBoeuf et al. | |
| 2014/0163393 A1 | 6/2014 | McCombie et al. | |
| 2014/0163399 A1 | 6/2014 | Gallant et al. | |
| 2014/0171755 A1 | 6/2014 | LeBoeuf et al. | |
| 2014/0171762 A1 | 6/2014 | LeBoeuf et al. | |
| 2014/0180039 A1 | 6/2014 | LeBoeuf et al. | |
| 2015/0112606 A1 | 4/2015 | He et al. | |
| 2015/0119725 A1* | 4/2015 | Martin | A61B 5/04012 600/479 |
| 2015/0164351 A1 | 6/2015 | He et al. | |
| 2015/0265214 A1* | 9/2015 | De Kok | A61B 5/6843 600/301 |
| 2016/0000379 A1* | 1/2016 | Pougatchev | A61B 5/02405 600/479 |

FOREIGN PATENT DOCUMENTS

| | | |
|---|---|---|
| CN | 102631190 | 8/2012 |
| CN | 102811659 | 12/2012 |
| WO | 2015193551 | 12/2015 |
| WO | 2016040253 | 3/2016 |

OTHER PUBLICATIONS

"Non-invasive haemodynamic monitor", BioZ® Cardio Profile, 42 pages.
"Prevention, Detection, Evaluation, and Treatment of High Blood Pressure", National High Blood Pressure Education Program, The Seventh Report of the Joint National Committee, 2004, 104 pages.
"Pulse Transit Time and Velocity Calculation", Biopac Systems, Inc., Mar. 21, 2006, 3 pages.
Allen , "Photoplethysmography and its application in clinical physiological measurement", Physiol. Meas. vol. 28, 2007, pp. R1-R39.
Ashraf et al., "Size of radial and ulnar artery in local population", J Pak Med Assoc, vol. 60, No. 10, Oct. 2010, pp. 817-819.
Baheti et al., "An ultra low power pulse oximeter sensor based on compressed sensing", Body Sensor Networks, IEEE, 2009, pp. 144-148.
Cattivelli et al., "Noninvasive Cuffless Estimation of Blood Pressure from Pulse Arrival Time and Heart Rate with Adaptive Calibration", IEEE Computer Society, 2009, pp. 114-119.
Couceiro et al., "Characterization of Surrogate Parameters for Blood Pressure Regulation in Neurally-Mediated Syncope", 2013 35th Annual International Conference of the IEEE Engineering in Medicine and Biology Society (EMBC), 2013, pp. 5381-5385.

(56) References Cited

OTHER PUBLICATIONS

Critchley, "Minimally Invasive Cardiac Output Monitoring in the Year 2012", Artery Bypass, Mar. 13, 2013, pp. 45-80.
Cybulski et al., "Impedance Cardiography", Lecture Notes in Electrical Engineering, 2011, pp. 7-37.
Czajkowski et al., "Long-term Plan for Research and Translation in Hypertension for Enhancing Public Health", National Heart, Lung, and Blood Institute, National Institutes of Health Department of Health and Human Services, Dec. 2004, 77 pages.
Da Silva, "A pervasive system for real-time blood pressure Monitoring", Feb. 13, 2013, pp. 1-23.
Douniama, "Blood Pressure Estimation based on Pulse Transit Time and Compensation of Vertical Position", 3rd Russian-Bavarian Conference on Bio-Medical Engineering, 2007, 5 pages.
Douniama et al., "Blood Pressure Tracking Capabilities of Pulse Transit Times in Different Arterial Segments: A Clinical Evaluation", Computers in Cardiology, vol. 36, 2009, pp. 201-204.
Fagard, "Exercise characteristics and the blood pressure response to dynamic physical training", Med. Sci. Sports Exerc., vol. 33, No. 6,, 2001, pp. S484-S492.
Forouzanfar et al., "Coefficient-Free Blood Pressure Estimation Based on Pulse Transit Time-Cuff Pressure Dependence", IEEE Transactions on Biomedical Engineering, vol. 60, No. 7, Jul. 2013, pp. 1814-1824.
Gesche et al., "Continuous blood pressure measurement by using the pulse transit time: comparison to a cuff-based method", Eur J Appl Physiol, May 10, 2011, 7 pages.
Gesche et al., "Continuous blood pressure measurement by using the pulse transit time: comparison to a cuff-based method", Eur J Appl Physiol, vol. 112, 2012, pp. 309-315.
Harrison et al., "Portable acoustic myography—a realistic noninvasive method for assessment of muscle activity and coordination in human subjects in most home and sports settings", Physiological Reports ISSN 2051-817X, vol. 1, Iss.2, e00029, 2013, pp. 1-9.
Harwood-Smith et al., "Assessment of pulse transit time to indicate cardiovascular changes during obstetric spinal anaesthesia", British Journal of Anaesthesia, vol. 96 (1), 2006, pp. 100-105.
Hassan et al., "Non-invasive Continuous Blood Pressure Monitoring Based on PWTT", Journal of Advanced Computer Science and Technology Research, vol. 1, 2011, pp. 63-73.
He et al., "Evaluation of the Correlation Between Blood Pressure and Pulse Transit Time", IEEE, 2013, 4 pages.
Hennig et al., "Continuous blood pressure measurement using pulse transit time", Somnologie vol. 17, Jun. 6, 2013, pp. 104-110.
Hsiu et al., "Correlation of Harmonic Components between the Blood Pressure and Photoplethysmography Waveforms Following Local-Heating Stimulation", International Journal of Bioscience, Biochemistry and Bioinformatics, vol. 2, No. 4, Jul. 2012, pp. 248-253.
Hsiu et al., "Effects of Local-Heating Stimulation on the Harmonic Structure of the Blood Pressure and Photoplethysmography Waveforms", 2nd International Conference on Biomedical Engineering and Technology IPCBEE vol. 34, 2012, pp. 1-5.
Huotari et al., "Photoplethysmography and its detailed pulse waveform analysis for arterial stiffness", Rakenteiden Mekaniikka (Journal of Structural Mechanics), vol. 44, No. 4, 2011, pp. 345-362.
Jeong et al., "Continuous Blood Pressure Monitoring using Pulse Wave Transit Time", ICCAS, 2005, 4 pages.
Jobbagy, "Blood Pressure Measurement: Assessment of a Variable Quantity", 2010, pp. 316-324.
Kado et al., "RedTacton Near-body Electric-field Communications Technology and Its Applications", NTT Technical Review, vol. 8 No. 3, 2010, pp. 1-6.
Kalsi, "Design of Arterial Blood Pressure, Heart Rate Variability, and Breathing Rate Monitoring Device", Electrical and Biomedical Engineering Design Project (4BI6), Apr. 23, 2009, 65 pages.
Kim, "Design of Infrared Sensor Based Measurement System for Continuous Blood Pressure Monitoring Device", pp. 1-12.
Kim et al., "Development of an Arterial Tonometer Sensor", 31st Annual International Conference of the IEEE EMBS, Sep. 2-6, 2009, pp. 3771-3774.
Lima et al., "Use of Peripheral Perfusion Index Derived From the Pulse Oximetry Signal as a Noninvasive Indicator of Perfusion", Crit Care Med., vol. 30(6), 2002, 10 pages.
Marcinkevics et al., "Relationship between arterial pressure and pulse wave velocity using photoplethysmography during the post-exercise recovery period", Acta Universitatis Latviensis, vol. 753, Biology,, 2009, pp. 59-68.
Marinkovic, "Reconstructing the Blood Pressure Waveform using a Wearable Photoplethysmograph Sensor and Hydrostatic Pressure Variations Measured by Accelerometers", Submitted to the Department of Mechanical Engineering in Partial Fulfillment of the Requirements for the Degrees of Master of Science in Mechanical Engineering at the Massachusetts Institute of Technology, Feb. 2007, 54 pages.
Matthys et al., "Long-term pressure monitoring with arterial applanation tonometry: a non-invasive alternative during clinical intervention ?", Technol Health Care, vol. 16, 2008, pp. 183-193.
McCarthy et al., "An examination of calibration intervals required for accurately tracking blood pressure using pulse transit time algorithms", Journal of Human Hypertension, 2013, pp. 1-7.
McCarthy, "An Investigation of Pulse Transit Time as a Non-Invasive Blood Pressure Measurement Method", Journal ofPhysics:ConferenceSeries. vol. 307, 2011, 6 pages.
McCombie et al., "Adaptive hydrostatic blood pressure calibration: Development of a wearable, autonomous pulse wave velocity blood pressure monitor", Proceedings of the 29th Annual International Conference of the IEEE EMBS, Aug. 23-26, 2007, pp. 370-373.
McCombie et al., "Motion based adaptive calibration of pulse transit time measurements to arterial blood pressure for an autonomous, wearable blood pressure monitor", Engineering in Medicine and Biology Society. 2008. EMBS 2008. 30th Annual International Conference of the IEEE. IEEE. Piscataway. NJ. USA, Aug. 20, 2008, pp. 989-992.
Meigas et al., "Continuous Blood Pressure Monitoring Using Pulse Wave Delay", 2001, 5 pages.
Nakamura et al., "Collaborative Processing of Wearable and Ambient Sensor System for Blood Pressure Monitoring", Sensors, 11, ISSN 1424-8220 www.mdpi.com/journal/sensors, 2011, pp. 6760-6770.
Norris et al., "AgeChangesinHeartRateandBloodPressureResponsestoTiltingandStandardized Exercise", Circulation, vol. VIII, Downloaded from http://circ.ahajournals.org/ at CONS CALIFORNIA DIG LIB, Aug. 26, 2013, pp. 521-526.
O'Brien, "European Society of Hypertension International Protocol revision 2010 for the validation of blood pressure measuring devices in adults", Blood Pressure Monitoring, vol. 15, 2010, pp. 23-28.
O'Brien et al., "Working Group on Blood Pressure Monitoring of the European Society of Hypertension International Protocol for validation of blood pressure measuring devices in adults", Blood Pressure Monitoring, vol. 7, 2002, pp. 3-17.
O'Brien, "The British Hypertension Society protocol for the evaluation of automated and semiautomated blood pressure measuring devices with special reference to ambulatory systems", Journal of Ambulatory Monitoring, vol. 4, No. 3,, 1991, pp. 207-228.
Payne et al., "Pulse transit time measured from the ECG: an unreliable marker of beat-to-beat blood pressure", J Appl Physiol vol. 100, Sep. 1, 2005, pp. 136-141.
Poon et al., "Using the changes in hydrostatic pressure and pulse transit time to measure arterial blood pressure", 2007 Annual International Conference of the IEEE Engineering in Medicine and Biology Society : [EMBC '07] ; Lyon, France, Aug. 22-24, 2007, pp. 2336-2337.
Proenca et al., "Is Pulse Transit Time a good indicator of Blood Pressure changes during short physical exercise in a young population? ", 32nd Annual International Conference of the IEEE EMBS, Aug. 31-Sep. 4, 20, pp. 598-601.

(56) References Cited

OTHER PUBLICATIONS

Raissuni et al., "Can We Obtain a Noninvasive and Continuous Estimation of Cardiac Output? Comparison Between Three Noninvasive Methods", Int Heart J, Nov. 2013, pp. 395-400.
Reisner et al., "Utility of the Photoplethysmogram in Circulatory Monitoring", Anesthesiology, vol. 108, 2008, pp. 950-958.
Sackl-Pietsch et al., "Continuous non-invasive arterial pressure shows high accuracy in comparison to invasive intra-arterial blood pressure measurement", pp. 1-5.
Seo, "Evaluation of cardiac output using nonuniform hybrid electrical impedance model based on forward lumped parameter and both-hands impedance measurement system", The Graduate School Yonsei University, Department of Biomedical Engineering, Feb. 2012, 146 pages.
Shaltis et al., "A Finite Element Analysis of Local Oscillometric Blood Pressure Measurements", Proceedings of the 29th Annual International Conference of the IEEE EMBS, Aug. 23-26, 2007, pp. 355-358.
Shaltis et al., "A hydrostatic pressure approach to cuffless blood pressure monitoring", Proceedings of the 26th Annual International Conference of the IEEE EMBS, Sep. 1-5, 2004, pp. 2173-2176.
Shaltis et al., "Calibration of the Photoplethysmogram to Arterial Blood Pressure: Capabilities and Limitations for Continuous Pressure Monitoring", Proceedings of the 2005 IEEE Engineering in Medicine and Biology 27th Annual Conference, Sep. 1-4, 2005, pp. 3970-3973.
Shaltis et al., "Cuffless Blood Pressure Monitoring Using Hydrostatic Pressure Changes", IEEE Transactions on Biomedical Engineering, vol. 55, No. 6,, Jun. 2008, pp. 1775-1777.
Shaltis et al., "Monitoring of Venous Oxygen Saturation Using a Novel Vibratory Oximetry Sensor", 2"d Joint Conference of the IEEE Engineering in Medicine and Biology, Society and the Biomedical Engineering Society, Oct. 23-26, 2002, pp. 1722-1723.
Shaltis et al., "Wearable, Cuff-less PPG-Based Blood Pressure Monitor with Novel Height Sensor", Proceedings of the 28th IEEE EMBS Annual International Conference, Aug. 30-Sep. 3, 2006, pp. 908-911.
Silverberg, "The unsupported arm: a cause of falsely raised blood pressure readings", British Medical Journal, Nov. 19, 1977, p. 1331.
Sinha et al., "Non-Invasive Blood Pressure Monitor: Beat to Beat", Technology Development Article, Barc Newsletter, Issue No. 328, Sep.-Oct. 2012, pp. 62-68.
Smith et al., "Pulse transit time: an appraisal of potential clinical applications", Thorax vol. 54, Available online at: http://thorax.bmj.com/content/54/5/452. full.html, Oct. 13, 2013, pp. 452-458.
Sola et al., "Continuous non-invasive blood pressure estimation", Diss. ETH. No. 20093, 2011, 196 pages.
Sola et al., "Noninvasive and Nonocclusive Blood Pressure Estimation Via a Chest Sensor", IEEE Transactions on Biomedical Engineering, vol. 60, No. 12, Dec. 2013, pp. 3505-3513.
Sola et al., "Non-invasive monitoring of central blood pressure by electrical impedance tomography: first experimental evidence", Med Biol Eng Comput, vol. 49, 2011, pp. 409-415.
Somnomedics, "Non-invasive, continuous and non-reactive blood pressure measurement using PTT", Medical Devices for Sleep Diagnostics and Therapy, 2012, pp. 1-20.
Song et al., "Estimation of Blood Pressure Using Photoplethysmography on the Wrist", Computers in Cardiology, vol. 36, 2009, pp. 741-744.
Sorvoja et al., "Noninvasive Blood Pressure Measurement Methods", Molecular and Quantum Acoustics, vol. 27, 2006, pp. 239-264.
Spulak et al., "Experiments With Blood Pressure Monitoring Using ECG and PPG", Czech Technical University in Prague, 5 pages.
Spulak et al., "Parameters for Mean Blood Pressure Estimation Based on Electrocardiography and Photoplethysmography", Czech Technical University in Prague, 4 pages.
Teja, "Calculation of Blood Pulse Transit Time from PPG", Department of Biotechnology and Medical Engineering National Institute of Technology, Rourkela 2012, 2012, 54 pages.
Theodor et al., "Implantable Acceleration Plethysmography for Blood Pressure Determination", 35th Annual International Conference of the IEEE EMBS, Jul. 3-7, 2013, pp. 4038-4041.
Thompson et al., "Arteriosclerosis, Thrombosis, and Vascular Biology", Arterioscler Thromb Vase Biol. vol. 23, American Heart Association, Available online at: http://atvb.ahajournals.org/, 2003, pp. e42-e49.
Townsend, "Oscillometry", Medical Electronics, MICHAELMAS TERM, 2001, pp. 48-54.
Van Dijk et al., "Oscillometry and applanation tonometry measurements in older individuals with elevated levels of arterial stiffness", Analytical methods and statistical analysis, Blood Pressure Monitoring vol. 18 No. 6, 2013, pp. 332-338.
Vignon-Clementel et al., "A Coupled Multidomain Method for Computational Modeling of Blood Flow", A Dissertation Submitted to the Department of Mechanical Engineering and the Committee on Graduate Studies of Stanford University in Partial Fulfillment of the Requirements for the Degree of Doctor of Philosophy, Jun. 2006, 207 pages.
Ward, "Blood Pressure Measurement", Cont Edu Anaesth Crit Care & Pain.vol. 7(4), 2007, pp. 122-126.
Wibmer et al., "Pulse transit time and blood pressure during cardiopulmonary exercise tests", Physiological Research Pre-Press Article, 2014, 26 pages.
Wikipedia, "Continuous noninvasive arterial pressure", Available online at: http://en.wikipedia.org/wiki/Continuous_noninvasive_arterial_pressure, Jul. 24, 2013, 8 pages.
Woidtke, "Pulse Transit Time and Peripheral Arterial Tonometry", 33 pages.
Wong et al., "An Evaluation of the Cuffless Blood Pressure Estimation Based on Pulse Transit Time Technique: a Half Year Study on Normotensive Subjects", Cardiovasc Eng. vol. 9, 2009, pp. 32-38.
Wong et al., "The Relationship between Pulse Transit Time and Systolic Blood Pressure on Individual Subjects after Exercises", Proceedings of the 1st Distributed Diagnosis and Home Healthcare (D2H2) Conference, Apr. 2-4, 2006, pp. 37-38.
Ye et al., "Estimation of Systolic and Diastolic Pressure using the Pulse Transit Time", World Academy of Science, Engineering and Technology 43 2010 726, 2010, pp. 726-731.
Yong, "A computational system to optimise noise rejection in photoplethysmography signals during motion or poor perfusion states", Med Biol Eng Comput vol. 44, 2006, pp. 140-145.
Yoon et al., "Non-constrained Blood Pressure Monitoring Using ECG and PPG for Personal Healthcare", J Med Syst. vol. 33, 2009, pp. 261-266.
Zhang, "Cuff-Free Blood Pressure Estimation Using Signal Processing Techniques", Thesis for the degree of Master of Science in the Division of Biomedical Engineering University of Saskatchewan http://hdl.handle.net/10388/etd-09082010-164956, Aug. 2010, 73 pages.
Zhang et al., "Pulse arrival time is not an adequate surrogate for pulse transit time as a marker of blood pressure", J Appl Physiol vol. 111, 2011, pp. 1681-1686.

\* cited by examiner

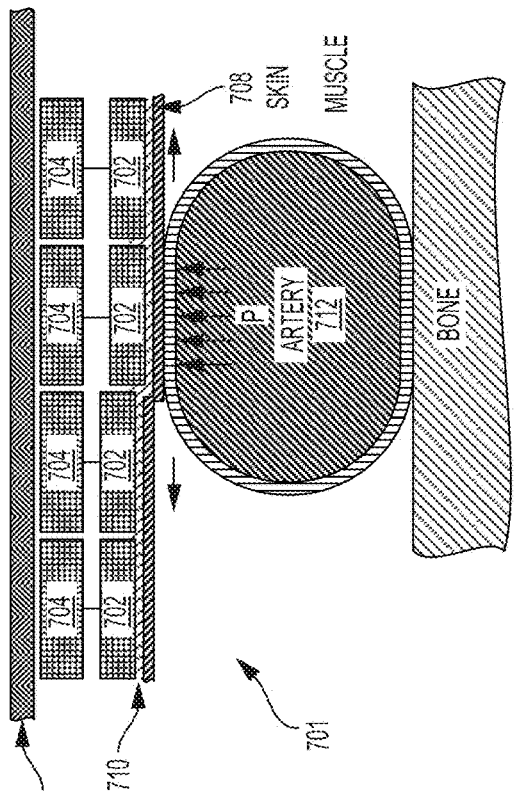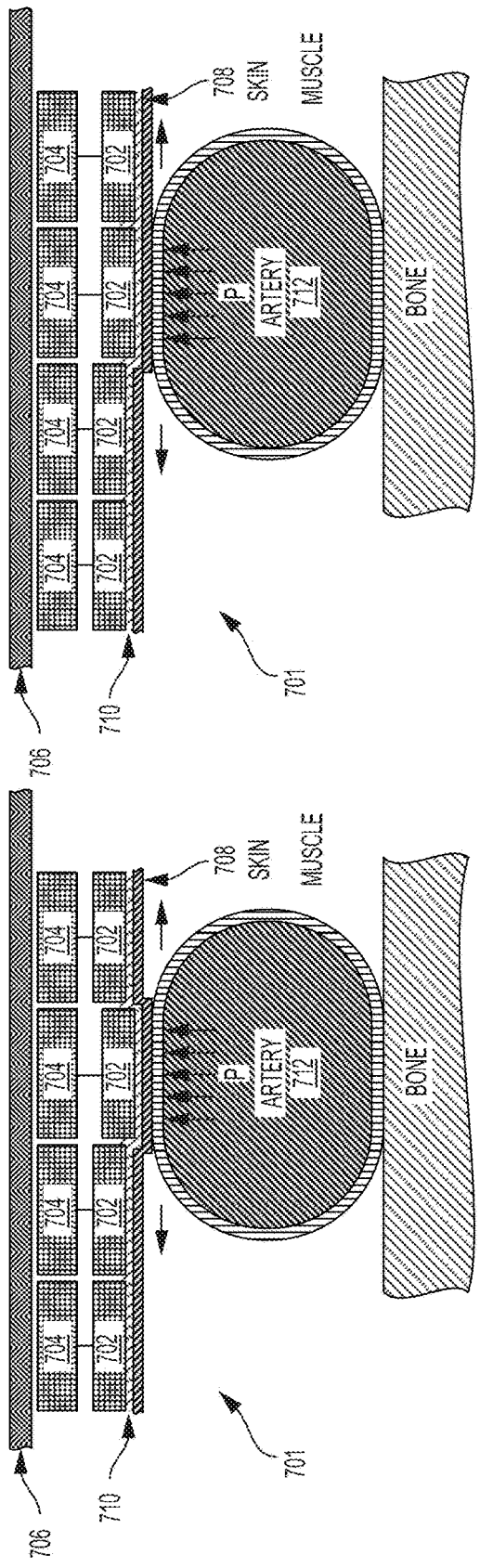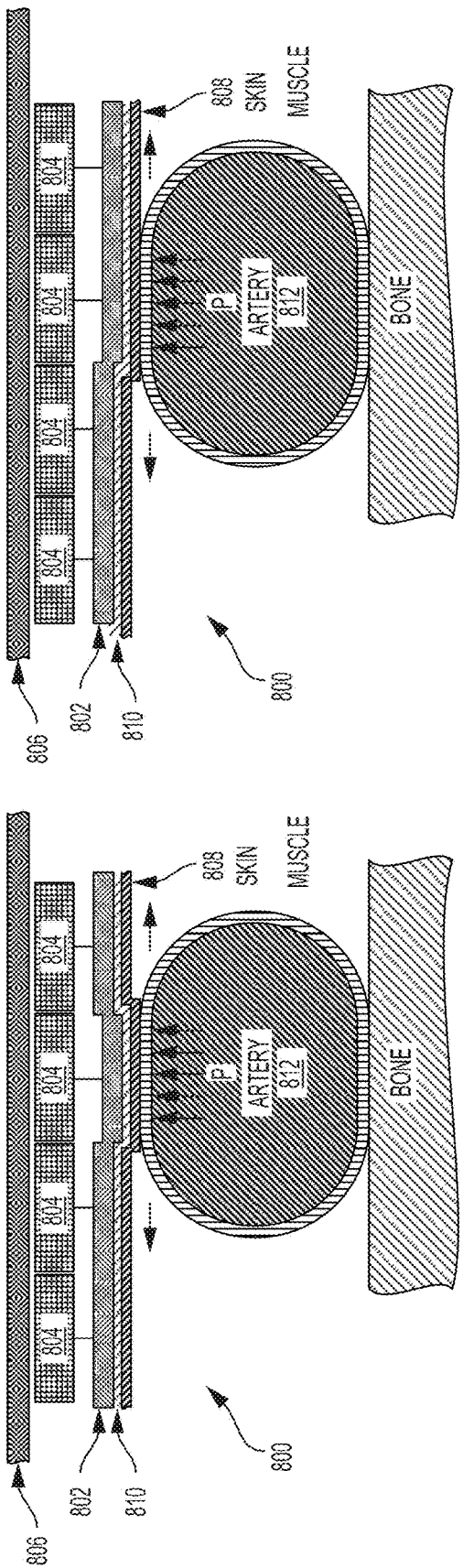
Fig. 42  Fig. 43  Fig. 44  Fig. 45

BLOOD PRESSURE MONITORING USING A MULTI-FUNCTION WRIST-WORN DEVICE

CROSS-REFERENCES TO RELATED APPLICATIONS

The present application is a Continuation of U.S. application Ser. No. 15/506,932 filed Feb. 27, 2017 which is a U.S. National Stage 35 USC 371 Application of PCT/US2015/048836 filed Sep. 8, 2015 which claims the benefit of U.S. Provisional Application Ser. No. 62/047,452 filed Sep. 8, 2014, the full disclosures of which are incorporated herein by reference in their entirety for all purposes.

The present application is related to U.S. Provisional Appln. Nos. 62/047,431 entitled "Systems, Devices, and Methods for Measuring Blood Pressure of a User;" 62/047,472 entitled "Wrist Worn Accelerometer For Pulse Transit Time (PTT) Measurements of Blood Pressure;" and 62/047,486 entitled "Electrical Coupling of Pulse Transit Time (PTT) Measurement System to Heart for Blood Pressure Measurement;" all of which were filed on Sep. 8, 2014, and are incorporated herein by reference in their entirety for all purposes.

BACKGROUND OF THE INVENTION

Elevated blood pressure (a.k.a. hypertension) is a major risk factor for cardiovascular disease. As a result, blood pressure measurement is a routine task in many medical examinations. Timely detection of hypertension can help inhibit related cardiovascular damage via accomplishment of effective efforts in treating and/or controlling the subject's hypertension.

A person's blood pressure is a continuously changing vital parameter. As a result, sporadic office blood pressure measurements may be insufficient to detect some forms of hypertension. For example, hypertension can occur in a pattern that evades detection via isolated office blood pressure measurement. Common hypertension patterns include white coat hypertension (elevated only during a limited period of time), borderline hypertension (fluctuating above and below definitional levels over time), nocturnal hypertension (elevated only during sleeping hours or not showing the normal drop in pressure during sleep), isolated systolic hypertension (elevated systolic pressure with non-elevated diastolic pressure), and isolated diastolic hypertension (elevated diastolic pressure with non-elevated systolic pressure). To detect such hypertension patterns, it may be necessary to perform additional blood pressure measurements over time to obtain a more complete view of a person's blood pressure characteristics. Although continuous measurement of blood pressure can be achieved by invasive means, for example, via an intra-arterial pressure sensing catheter, noninvasive blood pressure measurement approaches are more typically used.

Current noninvasive blood pressure measurement approaches include ambulatory and home blood pressure measurement strategies. These strategies provide such a more complete view of a person's blood pressure characteristics and are often employed in recommended situations. Ambulatory blood pressure measurement is performed while the person performs daily life activities. Currently, ambulatory blood pressure measurements are typically performed every 20 to 30 minutes using brachial oscillometric blood pressure measurement cuffs. Ambulatory blood pressure measurement may be recommended where there is large variability in office blood pressure measurements, where a high office blood pressure measurement is made in a person with otherwise low cardiovascular risk, when office and home blood pressure measurements vary, where resistance to drug treatment of blood pressure is noted or suspected, where hypotensive episodes are suspected, or where pre-clampsia is suspected in pregnant women. Home blood pressure measurements include isolated self-measurements performed by a person at home. Home blood pressure measurements may be recommended where information is desired regarding the effectiveness of blood pressure lowering medication over one or more dose-to-dose intervals and/or where doubt exists as to the reliability of ambulatory blood pressure measurement.

Current ambulatory and home blood pressure measurement approaches, however, fail to provide continuous measurement of blood pressure. Thus, convenient and effective approaches for noninvasive continuous measurement of blood pressure remain of interest.

BRIEF SUMMARY OF THE INVENTION

The present invention provides non-invasive devices, methods, and systems for determining a pressure of blood within a cardiovascular system of a user, the cardiovascular system including a heart and the user having a wrist covered by skin. More particularly, the present invention discloses a variety of wrist-worn devices having a variety of sensors configured to non-invasively engage the skin on the wrist of the user for sensing a variety of user signals from the cardiovascular system of the user. Generally, approaches disclosed herein may passively track blood pressure values without any interaction required on the part of the user, which is of particular benefit during overnight monitoring when the user is asleep or for other periods of extended monitoring. Passive tracking is particularly ideal as blood pressure values may be obtained consistently, frequently, and/or continuously over a period of time for potentially longer and more accurate and complete data sets as this approach is not dependent on user compliance and eliminates any artifacts (e.g., artificially elevated blood pressure value) associated with the act of taking the actual blood pressure measurement (e.g., white coat syndrome). Alternatively, approaches may allow for on demand or point measurements of blood pressure values by having a user actively interact with the sensors of the wrist-worn device to initiate the blood pressure measurements. For example, the user may engage sensors of the wrist-worn device with another part of their body (e.g., arm, fingers, sternum, ear) or the user may need to engage the arm on which the wrist device is worn (e.g., volume or pressure oscillometry).

Approaches disclosed herein further allow for absolute blood pressure values to be determined directly without the requirement for any periodic calibrations (e.g., applanation tonometry as described in greater detail below) or for relative blood pressure values to be tracked so as to provide relative blood pressure indices. The relative blood pressure values may be calibrated with a reference measurement to determine blood pressure values on an absolute scale. However, relative blood pressure values, even if not calibrated to provide absolute blood pressure values, can be of clinical benefit to the user or the health care professional. For example, providing a blood pressure index can show variations or patterns over time (e.g., trending data) which may be of particular diagnostic or therapeutic value for the user or health care professional. Still further, the present invention provides wrist-worn devices that are portable and compact in design and can be easily and comfortably worn for extended of periods of time. In particular, the wrist-worn devices of the present invention provide accurate and robust blood pressure monitoring and tracking outside the conventional hospital setting, which in turn reduces health care costs and empowers users and their caregivers and/or health care professionals to make more informed decisions.

Methods utilizing hydrostatic pressure changes to determine a mean or absolute blood pressure, and more specifically employing modified volume or pressure oscillometry techniques, are disclosed. In particular, such methodologies advantageously utilize the pressure changes associated with the natural vertical movement of the user's arm (e.g., actively raising and lowering their fully extended arm) not as a source of error, but instead to non-invasively measure a mean blood pressure. Methods of the present invention for determining a pressure of blood within a cardiovascular system of a user may comprise receiving a plurality of user signals from the cardiovascular system of the user with a sensor. The sensor non-invasively engages the skin of the user over the wrist of the user, each of the user signals being received by the sensor while the sensor has an associated height relative to the heart of the user. The user moves the wrist between the signals so that the heights of the sensor differ within a range of heights relative to the heart of the user. The different heights are maintained for a sufficient length of time for the device to measure blood pressure at each height. For example, the user may slowly raise their arm from a starting position below the heart to and end position above their head or vice versa, wherein the range of heights relative to the heart of the user may comprises a range from about 1 cm to about 40 cm resulting in a hydrostatic pressure differential in range from just below 1 mmHg to about 31 mmHg. A signal variation amplitude of the plurality of signals associated with the range of heights is identified and a standard pressure of the blood of the user based on the signal variation amplitude and the plurality of signals is determined, the standard pressure having an associated standard blood pressure measurement height relative to the heart.

The plurality of user signals may comprise volume or pressure waveform signals from at least one photoplethysmogram (PPG) or pressure sensor (e.g., pressure sweep for applanation tonometry approaches disclosed in greater below) respectively non-invasively engaging the skin of the user over the wrist. In this example, the signal variation amplitude may be identified from a maximum volume or pressure waveform signal based on an oscillation or amplitude of the plurality of volume or pressure waveform signals of the user. In particular, the volume or pressure waveform signal associated with the highest oscillation or amplitude comprises the maximum volume or pressure waveform signal.

A signal indicative of the height of the sensor relative to the heart associated with the maximum volume or pressure waveform signal may be received and/or calculated from at least a height sensor, accelerometer, and/or a barometric pressure sensor coupled to the wrist-worn device. Still further, user input (e.g., length of arm, height from heart to shoulder, etc.), or other anthropometric data may also be utilized in combination with the height sensor, accelerometer, and/or a barometric pressure sensor signals to determine a height measurement associated with the highest oscillation or amplitude. Ideally, the height measurement provides accuracy of ±6 cm for ensuring pressure errors of less than 3-5 mmHg. The standard or mean arterial pressure may be determined based on the maximum volume or pressure waveform signal and the signal indicative of the height of the sensor relative to the heart associated with the maximum volume or pressure waveform signal (e.g., hydrostatic pressure component).

The mean arterial pressure may be generally correlated to the hydrostatic pressure component determined above plus a relatively constant, low pressure applied externally to a radial artery beneath the skin of the wrist of the user as the user raises or lowers their arm though the range of heights relative to the heart. This relatively constant pressure may be applied over the radial artery by an actuator coupled to the wrist-worn device or by user actuation, such as snugly tightening the band of the device around their wrist. This constant pressure range should be within the range of known or expected mean arterial pressure, so that as the local pressure changes with changes in the arm height, the applied pressure becomes equal to the temporary local pressure at some height of the arm relative to the heart. A pressure sensor or an array thereof may be coupled to the wrist-worn device and non-invasively engaging the skin of the wrist to measure the pressure applied to the wrist as the at least one PPG or pressure sensor is swept through the range of heights relative to the heart of the user for determining the mean arterial pressure. The mean arterial pressure point measurement may further be utilized as a reference blood pressure measurement for calibrating relative blood pressure signals, as described in greater detail below. Still further, the determined mean arterial pressure may be transmitted to a second wrist-worn device (e.g., watch), mobile device, tablet, computer, or database for further processing (e.g., calibration of relative blood pressure signals absolute blood pressure tracking), storage (e.g., electronic medical record), retrieval by other devices or programs (e.g., health software application), and/or display to the user or their health care professional.

As described above, relative blood pressure values may be calibrated with a reference measurement to determine blood pressure values on an absolute scale. Methods of the present invention for obtaining a blood pressure measurement of a user comprise sensing, with a first sensor of a wrist-worn device non-invasively engaging the skin on the wrist of the user, a first user signal indicative of ventricular ejection of blood (or when a pressure pulse begins propagation) from the heart of the user, the first sensed ventricular ejection signal having an associated ventricular ejection time. The method may further comprise sensing, with a second sensor of the wrist-worn device non-invasively engaging the skin on the wrist of the user, a second user signal indicative of arrival of a pressure pulse in the wrist, the second sensed pressure pulse signal associated with the first sensed ventricular ejection signal and having an associated pulse arrival time. A relative blood pressure value may be determined in response to a first pulse transit time (PTT) identified from a difference between the ventricular ejection time and the pulse arrival time. An absolute reference blood pressure measurement obtained in coordination with the relative blood pressure may be received from an accurate reference measurement device and the absolute blood pressure of the relative blood pressure value determined in response to a difference between the relative blood pressure and the absolute reference blood pressure.

A plurality of relative blood pressure values determined prior to or subsequent the first PTT may further be calibrated based on the difference between the relative blood pressure associated with the first PTT and the absolute reference blood pressure (e.g., backward or retroactive calibration of existing data or forward calibration of new data). For example, a second PTT may be determined using the first and second sensors of the wrist-worn device, and the absolute blood pressure of the second PTT determined in response to the difference between the relative blood pressure and the absolute reference blood pressure. In another example, an absolute blood pressure of a second PTT determined from the first and second sensors of the wrist-worn device and prior to the first PTT is determined in response to the difference between the relative blood pressure and the absolute reference blood pressure. It will be appreciated that the plurality of relative blood pressure values may further be adjusted based on a variety of other factors, such as anthropometric information, vasomotor effects, hydrostatic effects, ambient temperature, user actively level, skin perfusion, skin temperature, or body posture.

Ideally, the plurality of relative blood pressure values are measured when the user is relatively stationary for a short period of time, for example 30 seconds or less, 20 seconds or less, or 10 seconds or less. Further, in some instances, the plurality of relative blood pressure values are preferably measured at a substantially constant sensor height relative to the heart of the user to minimize errors due to hydrostatic pressure effects, as discussed in greater below. The absolute reference blood pressure measurement may be obtained from a variety of sources including volume oscillometry (as described herein), applanation tonometry devices (as described herein), an oscillometric cuff, or an input by the user. In some instances, if the difference between the determined absolute blood pressure and the reference blood pressure is greater than ±5 mmHg mean error or ±8 mmHg sigma error, a second absolute reference blood pressure measurement may be required for accurate calibration of the relative pressure values. In this instance, a blood pressure index of the relative blood pressure values may be displayed or transmitted instead of the absolute blood pressure values.

Generally, user-dependent calibration of the relative blood pressure values may be periodically carried out at least once a week, monthly, or yearly, wherein active measurement approaches may require more frequent recalibration intervals than passive measurement approaches. Methods of the present invention further include recalibration, wherein the absolute reference blood pressure measurement is obtained at a first time period and a second absolute reference blood pressure measurement is obtained in coordination with a second relative blood pressure at a second time period later than the first time period (e.g., 1 month later). An absolute blood pressure of the second relative blood pressure value may then be determined in response to a difference between the second relative blood pressure and the second absolute reference blood pressure.

Calibration may be carried out locally by a controller coupled to the wrist-worn device or externally of the wrist-worn device by a mobile device, tablet, computer, or database. Further, the plurality of calibrated relative blood pressure values may be transmitted to a second wrist-worn device, mobile device, tablet, computer, or database for further processing, storage, retrieval, or display as described herein. The wrist-worn device of the present invention may comprise an active band, watch, and/or heart rate monitor. For example, the device may comprise a single integral electronic watch device that includes both a heart rate monitor and blood pressure monitor. Still further, the blood pressure monitor may be incorporated into a separate active band that is connectable to the watch device as described in greater detail below.

The first sensor may comprise at least one impedance cardiogram (ICG), electrocardiogram (ECG/EKG), ballistocardiogram (BCG), phonocardiogram (PCG), or seismocardiogram (SCG) sensor coupled to the wrist-worn device for sensing the first user signal indicative of ventricular ejection of blood from the heart of the user. For example, the at least one ICG or ECG sensor comprise at least a first pair of dry electrodes non-invasively engaging glabrous skin on an anterior surface of the wrist of the user and a second pair of dry electrodes contacted by at least two separate fingers (or a thumb, palm, or wrist) of a hand opposite a hand on which the device is worn to provide cross-body dynamic impedance or electrical potential measurements respectively. In another example, the at least one ICG or ECG sensor comprise at least a first pair of dry electrodes non-invasively engaging glabrous skin on an anterior surface of the wrist of the user and a second pair of dry electrodes, wherein the second pair of dry electrodes and/or wrist-worn device non-invasively engage a skin surface of a sternum of the user. In addition or alternatively, the least one BCG sensor comprises an accelerometer non-invasively engaging an anterior surface of the wrist so as to passively measure a relative blood pressure. It will be appreciated that engagement with a glabrous skin surface provides improved electrical contact, but the sensors described herein can also engage the posterior surface of the wrist for measurements. Still further, the at least one PCG sensor comprises a sound sensor and the sound sensor, wrist-worn device and/or hand of the wrist-worn device non-invasively engage a skin surface of a sternum of the user. Optionally, the at least one SCG sensor comprises an accelerometer and the accelerometer, wrist-worn device and/or hand of the wrist-worn device non-invasively engage the sternum.

The second sensor may comprise at least one PPG sensor or pressure sensor coupled to the wrist-worn device for sensing the second user signal indicative of arrival of the pressure pulse in the wrist. The at least one PPG sensor may comprise at least one infra-red, red, or green optical source and a detector positioned over a radial artery of the wrist (or the finger or arm) of the user. The pressure sensor may comprise at least one pressure transducer, accelerometer, or strain gauge configured to be positioned over a radial artery of the wrist of the user.

It will be appreciated that multiple combinations of sensors may be utilized on the wrist-worn device for measuring the first and/or second user signals. For example, the first sensor may comprise first and second cardiogram sensors coupled to the wrist-worn device for sensing the first user signal indicative of ventricular ejection of blood from the heart of the user, wherein the second cardiogram sensor is different than the first cardiogram sensor. In this example, the first cardiogram may comprise an ICG sensor for a cross body measurement and the second cardiogram sensor may comprise a BCG sensor for comparison to a passive measurement or a SCG/PCG sensor for comparison to an active measurement that has little or no error due to hydrostatic pressure changes as the SCG/PCG measurement is made at the chest which is relatively aligned with a height of the heart.

It will be appreciated that multiple combinations of sensors may be utilized on both the wrist-worn device and separate non-wrist worn devices (e.g., mobile device, tablet, stand-alone or attached accessory) for measuring the first and/or second user signals. In another example, an accelerometer of a mobile device may be utilized to provide a SCG measurement of the first user signal indicative of ventricular ejection of blood from the heart of the user by having the mobile device held or strapped against the chest or placed in the user's shirt pocket while the PPG sensor of the wrist-worn device measures the second user signal indicative of arrival of the pressure pulse in the wrist. Still further, non-wrist worn devices may be utilized to provide ECG/ICG measurements nominally across the heart, a pressure pulse over the radial artery (or a carotid or femoral artery), or a PPG measurement over a finger, thumb, neck, thigh, forehead, or earlobe. For multi-device implementations of wrist-worn and non-wrist worn devices, time synchronization between devices may be carried out via a wireless or telemetry interface (e.g., Bluetooth or WiFi) or by conducting a signal through the user's body (e.g., small electrical pulse) as a reference strobe.

The present invention further includes a first wrist-worn device for determining a pressure of blood within a cardiovascular system of a user. The device may comprise an elongate band non-invasively engaging the skin on the wrist of the user, wherein the elongate band is releasably coupleable to a second wrist-worn electronic device. At least one PTT or pressure sensor may be coupled to the elongate band, the sensor non-invasively engaging the skin over the wrist of the user for measuring user signals from the cardiovascular system of the user. A controller may be coupled to the elongate band and at least one PTT or pressure sensor for determining relative or absolute blood pressure signals based on the user signals. A power source may be coupled to the elongate band and the controller or the at least one PTT or pressure sensor for providing power to the wrist-worn device. A telemetry/wireless interface (e.g., Bluetooth or WiFi) may be coupled to the elongate band and the controller.

The second wrist-worn electronic device may comprise a watch or heart rate monitor having a housing encasing a second controller, second power source, and second telemetry interface that are distinct and separate from the first wrist-worn blood pressure monitoring band. Advantageously, providing bands that are releasably coupleable to the second wrist-worn device (e.g., watch) provides for user customization of the watch based on the desired sensor monitoring. For example, a first band may comprise an ICG/PPG sensor combination for measuring relative blood pressure values while a second band may comprise a pressure sensor/actuator combination for measuring absolute blood pressure values. Still further, a third band may monitor an entirely different diagnostic than blood pressure (e.g., heart rate monitor). The user may selectively choose between the first, second, or third bands for the desired sensor monitoring and may further interchange the bands at any time period as desired (e.g., a fourth band comprising a passive BCG/PPG sensor combination for night time blood pressure monitoring and a fifth band comprising an active ECG/PPG sensor combination for day time blood pressure monitoring) via a releasable coupling feature. Still further, the first wrist-worn device may easily communicate (e.g., transmit blood pressure values, receive updated instructions, such as new calibration equations, etc.) with the second wrist-worn device via WiFi or Bluetooth. The elongate band further comprises at least one releasable connection or coupling feature for securing the selected band to the watch or heart rate monitor. For example, the connection or coupling feature may be mechanical (pin/peg connection, clasp, snap fit, set-screw, or slide-in connector) or magnetic. It will be appreciated still further that some embodiments of the present invention may utilize the same controller, power source, or telemetry interface for both the first and second wrist-worn devices. Still further, the first and second wrist-worn devices (e.g., blood pressure monitor and hear rate monitor) may be incorporated into a single integral electronic watch device.

As described above, the least one PTT sensor may comprise a first and second sensors. The first sensor is configured to measure a first user signal indicative of ventricular ejection of blood from the heart of the user, the first sensed ventricular ejection signal having an associated ventricular ejection time. The second sensor is configured to measure a second user signal indicative of arrival of a pressure pulse in the wrist, the second sensed pressure pulse signal associated with the first sensed ventricular ejection and having an associated pulse arrival time, wherein the relative blood pressure signal is determined from a difference between the ventricular ejection time and the pulse arrival time. As described above, the first sensor may comprises at least one (or combination thereof) ICG, ECG, BCG, PCG, and/or SCG sensor coupled to the elongate band. The second sensor may comprise at least one PPG sensor or physical pressure pulse sensor coupled to the elongate band.

Absolute blood pressure bands (e.g., applanation tonometry approaches) may incorporate at least one pressure sensor comprising at least one pressure transducer, piezoelectric film, or piezoresistive film configured to non-invasively engage an anterior surface of the wrist of the user and be positioned over a radial artery so as to passively or actively measure the absolute blood pressure signals. The elongate band may further comprise at least one actuator configured to apply a constant or variable pressure over a radial artery of the wrist. Still further, at least one height sensor, barometric pressure sensor, gyroscope, or accelerometer may be coupled to the elongate band so as to account for hydrostatic pressure effects.

The telemetry interface of the elongate band may be configured to transmit the relative or absolute blood pressure signals to the second wrist-worn electronic device, a mobile device, tablet, computer, or database for further processing, storage, retrieval by other devices or programs, and/or display. For example, the telemetry interface of the elongate band may be configured to transmit the relative or absolute blood pressure signals to an electronic health or medical record (e.g., on a database) or health application software (e.g., on a mobile device, tablet, or computer). In another example, the telemetry interface of the elongate band may be configured to transmit the relative or absolute blood pressure signals to a display on the second wrist-worn electronic device or a third non-wrist device (e.g., a mobile device, tablet, computer), the display viewable by the user or a health care professional for use in diagnostic or therapeutic decision making. The telemetry interface of the elongate band may also be configured to transmit trending data (e.g., blood pressure index) for a time period based on the relative blood pressure signals, wherein the time period comprises one or more days, weeks, months, or years.

Embodiments of the present invention further include methods for providing a plurality of active bands for blood pressure monitoring of a user as described above. In one method, a first wrist-worn band is provided having at least one PIT sensor coupled to the first wrist-worn band and configured to non-invasively engage the skin over the wrist of the user for measuring user signals from the cardiovascular system for determining relative blood pressure signals. A second wrist-worn band is provided having at least one pressure sensor coupled to the second wrist-worn band and configured to non-invasively engage the skin over the wrist of the user for measuring user signals from the cardiovascular system for determining absolute blood pressure signals. The user is able to selectively choose and/or interchange between the first and second wrist-worn bands, wherein the selected first or second band is releasably coupleable to a wrist-worn electronic device. As discussed above, it will be appreciated that several other combinations of bands having various sensing modalities are possible (e.g., first band requiring user interaction for blood pressure measurement while the second band is passive for blood pressure measurement).

Embodiments of the present invention further include methods for obtaining and transmitting relative blood pressure measurements of a user. One method comprising sensing, with a first sensor of a wrist-worn device non-invasively engaging the skin on the wrist of the user, first user signals indicative of ventricular ejections of blood from the heart of the user, the first sensed ventricular ejection signals each having an associated ventricular ejection time. A second sensor of the wrist-worn device non-invasively engaging the skin on the wrist of the user, measures second user signals indicative of pressure pulse arrivals in the wrist, the second sensed pressure pulse signals associated with the first sensed ventricular ejection signals, each of the second sensed pressure signals having an associated pulse arrival time. FIT measurements are identified from a difference between the first sensed ventricular ejection signals and the second sensed pressure signals and the PTT measurements are transmitted directly to a second electronic device or database in a non-calibrated (e.g., non-manipulated) format. For example, the second electronic device may comprise a watch, phone, tablet, or a computer. The second electronic device or database may be better suited in some instances to store individual calibration equations and process the PTT measurements to determine absolute blood pressure values. In some instances, the PTT measurements may be transmitted to a phone or tablet, and then re-transmitted to a cloud database for further processing. In other instances, the PTT measurements may be transmitted specifically to an electronic health or medical record or health application software. Still further, trending data may be transmitted for a specified time period based on the PTT measurements, wherein the time period comprises one or more days, weeks, months, or years. As discussed above, the second electronic device or database may not only process the PTT measurements (e.g., calibration of relative blood pressure signals), but also allow for storage of the data in a variety of formats (e.g., non-calibrated PTT measurements, trending data, absolute blood pressure values), retrieval of the data by other devices or programs, and/or display of the data.

Embodiments of the present invention further include methods for filtering non-invasive blood pressure measurements from a wrist-worn device. One method comprises receiving a plurality of relative or absolute blood pressure signals from at least one pulse transit time (PTT) or pressure sensor coupled to a wrist of a user, filtering the relative or absolute blood pressure signals based on contextual information associated with the user, and discarding or masking the filtered relative or absolute blood pressure signals. Contextual filtering may be based on a variety of information that may provide context for any measured blood pressure changes or artifacts. The contextual information associated with the user may comprise at least one of the following: (a) input from the user, (b) health application software information associated with the user, (c) an electronic medical record information associated with the user, (d) location information associated with the user (e.g., GPS), (e) calendar information associated with the user, (f) time information, (g) temperature information, (h) current activity as entered by the user or detected by the device (e.g. sitting, standing, walking, sleeping, driving), or (i) medication usage/dosage. For example, location information may allow filtering of blood pressure signals when the user is driving, calendar information may allow filtering of blood pressure signals when the user is at an exercise class, and temperature information may allow filtering of blood pressure signals when the user is in an extremely cold environment. Filtering relative or absolute blood pressure signals may also reduce power consumption of the wrist-worn device as only non-filtered relative or absolute blood pressure signals are transmitted to a second wrist worn device, mobile device, tablet, computer, or database. In addition to filtering to remove certain measurements, the contextual information can also be used to annotate blood pressure information over time, in order to discern trends that affect blood pressure (e.g. blood pressure reduction after walking, blood pressure increase during driving).

Embodiments of the present invention further include methods for accounting for hydrostatic effects, particularly for non-invasive blood pressure measurements from a wrist-worn device having ICG/ECG sensors for cross body measurements (e.g., finger to opposite wrist-worn device) or a BCG sensor for passive measurements. For example, pressure differentials as large as 30 mmHg can be due to a 40 cm variation in the height of the sensor relative to the heart during a measurement. Methods are provided herein for addressing pressure differentials due to taking a measurement when the user's wrist is at a various heights (e.g., down by their side, up in the air, folded across, etc.) relative to the heart. One method comprises receiving relative blood pressure signals from PIT measurements from a wrist-worn device, wherein each PTT measurement comprises a time period from ventricular ejection of a heart to pulse arrival at a wrist and the PTT ventricular ejection of the heart is determined from at least one ICG, ECG, or BCG sensor. A signal is received indicative of a height of the sensor relative to the heart associated with each PTT measurement and the relative blood pressure signals adjusted based on the height of the sensor relative to the heart signal associated with each PTT measurement so as to account for hydrostatic pressure differentials. For example, the height signal may be received and/or calculated from at least a height sensor, accelerometer, gyroscope, and/or a barometric pressure sensor coupled to the wrist-worn device. Still further, user input or anthropometric data may also be utilized in combination with the height sensor, accelerometer, gyroscope, and/or a barometric pressure sensor signals to determine the height measurement. It will be appreciated however that hydrostatic effects may also be negated by taking measurements while the user is lying down (e.g., BCG passive monitoring while the user is asleep) so that there is little to no variation between the height of the wrist sensor relative to the heart or by aligning the wrist sensor relative to the height of the heart during a measurement (e.g., ICG contact with the sternum).

The details of one or more implementations are set forth in the accompanying drawings and the description below. A better understanding of the features and advantages of the present invention will be obtained by reference to the description and drawings, and from the claims.

BRIEF DESCRIPTION OF THE DRAWINGS

FIGS. 42-45 illustrate selective actuation of a skin interface against a wrist of a user according to embodiments of the present invention.

DETAILED DESCRIPTION OF THE INVENTION

Figure 1:
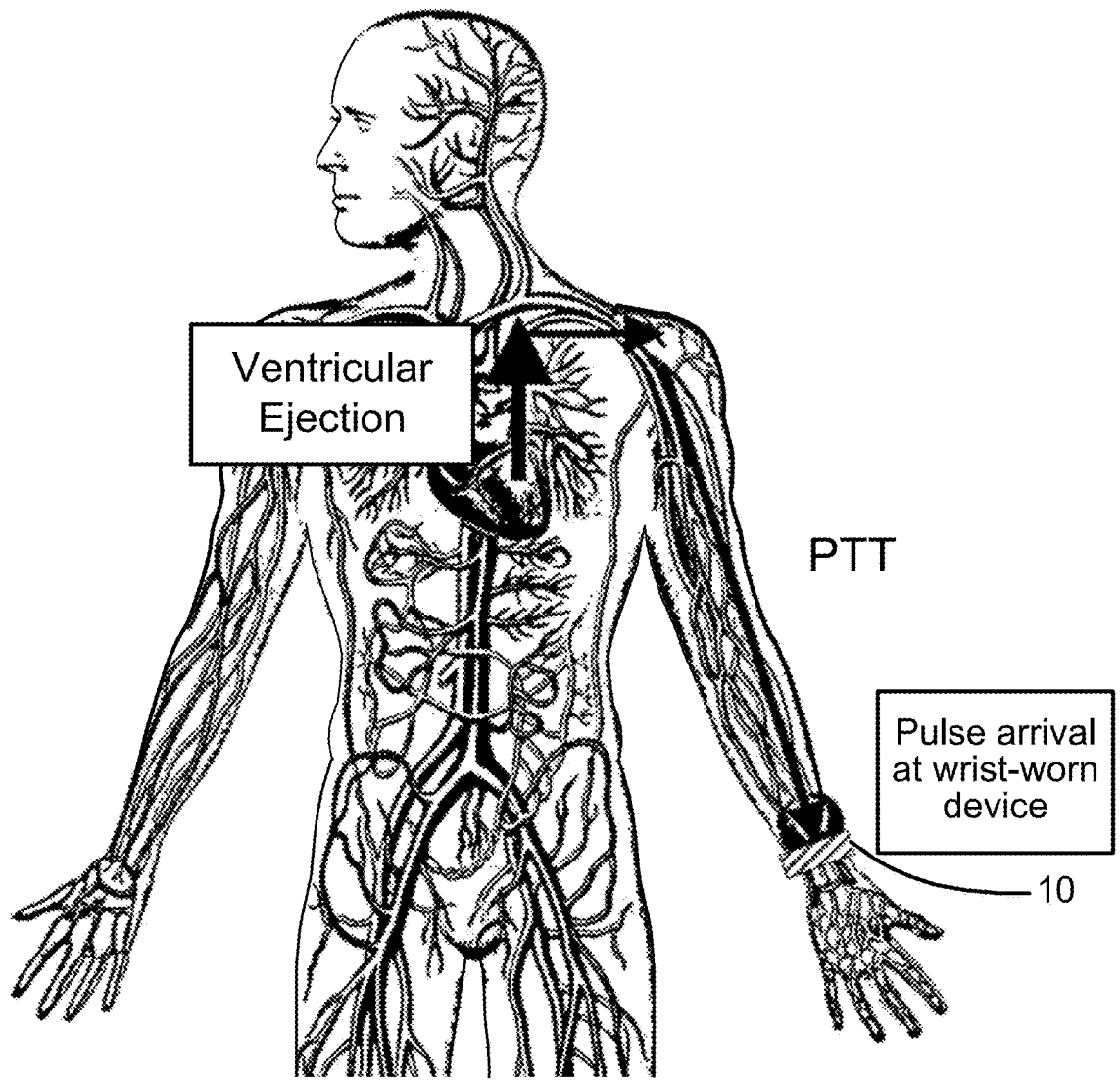
FIG. 1 illustrates a propagation path of a blood pressure pulse from ejection from the left ventricle of the heart to a wrist on which a wrist-worn blood pressure measurement device is worn according to embodiments of the present invention.

FIG. 1 illustrates a propagation path of a blood pressure pulse from ejection from the left ventricle of a subject's heart to a wrist on which a wrist-worn blood-pressure measurement device 10 is worn, in accordance with many embodiments. The wrist-worn device 10 is configured to detect when the blood corresponding to the blood pressure pulse is ejected from the left ventricle of a subjects heart and when the blood pressure pulse arrives at the wrist-worn device 10. The wrist-worn device 10 is configured to calculate a pulse transit time (PTT) for the blood pressure pulse for the transit of the blood pressure pulse from the left ventricle to the wrist-worn device 10. The determined PTT is then used to determine one or more blood-pressure values for the subject.

In general, a PTT is the time it takes for a pulse pressure wave to propagate through a length of a subject's arterial tree. PTT has a nonlinear relationship with blood pressure. Factors that can impact how fast a blood pressure pulse will travel at a given blood-pressure in a particular artery, include, for example, arterial stiffness, arterial wall thickness, and arterial inner diameter. Equation (1) provides a functional relationship between PTT and mean arterial blood pressure (MAP).

$$MAP = \frac{1}{\alpha} \ln\left[\frac{\rho D(\Delta d)^2}{hE_0(PTT)^2}\right] \quad (1)$$

where: MAP is mean arterial blood pressure;
PTT is Pulse Transit Time;
h is arterial wall thickness;
D is artery diameter;
$\rho$ is density of blood;
$E_0$ is the Young's modulus of the artery at zero pressure;
$\alpha$ is a subject dependent physiological constant; and
$\Delta d$ is the arterial distance between the subjects left ventricle and the wrist.

The pressure pulse travels through different arteries during its transit from the left ventricle to the wrist. As a result, variation in corresponding variables in equation (1), for example, arterial wall thickness (h), artery diameter (D), and Young's modulus of the artery at zero pressure ($E_0$), will change the relationship between blood pressure and how fast the blood pressure pulse travels through the respective artery. Each blood pressure pulse, however, will travel through the same arteries during transit from the left ventricle to the wrist. Accordingly, a relationship between the overall PTT from the left ventricle to the wrist and MAP can be given by replacing arterial wall thickness (h), artery diameter (D), and Young's modulus of the artery at zero pressure ($E_0$) with respective effective values suitable for the combination of all the arteries through which the pressure pulse travels from the left ventricle to the wrist. Therefore, equation (1) can be simplified to the relationship given below in equation (2).

$$MAP = \frac{1}{\alpha} \ln\left[\frac{K}{(PTT)^2}\right] \quad (2)$$

where $$K = \frac{\rho D(\Delta d)^2}{hE_0}$$

is suitable for the subject and the arterial tree segment over which PIT is being measured.

The values of (K) and ($\alpha$) can be determined using any suitable approach. For example, an oscillometric blood pressure measurement cuff can be used to measure one or more blood pressure values for the subject at or at about the same time as when corresponding one or more PTTs are determined for the subject via the wrist-worn device 10. Suitable calibration data can then be formulated using the oscillometric blood pressure measurement cuff measured blood pressure values and the corresponding one or more PTTs for the subject using known approaches. For example, a least squares method can be used to determine suitable values or relationships for determining the values of (K) and ($\alpha$).

A similar approach can be used to predict MAP, systolic blood pressure (SBP), and diastolic blood pressure (DBP) values based on a measured PTT value. For example, equations (3), (4), and (5) are example regression equations that can be used to predict MAP, SBP, and DBP, respectively, from a measured PTT.

$$MAP = K_{MAP} \times [\log(PTT) - \log(PTT_0)] + MAP_{BASELINE} \quad (3)$$

where: MAP is predicted mean arterial blood pressure;
$MAP_{BASELINE}$ is a baseline measured MAP;
$K_{MAP}$ is a subject dependent constant for MAP;
PTT is the measured pulse transit time; and
$PTT_0$ is the measured pulse transit time for $MAP_{BASELINE}$.

$$SBP = K_{SBP} \times [\log(PTT) - \log(PTT_0)] + SBP_{BASELINE} \quad (4)$$

where: SBP is predicted systolic blood pressure;
$SBP_{BASELINE}$ is a baseline measured systolic blood pressure;
$K_{SBP}$ is a subject dependent constant for systolic blood pressure;
PTT is the measured pulse transit time; and
$PTT_0$ is the measured pulse transit time for $SBP_{BASELINE}$.

$$DBP = K_{DBP} \times [\log(PTT) - \log(PTT_0)] + DBP_{BASELINE} \quad (5)$$

where: DBP is predicted diastolic blood pressure;
$DBP_{BASELINE}$ is a baseline measured diastolic blood pressure;
$K_{DBP}$ is a subject dependent constant for diastolic blood pressure;
PTT is the measured pulse transit time; and
$PTT_0$ is the measured pulse transit time for $DBP_{BASELINE}$.

Figure 2:
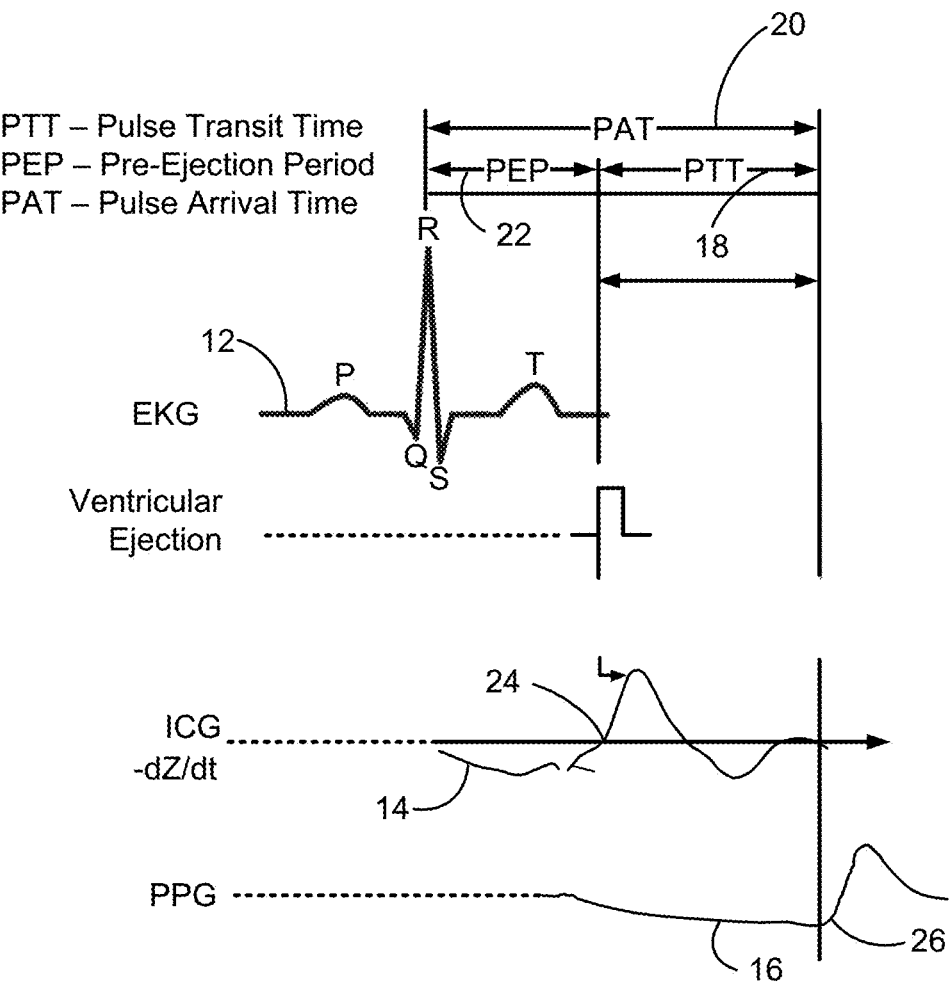
FIG. 2 illustrates EKG, ICG, and PPG signals relative to a PIT for a blood pressure pulse propagating from the left ventricle to a wrist on which a wrist-worn blood pressure measurement device is worn according to embodiments of the present invention.

FIG. 2 shows an EKG trace segment 12, an ICG trace segment 14, and a PPG signal 16 relative to a pulse transit time (PTT) 18 for a blood pressure pulse between the left ventricle of the subject to the wrist-worn device 10. In many embodiments, the wrist-worn device 10 includes electrodes used to generate an EKG trace and an ICG trace for the subject and a PPG sensor to generate a PPG signal for the subject. The EKG trace segment 12 has a segment (QRS) known as the QRS complex, which reflects the rapid depolarization of the right and left ventricles. The prominent peak (R) of the EKG trace corresponds to beginning of contraction of the left ventricle. A pulse arrival time (PAT) 20 is the time between the peak (R) of the EKG trace and arrival of the blood pressure pulse at the wrist-worn device 10. As the left ventricle contacts, pressure builds within the left ventricle to a point where the pressure exceeds pressure in the aorta thereby causing the aortic valve to open. A pre-ejection period (PEP) 22 is the time period between the peak (R) of the EKG trace and the opening of the aortic valve. The PEP 22 correlates poorly with blood pressure. The ICG trace 14 provides a better indication as to when the aortic valve opens. The ejection of blood from the left-ventricle into the aorta results in a significant temporary decrease in the thoracic impedance of the subject, which corresponds to a temporary increase in the ICG trace, which is the negative of the change of impedance with time. Accordingly, in many embodiments, the ICG trace 14 is processes to identify a start 24 of the temporary increase in the ICG trace as corresponding to the opening of the aortic valve and the start of the propagation of the blood pressure pulse. In many embodiments, the arrival of the blood pressure pulse is detected via the PPG signal 16, which includes an inflection point 26 that occurs upon arrival of the blood pressure pulse to the wrist-worn device 10.

Figure 3:
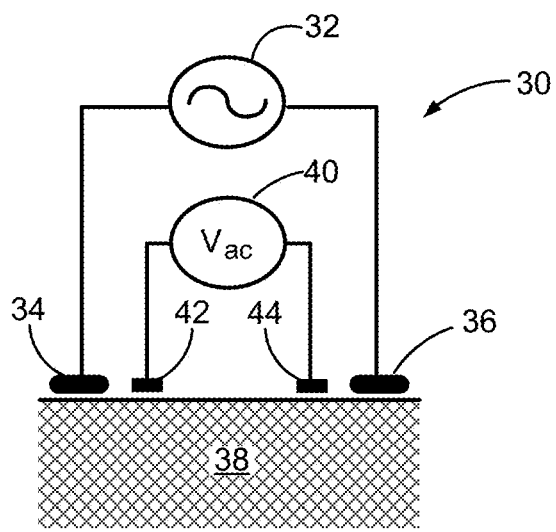
FIG. 3 schematically illustrates a four-electrode configuration used to measure impedance of a subject according to embodiments of the present invention.

FIG. 3 schematically illustrates a four-electrode configuration 30 used to measure impedance of a subject, in accordance with many embodiments. The four-electrode configuration 30 includes a drive current generator 32 electrically coupled with a first drive current electrode 34 and a second drive current electrode 36. In many embodiments, the drive current generator 32 imparts an alternating current to a subject 38 via the electrodes 34, 36. The four-electrode configuration 30 also includes a voltage sensor 40 electrically coupled with a first sense electrode 42 and a second sense electrode 44. The use of the sense electrodes 42, 44, which are separated from the drive current electrodes 34, 36, serves to reduce the impact of impedance and contract resistance by sensing voltage with electrodes that are transferring much lower levels of current relative to the current drive electrodes 34, 36. In many embodiments, the alternating drive current has a frequency between 20 kHz and 100 kHz. Drive currents below 20 kHz may create muscle excitation. And while drive currents at 100 kHz produces skin-electrode impedance approximately 100 times lower than at low frequencies, applied drive currents at greater than 100 kHz may result in stray capacitance. A drive current of about 85 kHz is preferred.

Figure 4:
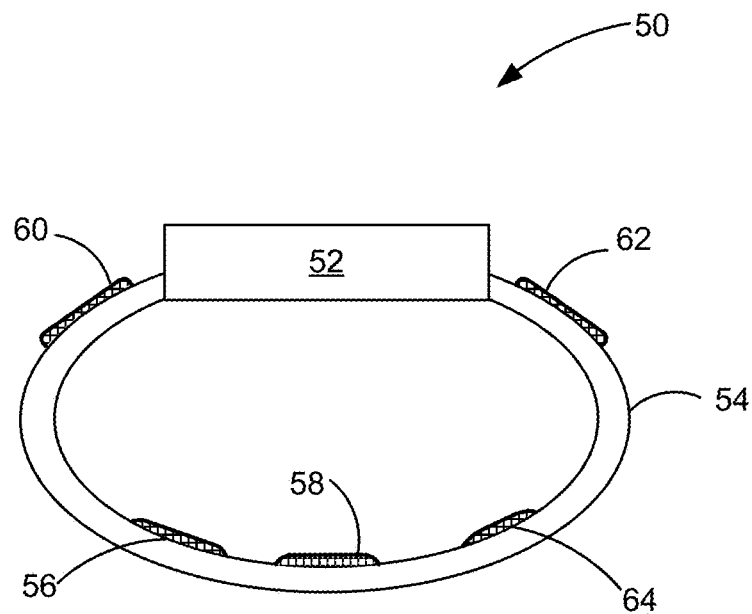
FIGS. 4-5 are schematic side views of wrist-worn blood-pressure measurement devices according to embodiments of the present invention FIG. 6 schematically illustrates electrode locations and related body impedances in an approach for measuring chest-cavity impedance variations according to embodiments of the present invention.

FIG. 4 shows a side view of a wrist-worn blood-pressure measurement device 50, in accordance with many embodiments. The wrist-worn device 50 includes a main unit 52, a wrist-worn elongate band 54, a first drive current electrode 56, a first sense electrode 58, a second drive current electrode 60, a second sense electrode 62, and a PPG sensor 64. The first drive current electrode 56, the first sense electrode 58, and the PPG sensor 64 are: 1) supported on the wrist-worn elongate band 54, 2) positioned and oriented to interface with a subject's wrist upon which the wrist-worn device 50 is worn, and 3) operatively connected with the main unit 52. The second drive current electrode 60 and the second sense electrode 62 are: 1) supported on the wrist-worn elongate band, 2) positioned and oriented to be interfaceable with the subject so that the drive current travels through the thoracic cavity of the subject (e.g., with separate fingers on the arm opposite to the arm on which the wrist-worn device 50 is worn), and 3) operatively connected with the main unit 52. The main unit 52 includes circuitry and/or software for imparting drive current through the subject via the first and second drive current electrodes 56, 60 and for processing signals from the PPG sensor 64 and the first and second sense electrodes 58, 62 so as to measure a PTT and calculate one or more blood pressure values for the subject based on the PTT.

Figure 5:
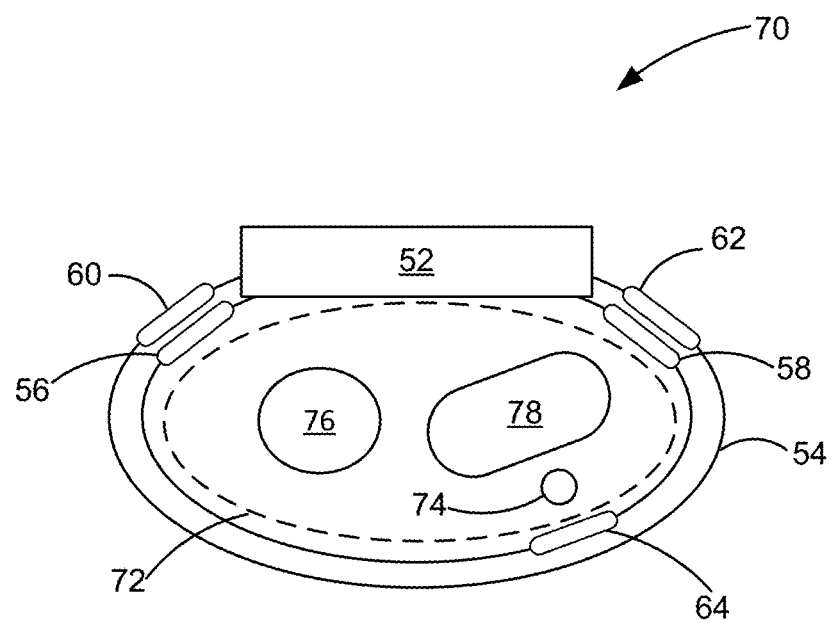

FIG. 5 shows a side view of another wrist-worn blood-pressure measurement device 70, in accordance with many embodiments. The wrist-worn device 70 includes the same components as for the wrist-worn device 50, but has the first drive current electrode 56 and the first sense electrode 58 located to enhance contact pressure with a wrist 72 of the subject. In the illustrated embodiment, the first drive current electrode 56 is disposed on a directly opposite inside surface of the wrist-worn band 54 relative to the second drive current electrode 60 such that contact pressure between, for example, a finger of the subject and the second drive current electrode 60 transfers compression through the wrist-worn band 54 to the first drive current electrode 56, thereby increasing contact pressure between the first drive current electrode 56 and the wrist 72. In a similar fashion, the first sense electrode 58 is disposed on a directly opposite inside surface of the wrist-worn band 54 relative to the second sense electrode 62 such that contact pressure between, for example, a finger of the subject and the second sense electrode 62 transfers compression through the wrist-worn band 54 to the first sense electrode 58, thereby increasing contact pressure between the first sense electrode 58 and the wrist 72. Any suitable variation can be used. For example, the locations of the first drive current electrode 56 and the first sense electrode 58 can be exchanged. As another example, the electrodes 56, 58, 60, 62 can be located at any other suitable locations on the wrist-worn band 54. As another example, any suitable number of the electrodes 56, 58, 60, 62 can be disposed on the main unit 52.

In the illustrated embodiment, the PPG sensor 64 is located on the wrist-worn band 54 so as to be disposed to sense the arrival of the blood-pressure pulse within a radial artery 74 of the subject. Cross sections of the ulna bone 76 and the radius bone 78 of the subject are shown for reference.

Figure 6:
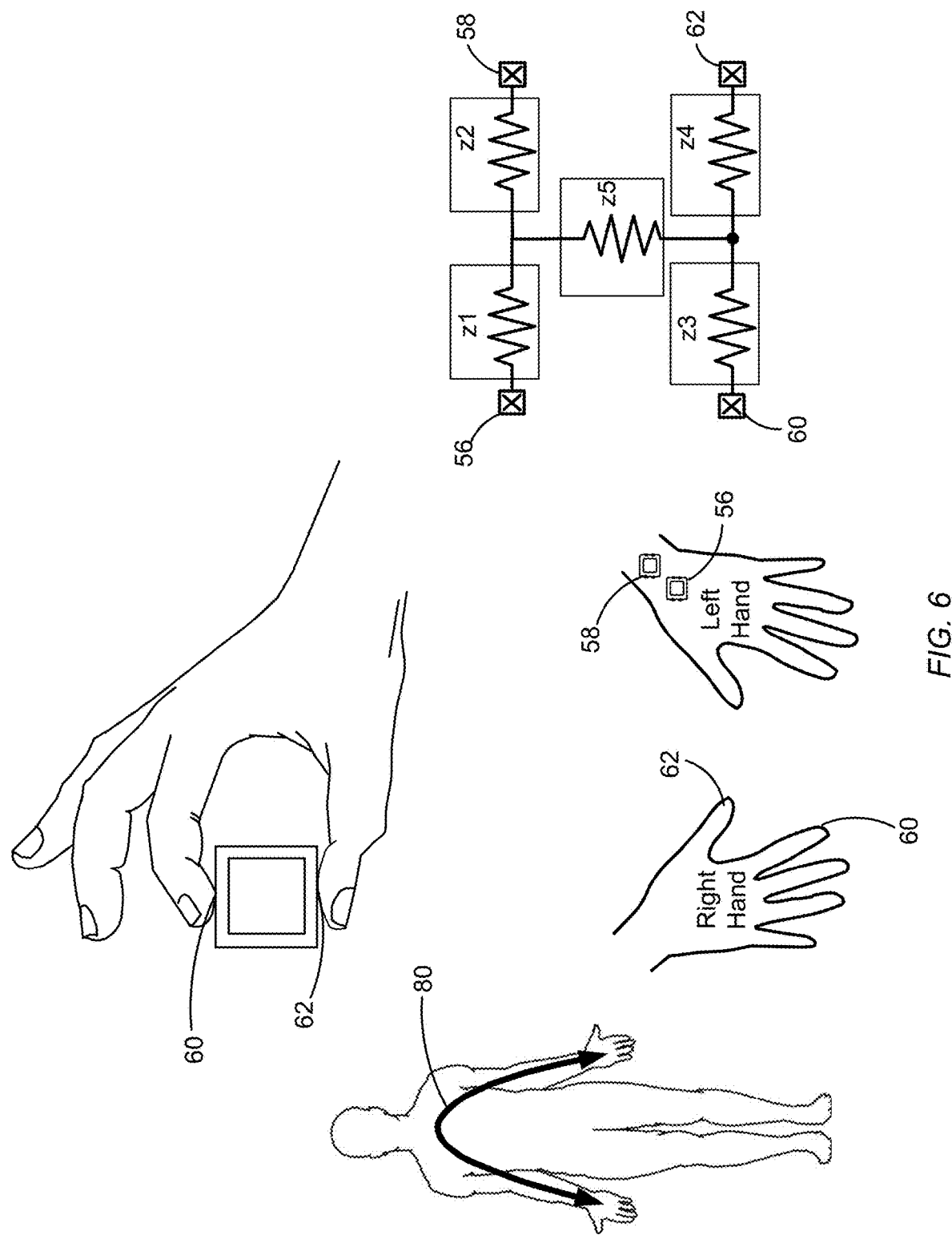
FIG. 6A is a cross-sectional view of another wrist-worn blood-pressure measurement device having exterior electrodes shown engaged with skin of a user's thorax according to embodiments of the present invention.

FIG. 6 schematically illustrates electrode locations and related body impedances in an approach for measuring chest cavity impedances, in accordance with many embodiments. In the illustrated approach, the first drive current electrode 56 and the first sense electrode 58 are held in contact with the left wrist of the subject. The second drive current electrode 60 is contacted by the right index finger of the subject. The second sense electrode 62 is contacted by the right thumb of the subject. The first and second drive current electrodes 56, 60 impart a cross-body alternating drive current 80 between the drive current electrodes 56, 60. The cross-body drive current 80 propagates through the left wrist, through the left arm, through the thoracic cavity, through the right arm, and through the right index finger. The combined impedance of the left wrist local to the first drive current electrode 56 and the contact impedance of the first drive current electrode 56 and the left wrist is schematically represented as an impedance (Z1). The combined impedance of the right index finger in contact with the second drive current electrode 60 and the contact impedance of the second drive current electrode 60 and the right index finger is schematically represented as an impedance (Z3). The net cross-body impedance between the impedances (Z1 and Z3) is schematically represented as an impedance (Z5). The combined impedance of the left wrist local to the first sense electrode 58 and the contact impedance of the first sense electrode 58 and the left wrist is schematically represented as an impedance (Z2). The combined impedance of the right thumb in contact with the second sense electrode 62 and the contact impedance of the second sense electrode 62 and the right thumb is schematically represented as an impedance (Z4). In many embodiments, because the first and second sense electrodes 58, 62 are configured to measure a voltage difference without transferring any significant amount of current, the resulting voltage drops across the impedances (Z2 and Z4) are small so that the voltage difference sensed by the first and second sense electrodes 58, 62 matches the voltage difference across the impedance (Z5).

Figure 6A:
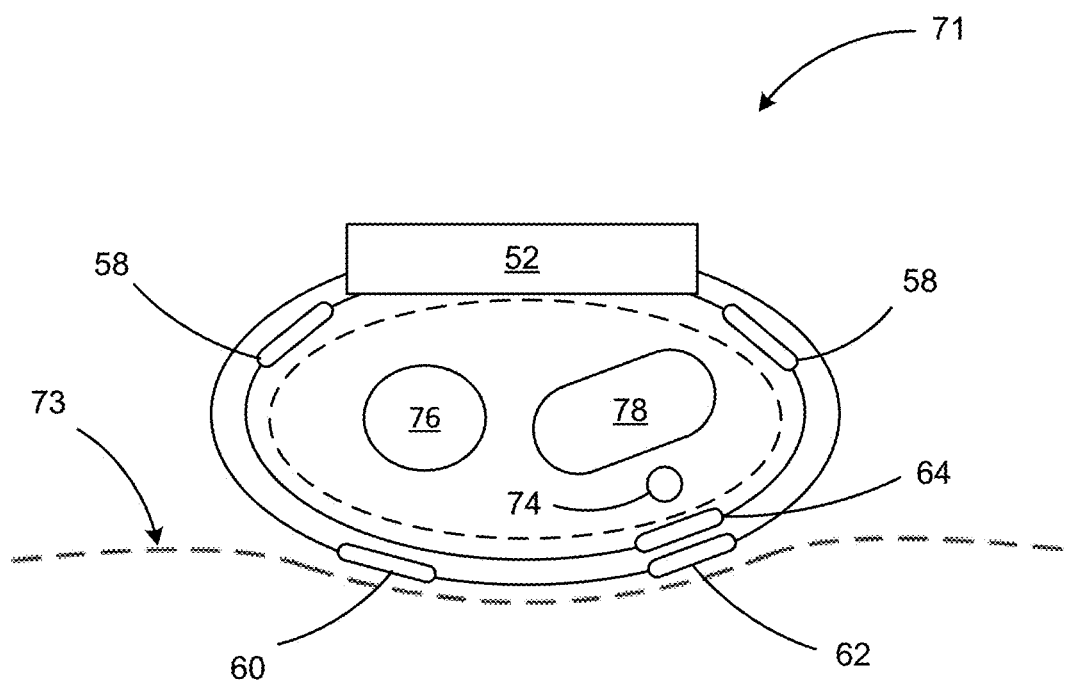

FIG. 6A shows a side view of another wrist-worn blood-pressure measurement device 71, in accordance with many embodiments. The wrist-worn device 71 includes the same components as for the wrist-worn device 70, but has the second drive current electrode 60 and the second sense electrode 62 located so that they can be engaged with another portion of the user via the user positioning the arm on which the wrist-worn device 71 is worn so as to press the electrodes 60, 62 into contact with any suitable skin portion of the user. For example, FIG. 6A illustrates the electrodes 60, 62 being pressed against a skin location on the user's thorax 73 (e.g., lower breast skin opposite to the arm on which the device 71 is worn). As another example, the electrodes 60, 62 can be pressed against skin on the user's arm opposite to the arm on which the device 71 is worn.

Figure 7:
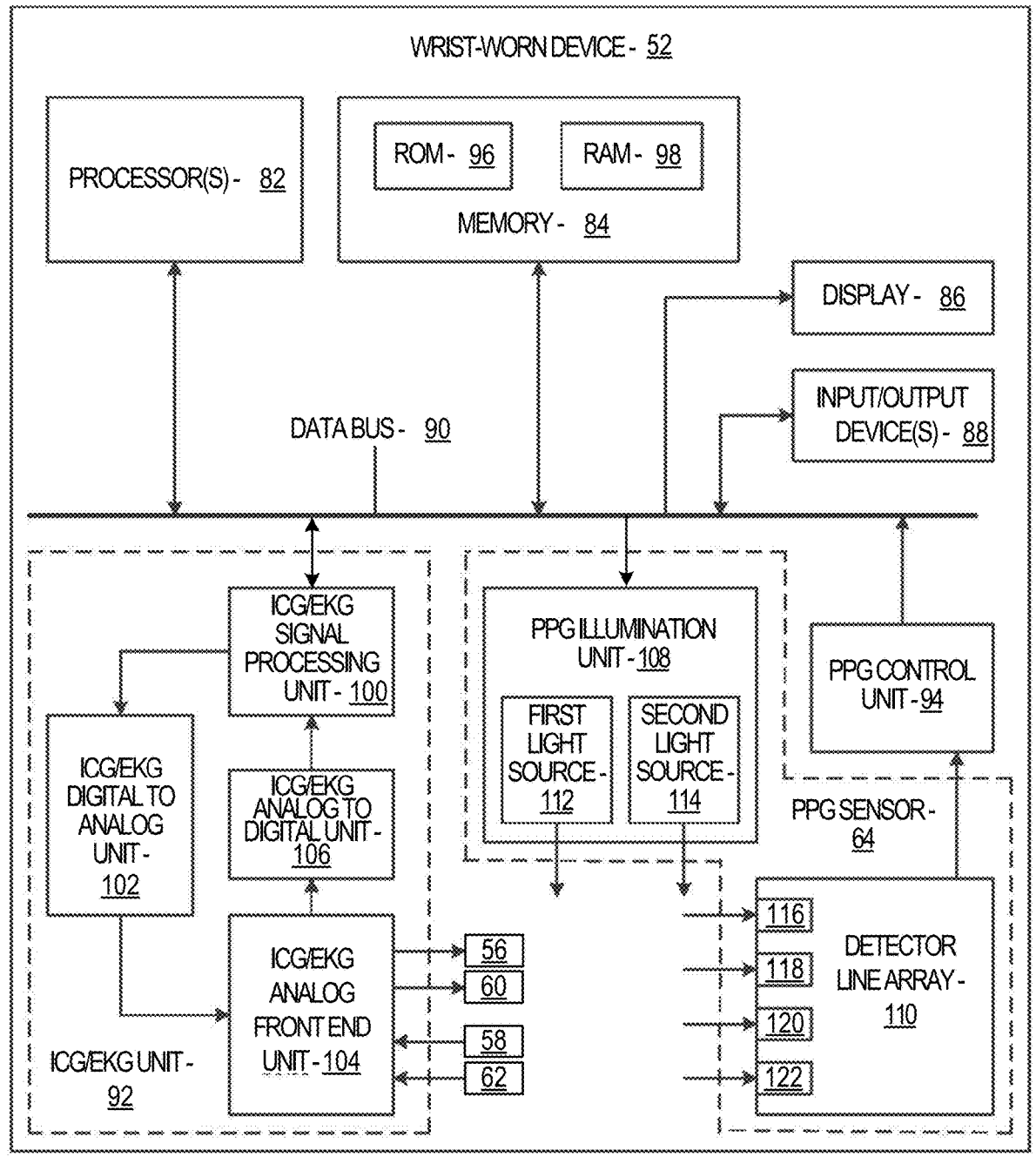
FIG. 7 is a schematic diagram of a wrist-worn blood-pressure measurement device main unit according to embodiments of the present invention.

FIG. 7 schematically represents an embodiment of a wrist-worn device for measuring blood pressure. In the illustrated embodiment, the wrist-worn device includes one or more processors 82, memory 84, a display 86, one or more input/output devices 88, a data bus 90, an ICG/EKG unit 92, the PPG sensor 64, and a PPG sensor control unit 94. In many embodiments, the memory 84 includes read only memory (ROM) 96, and random access memory (RAM) 98. The one or more processors 82 can be implemented in any suitable form, including one or more field-programmable gate arrays (FPGA).

The ICG/EKG unit 92 includes an ICG/EKG signal processing unit 100, an ICG/EKG digital to analog unit 102, an ICG/EKG analog front end unit 104, and an ICG/EKG analog to digital unit 106. The signal processing unit 100 generates a digital alternating drive signal (e.g., a digital drive signal corresponding to an 85 kHz sinusoidal drive current) and supplies the digital alternating drive signal to the digital to analog unit 102. The digital to analog unit 102 generates a sinusoidal drive current matching the digital alternating drive signal and supplies the sinusoidal drive current to the analog front end unit 104. The analog front end 100 supplies the sinusoidal drive current to the first and second drive current electrodes 56, 60 for propagation through the subject (e.g., as the cross-body alternating drive current 80 illustrated in FIG. 6). Resulting voltage levels are sensed via the first and second sense electrodes 58, 62. Signals from the sense electrodes 58, 62 are processed by the analog front end 104 to generate an analog voltage signal supplied to the analog to digital unit 106. The analog to digital unit 106 converts analog voltage signal to a corresponding digital signal that is supplied to the signal processing unit 100. The signal processing unit 100 then generates corresponding ICG/EKG digital data that can be processed by the one or more processors 82 to determine the opening of the aortic valve and therefore the corresponding start of the propagation of a blood pressure pulse from the left ventricle to the wrist-worn device.

The PPG sensor unit 64 includes a PPG illumination unit 108 and detector line array 110. The PPG illumination unit 108 includes two light sources 112, 114 which transmit light having different wavelengths onto the wrist. While any suitable wavelengths can be used, the first light source 112 generates a beam of light having a wavelength of 525 nm. The second light source 114 generates a beam of light having a wavelength of 940 nm. Any suitable number of light sources and corresponding wavelengths can be used and selected to provide desired variation in tissue penetrating characteristics of the light. The detector line array 110 can include any suitable number of light detectors. In many embodiments, the light detectors are disposed at a plurality of different distances from the light sources 112, 114 so that the detected light is associated with different mean penetration depths so as to enable detection of the arrival of the blood pressure pulse at different layers and/or within a layer of the wrist deeper than a layer sensed by a single light source and single detector PPG sensor. In the illustrated embodiment, the detector line array 110 includes four light detectors 116, 118, 120, 122, with each of the light detectors 116, 118, 120, 122 being disposed at a different distance from the light sources 112, 114. For example, the light detectors 116, 118, 120, 122 can be disposed at 2 mm, 3 mm, 4 mm, 6 mm, or 10 mm respectively, from each of the light sources 112, 114. Signals generated by the light detectors 116, 118, 120, 122 are supplied to the PPG control unit 94, which includes an analog to digital converter to generate PPG sensor digital data that can be processed by the one or more processors 82 to determine the arrival of the blood pressure pulse to the wrist-worn device. The PPG control unit 94 controls activation of the light sources 112, 114, and can alternately illuminate the light sources 112, 114 at a frequency sufficiently high to enable combined assessment of the PPG sensor digital data generated by illumination of the wrist with the different wavelengths provided by the light sources 112, 114.

The generated ICG/EKG digital data and the PPG sensor digital data can be transferred to, and stored in, the RAM 98 for any suitable subsequent use. For example, the data can be: 1) processed by the one or more processors 82 to determine PTTs and corresponding blood pressure values for the subject, 2) displayed on the display 86, and/or 3) output via the input/output devices 88 for any suitable purpose such as to a health care professional and/or a monitoring service. In many embodiments, the one or more processors 82 processes the ICG/EKG and PPG sensor digital data to generate trending data for a time period based on the one or more relative blood pressure values. Such trending data can be generated for any suitable time period, for example, for one or more days, one or more weeks, one or more months, and/or one or more years. One or more blood pressure values and/or associated trending data can be: 1) stored in the RAM 98, 2) displayed on the display 86, and/or 3) output via the input/output devices 88 for any suitable purpose such as to a health care professional and/or a monitoring service.

Figure 8:
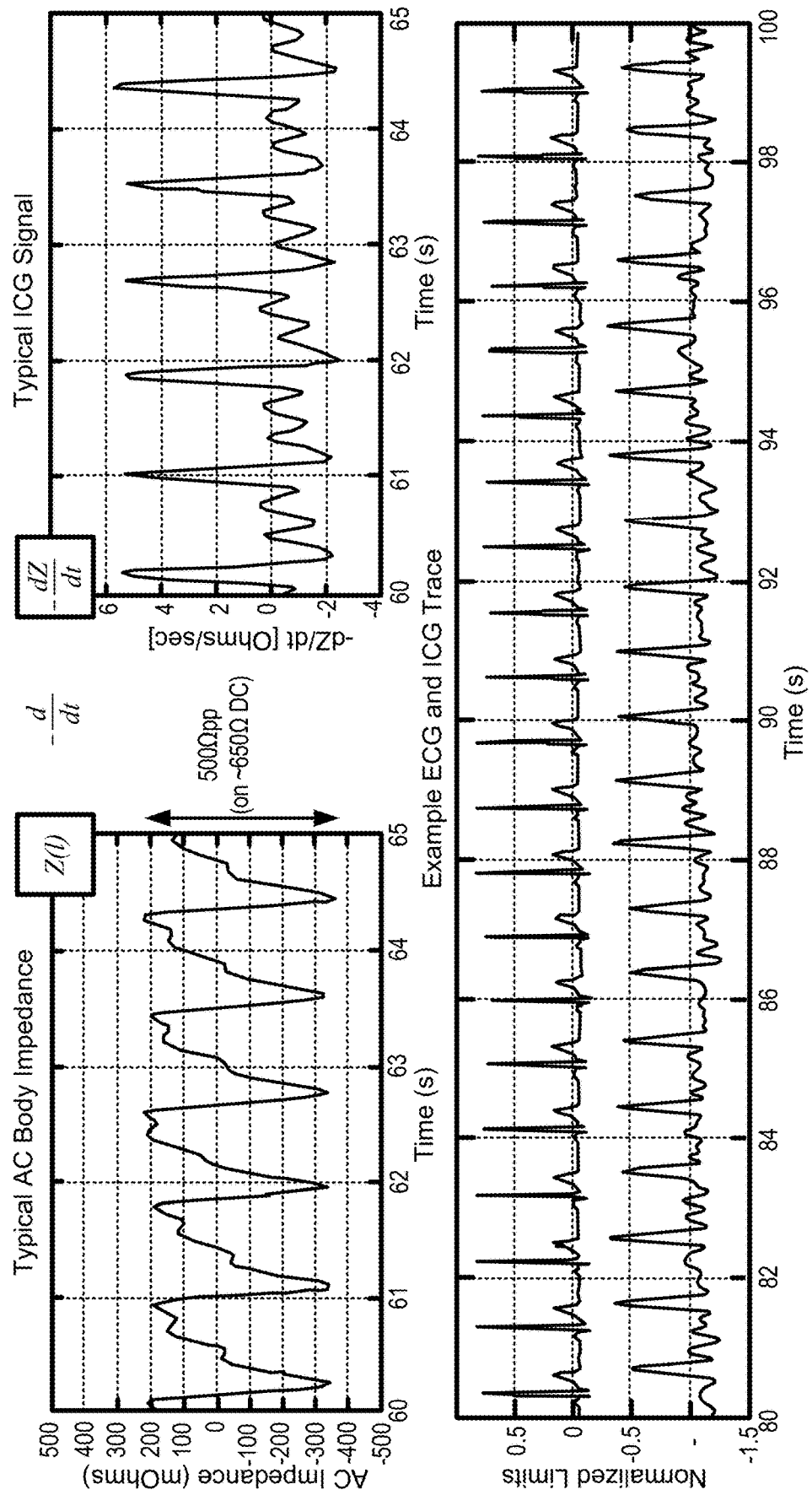
FIG. 8 shows typical EKG and ICG data traces according to embodiments of the present invention.

FIG. 8 shows typical EKG and ICG data traces, in accordance with many embodiments. AC body impedance Z(t) is calculated using the applied drive current I(t) and the measured resulting voltage difference signal V(t) per equation (6).

$$Z(t)=V(t)/I(t) \tag{6}$$

The ICG signal is then generated by calculating the negative time differential of Z(t) as shown in equation (7).

$$\text{ICG Signal}=-dZ/dt \tag{7}$$

The EKG signal is generated by voltages generated within the body having variations at a much lower frequency (e.g., 0.05-100 Hz) in comparison to the relatively higher frequency of the impedance drive current (e.g., 85 kHz). Accordingly, signals from the first and second sense electrodes 58, 62 can be processed to generate both the ICG and the EKG traces. When both the EKG and the ICG traces are generated, the pre-ejection period (PEP) can be determined.

While the PEP time period does not correlate well with blood pressure, it may correlate with an extent to vasomotion (vasodilation and vasoconstriction) and thereby serve as an additional factor that can be used to correlate blood pressure with measured PTT. For example, a relationship can be developed where predicted blood pressure is a correlated function of both PTT and PEP.

Figure 9:
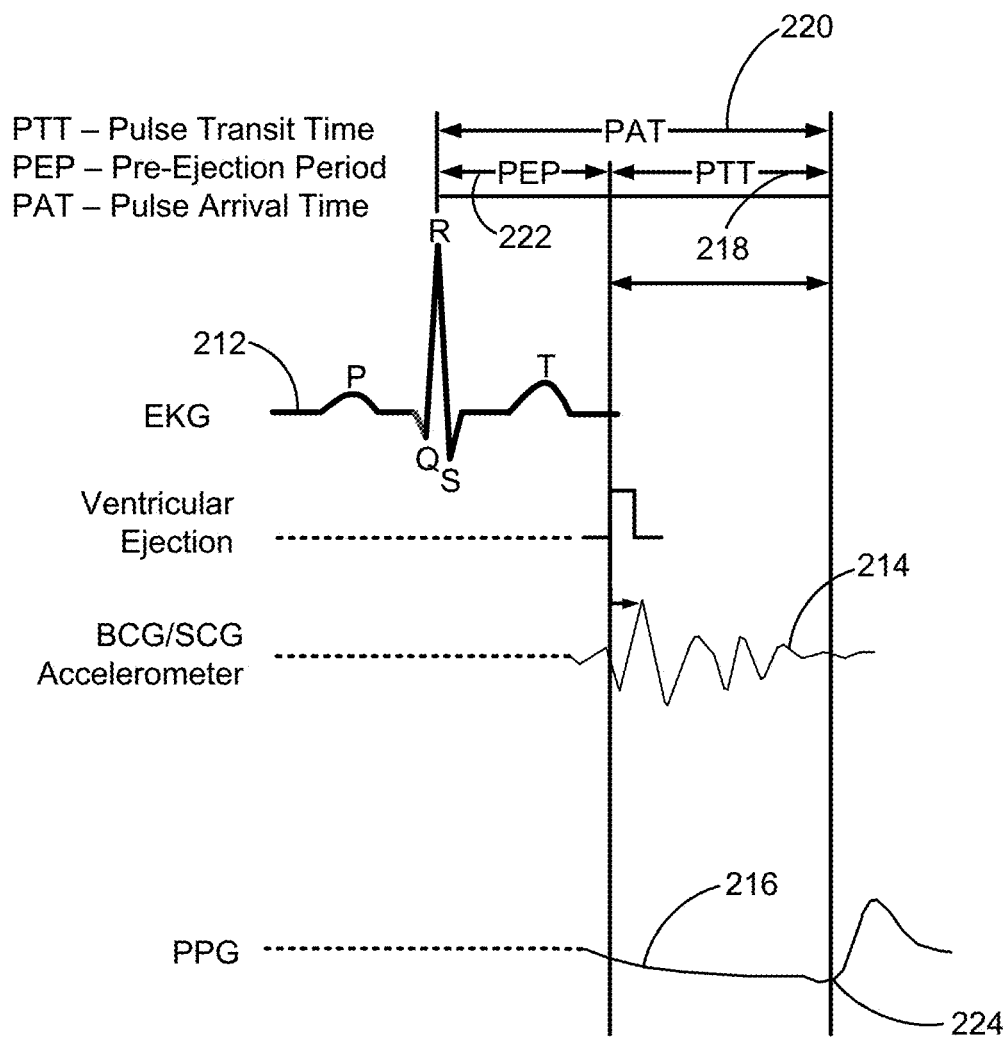
FIG. 9 illustrates accelerometer and PPG signals relative to a PTT for a blood pressure pulse propagating from the left ventricle to a wrist on which a blood pressure measurement device is worn according to embodiments of the present invention.

FIG. 9 shows an electrocardiogram (EKG) trace segment 212, a Ballisto-Cardiogram (BCG) or Seismo-Cardiogram (SCG) trace segment 214, and a PPG signal 216 relative to a pulse transit time (PTT) 218 for a blood pressure pulse between the left ventricle of the subject to the wrist-worn device 210. In many embodiments, the wrist-worn device 210 includes an accelerometer and a PPG or pulse pressure sensor. The accelerometer measures one or more accelerations used to generate a BCG and/or a SCG, which can be processed to identify when the blood pressure pulse originates from the subject's left ventricle. A PPG sensor is used to generate a PPG signal for the subject. The EKG trace segment 212 is shown for reference in describing the operation of the heart. The EKG trace segment 212 has a segment (QRS) known as the QRS complex, which reflects the rapid depolarization of the right and left ventricles. The prominent peak (R) of the EKG trace corresponds to beginning of contraction of the left ventricle. A pulse arrival time (PAT) 220 is the time between the peak (R) of the EKG trace and arrival of the blood pressure pulse at the wrist-worn device 210. As the left ventricle contacts, pressure builds within the left ventricle to a point where the pressure exceeds pressure in the aorta thereby causing the aortic valve to open. A pre-ejection period (PEP) 222 is the time period between the peak (R) of the EKG trace and the opening of the aortic valve. The PEP 222 correlates poorly with blood pressure. The BCG/SCG trace 214 can be processed to identify when the aortic valve opens. The ejection of blood from the left-ventricle into the aorta results in an associated acceleration of the chest cavity that is detected via the accelerometer included in the wrist-worn device 210. In many embodiments, the arrival of the blood pressure pulse is detected via the PPG signal 216, which includes an inflection point 224 that occurs upon arrival of the blood pressure pulse to the wrist-worn device 210.

Figure 10:
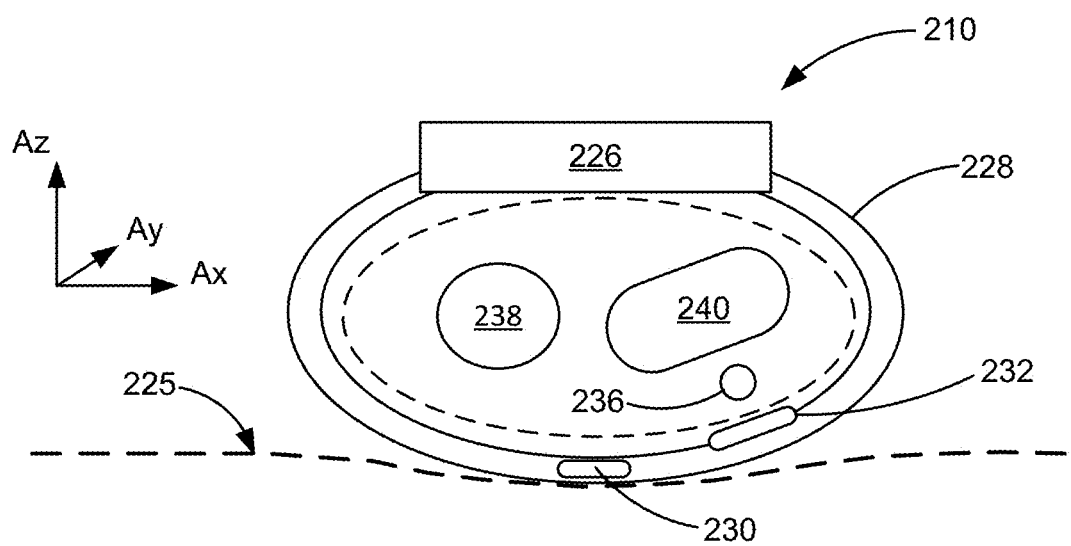
FIG. 10 is a schematic side view of a wrist-worn blood pressure measurement device held in contact with a user's chest according to embodiments of the present invention.

FIG. 10 shows a schematic side view of the wrist-worn device 210 held in contact with a user's chest 225, in accordance with many embodiments. When the wrist-worn device 210 is held in contact with a user's chest, SCG data is generated. When the wrist-worn device 210 is not held in contact with a user's chest, BCG data is generated. The wrist-worn device 210 includes a main unit 226, a wrist-worn elongate band 228, an accelerometer 230, and a PPG sensor 232. The accelerometer 230 and the PPG sensor 232 are supported on the wrist-worn elongate band 228 and operatively connected with the main unit 226. The PPG sensor 232 is positioned and oriented to interface with a wrist 234 of the user when the device 210 is worn on the wrist 234. The main unit 226 includes circuitry and/or software for processing output from the accelerometer 230 and the PPG sensor 232 so as to measure a PIT and calculate one or more blood pressure values for the subject based on the PTT. In the illustrated embodiment, the PPG sensor 232 is located on the wrist-worn band 228 so as to be disposed to sense the arrival of the blood-pressure pulse within a radial artery 236 of the subject. Cross sections of the ulna bone 238 and the radius bone 240 of the subject are shown for reference. In described embodiments, the accelerometer 230 is oriented to measure accelerations in each of axes Ax and Ay (in the plane of the user's chest 225) and axis Az (which is perpendicular to the user's chest 225).

Figure 11:
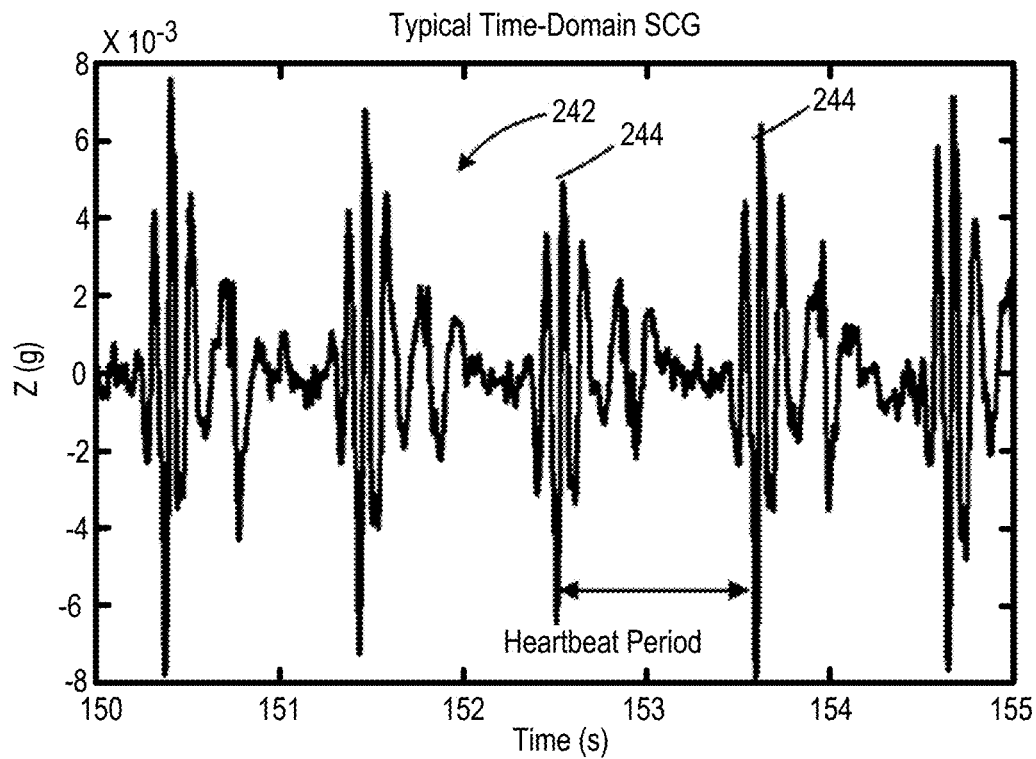
FIG. 11 is a typical time-domain trace of a measured Seismo-Cardiogram acceleration oriented normal to a user's chest surface according to embodiments of the present invention.

FIG. 11 shows a typical time-domain SCG trace 242 for acceleration measured in a direction normal to a user's chest surface, in accordance with many embodiments. The SCG trace 242 has localized peaks 244, which correspond to the opening of the aortic valve and associated ejection of blood into the aorta from the user's left ventricle. The SCG trace 242 can be processed to identify the localized peaks 244 and the associated time points at which the localized peaks occur, thereby identifying one or more time points for one or more ejections of blood from the left ventricle into the user's aorta. The identified one or more time points can be used in conjunction with one or more time points when the respective blood pressure pulses arrive at the wrist as detected by the PPG sensor 232 or alternatively via a pulse pressure sensor to calculate a PTT for the propagation of the blood pressure pulse from the left ventricle to the user's wrist. The calculated PTT can then be used to generate one or more blood pressure values for the user as described herein.

Figure 12:
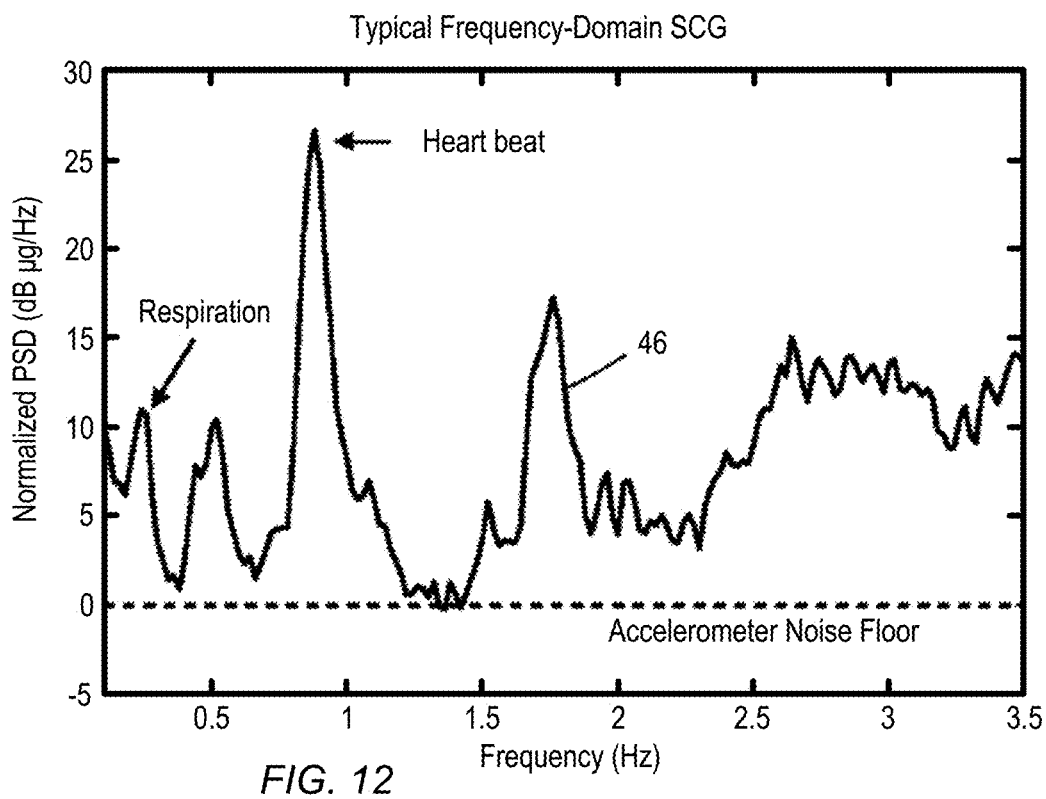
FIG. 12 is a typical frequency-domain Seismo-Cardiogram according to embodiments of the present invention.
Figure 13:
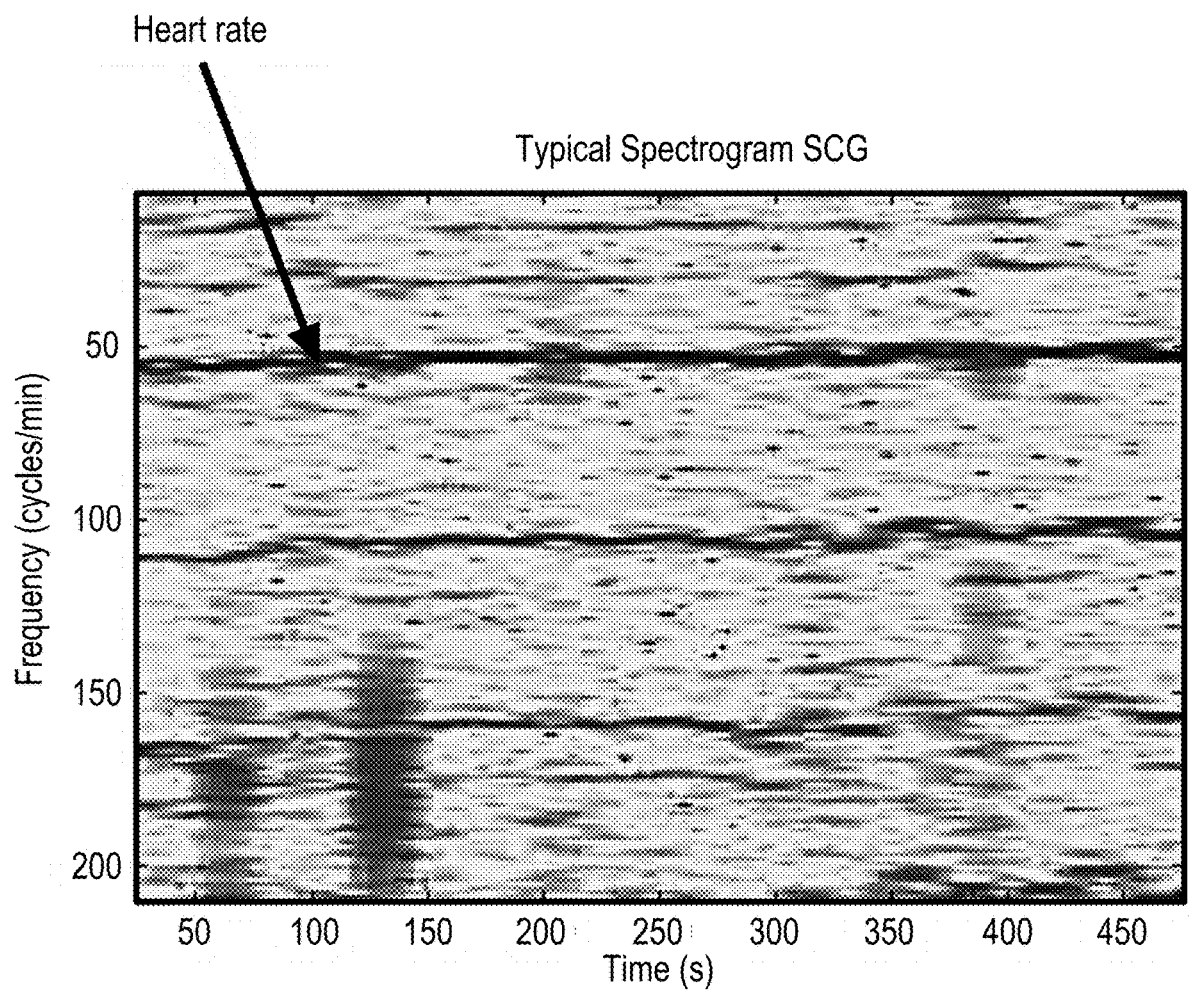
FIG. 13 is a typical spectrogram Seismo-Cardiogram according to embodiments of the present invention.

FIGS. 12 and 13 show additional plots that can be generated from output of the accelerometer 230. FIG. 12 shows a typical frequency-domain SCG 246 generated from the output of an accelerometer held in contact with a user's chest. The frequency-domain SCG, which can be used to identify heart rate for the user, which can be used to double check that the time points corresponding to the localized peaks 244 are separated by a time interval consistent with the identified heart rate. FIG. 13 shows a typical spectrogram SCG, which can also be used to identify heart rate for the user.

Figure 14:
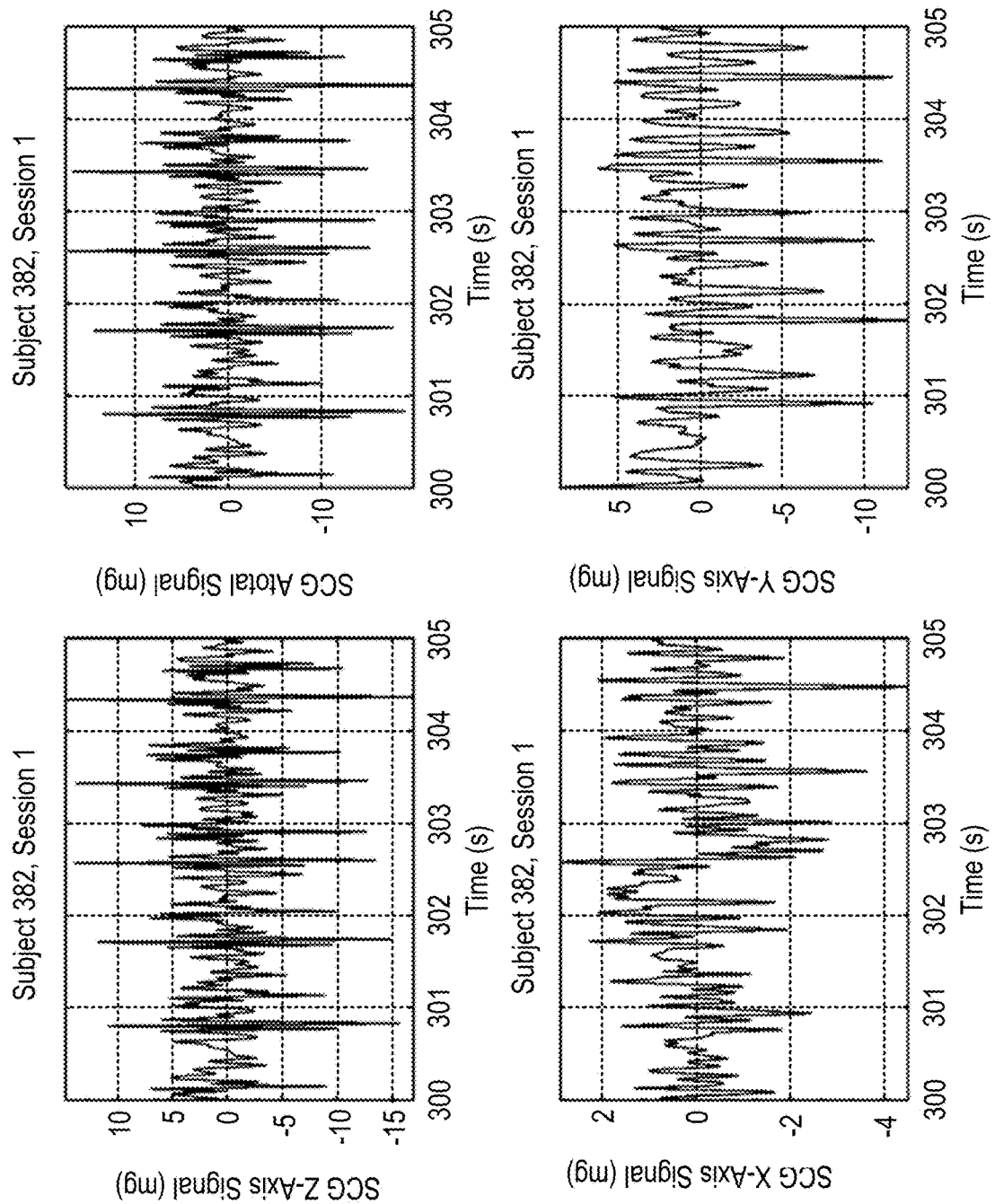
FIG. 14 shows x-axis acceleration, y-axis acceleration, z-axis acceleration, and vector-sum acceleration Seismo-Cardiogram plots according to embodiments of the present invention.

FIG. 14 shows example x-axis acceleration, y-axis acceleration, z-axis acceleration, and vector-sum acceleration SCG plots measured using an accelerometer held in contact with a subject's chest. Each of the z-axis acceleration (normal to the subject's chest) and the vector-sum acceleration (Atotal) exhibits clear acceleration peaks corresponding to respective ejections of blood from the subject's left ventricle. The y-axis acceleration (in plane of the subject's chest) is relatively less clear with respect to having acceleration peaks corresponding to respective ejections of blood from the subject's left ventricle. And the x-axis acceleration (also in plane with the subject's chest) is the least clear with respect to having acceleration peaks corresponding to respective ejections of blood from the subject's left ventricle.

Figure 15:
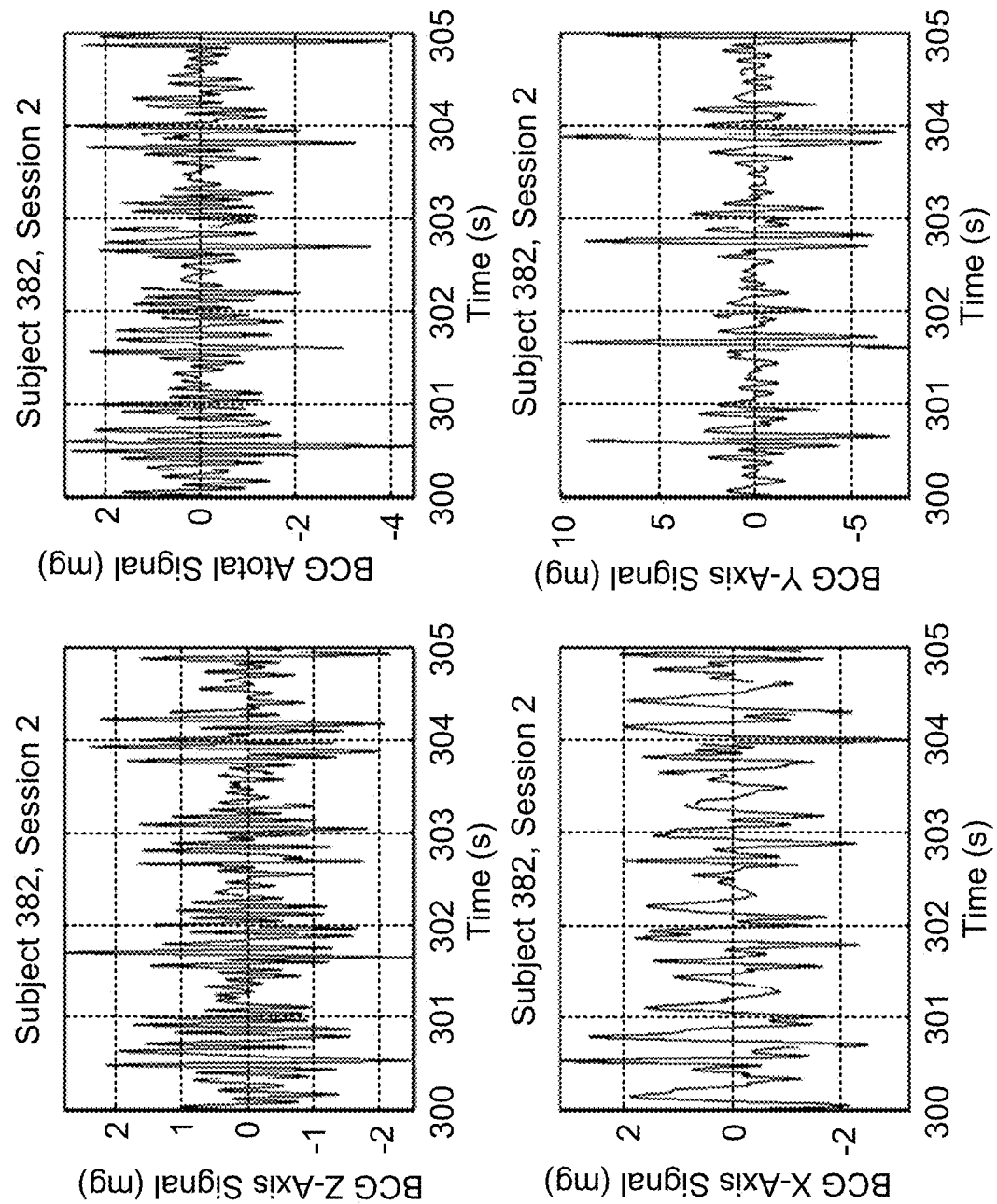
FIG. 15 shows x-axis acceleration, y-axis acceleration, z-axis acceleration, and vector-sum acceleration Ballisto-Cardiogram plots according to embodiments of the present invention.

FIG. 15 shows example x-axis acceleration, y-axis acceleration, z-axis acceleration, and vector-sum acceleration BCG plots measured using an accelerometer coupled to a wrist-worn device that is not held in contact with the subject's chest. These BCG plots show a different order with respect to which acceleration plots exhibit acceleration peaks corresponding to respective ejections of blood from the subject's left ventricle. Specifically, the y-axis acceleration BCG plot exhibits the most clear acceleration peaks corresponding to respective ejections of blood from the subject's left ventricle. The vector-sum acceleration (Atotal) BCG plot is the next most clear after the y-axis acceleration BCG plot. Finally, each of the x-axis acceleration and the z-axis acceleration BCG plots appear to be similarly exhibit the least clear acceleration peaks corresponding to respective ejections of blood from the subject's left ventricle. As is described herein with reference to FIG. 17, combinations of the component accelerations can be accomplished so as to exhibit greater signal variability, thereby having clearer acceleration peaks with respect to respective ejections of blood from the subject's left ventricle.

Figure 16:
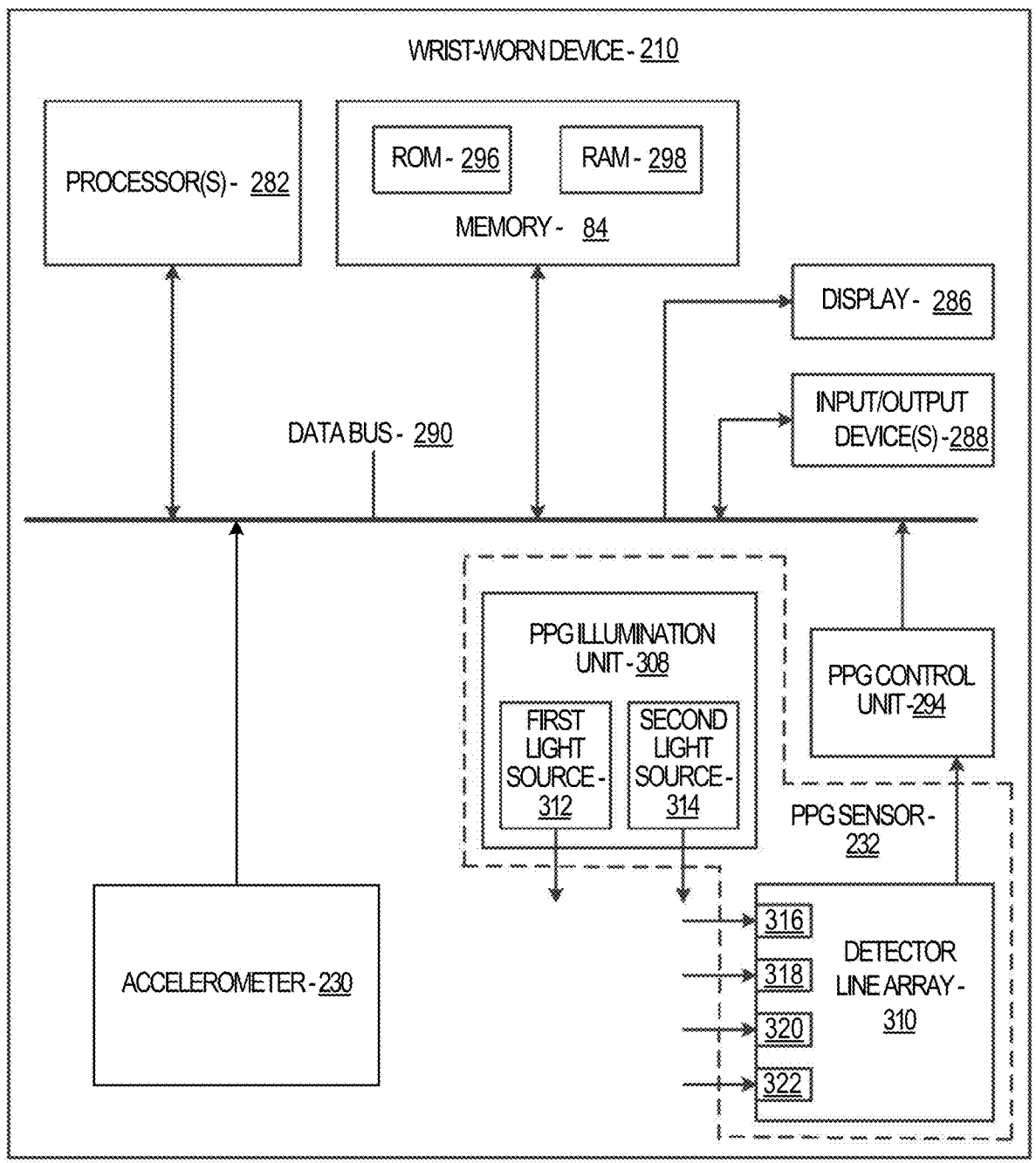
FIG. 16 is a schematic diagram of a wrist-worn blood-pressure measurement device according to embodiments of the present invention.

FIG. 16 schematically represents an embodiment of the wrist-worn device 210. In the illustrated embodiment, the wrist-worn device 210 includes one or more processors 282, memory 284, a display 286, one or more input/output devices 288, a data bus 290, the accelerometer 230, the PPG sensor 232, and a PPG sensor control unit 294. In many embodiments, the memory 284 includes read only memory (ROM) 296, and random access memory (RAM) 298. The one or more processors 282 can be implemented in any suitable form, including one or more field-programmable gate arrays (FPGA) or integrated circuits. The accelerometer 230 can be any suitable accelerometer (e.g., a three-axis low noise accelerometer).

The PPG sensor unit 232 includes a PPG illumination unit 308 and detector line array 310. The PPG illumination unit 308 includes two light sources 312, 314 which transmit light having different wavelengths onto the wrist. While any suitable wavelengths can be used, the first light source 312 generates a beam of light having a wavelength of 525 nm. The second light source 314 generates a beam of light having a wavelength of 940 nm. Any suitable number of light sources and corresponding wavelengths can be used and selected to provide desired variation in tissue penetrating characteristics of the light. The detector line array 310 can include any suitable number of light detectors. In many embodiments, the light detectors are disposed at a plurality of different distances from the light sources 312, 314 so that the detected light is associated with different mean penetration depths so as to enable detection of the arrival of the blood pressure pulse at different layers and/or within a layer of the wrist deeper than a layer sensed by a single light source and single detector PPG sensor. In the illustrated embodiment, the detector line array 310 includes four light detectors 316, 318, 320, 322, with each of the light detectors 316, 318, 320, 322 being disposed at a different distance from the light sources 312, 314. For example, the light detectors 316, 318, 320, 322 can be disposed at 2 mm, 3 mm, 4 mm, and 6 mm, respectively, from each of the light sources 312, 314. Signals generated by the light detectors 316, 318, 320, 322 are supplied to the PPG control unit 294, which includes an analog to digital converter to generate PPG sensor digital data that can be processed by the one or more processors 282 to determine the arrival of the blood pressure pulse to the wrist-worn device. The PPG control unit 294 controls activation of the light sources 312, 314, and can alternately illuminate the light sources 312, 314 at a frequency sufficiently high to enable combined assessment of the PPG sensor digital data generated by illumination of the wrist with the different wavelengths provided by the light sources 312, 314.

Measured acceleration data and the PPG sensor digital data can be transferred to, and stored in, the RAM 298 for any suitable subsequent use. For example, the data can be: 1) processed by the one or more processors 282 to determine PTTs and corresponding blood pressure values for the subject, 2) displayed on the display 286, and/or 3) output via the input/output devices 288 for any suitable purpose such as to a health care professional and/or a monitoring service. In many embodiments, the one or more processors 282 processes the acceleration data and PPG sensor digital data to generate trending data for a time period based on the one or more relative blood pressure values. Such trending data can be generated for any suitable time period, for example, for one or more days, one or more weeks, one or more months, and/or one or more years. One or more blood pressure values and/or associated trending data can be: 1) stored in the RAM 298, 2) displayed on the display 286, and/or 3) output via the input/output devices 288 for any suitable purpose such as to a health care professional and/or a monitoring service.

Figure 17:
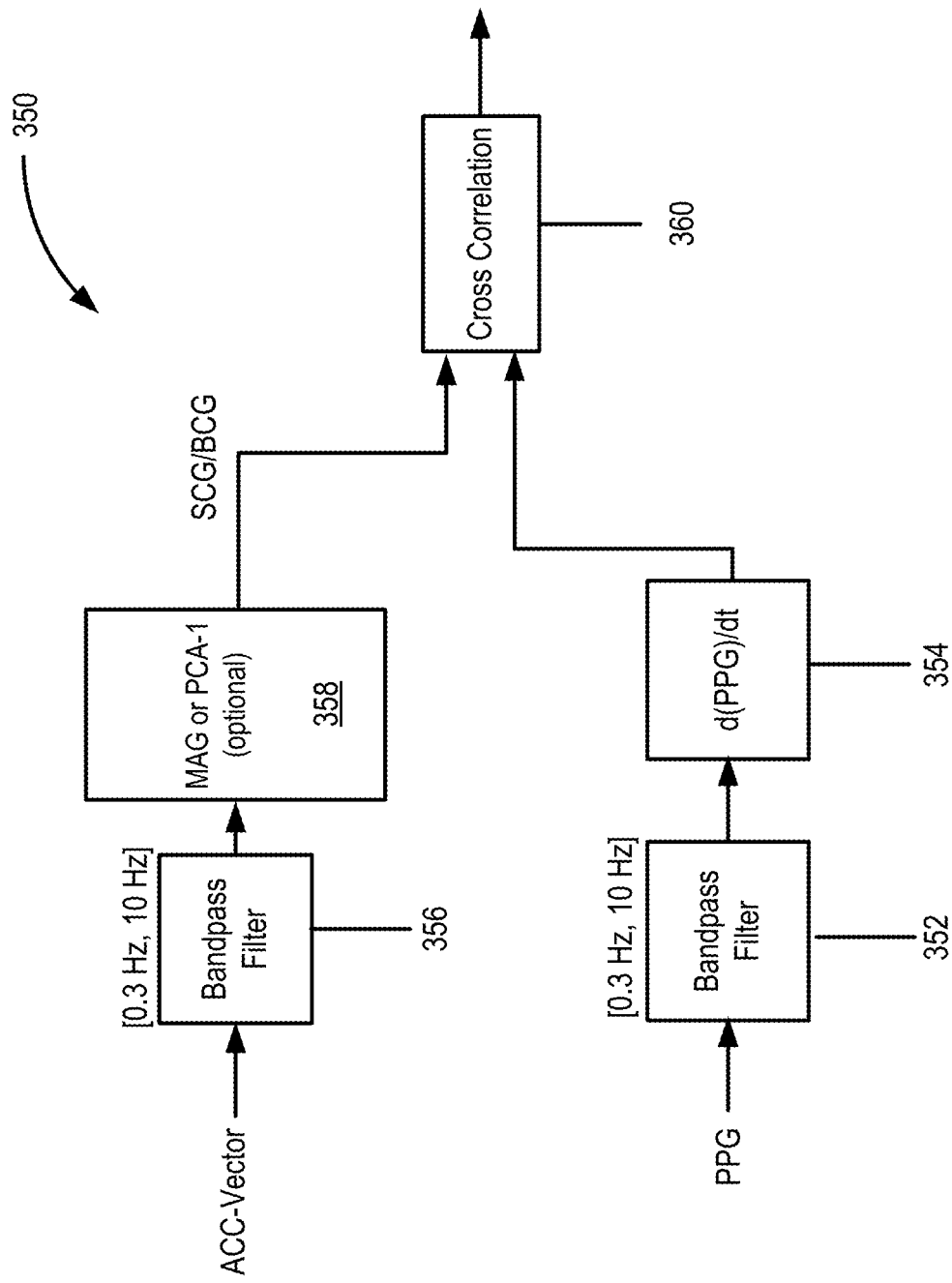
FIG. 17 is a schematic diagram of an approach for processing recorded acceleration data to identify when blood is ejected from the left ventricle of a user's heart according to embodiments of the present invention.

FIG. 17 illustrates an approach 350 for processing recorded acceleration data to identify when blood is ejected from the left ventricle of a user's heart, in accordance with many embodiments. In the approach 350, output from the PPG sensor 232 is processed with a suitable bandpass filter 352 (e.g., a bandpass filter that attenuates frequencies less than 0.3 Hz and frequencies greater than 10 Hz) to reduce noise. The filtered PPG sensor output is then differentiated with respect to time (act 354) so as to produce a signal that more clearly exhibits when the blood pressure pulse first arrives to the wrist prior to the arrival to the wrist of a reflection of the blood pressure pulse. In a similar fashion, the output from the accelerometer 230 (three component acceleration vector data, which varies over time) is also processed with a suitable bandpass filter 356 (e.g., a bandpass filter that attenuates frequencies less than 0.3 Hz and frequencies greater than 10 Hz) to reduce noise. The filtered acceleration vector data is then selectively combined so that the combined acceleration values exhibit greater variability with respect to ejections of blood from the subject's left ventricle, thereby exhibiting clearer acceleration peaks corresponding to respective ejections of blood from the subject's left ventricle. In one variation of the approach 350, a magnitude trace is calculated from the three component acceleration vector data (act 358). As illustrated in FIGS. 14 and 15 for each of the vector-sum acceleration data plots (Atotal) for both SCG and BCG, such a magnitude trace can exhibit clear acceleration magnitude peaks corresponding to respective ejections of blood from the subject's left ventricle. In another variation of the approach 350, a principal component analysis (PCA) can be performed (act 358) to identify a linear combination of the three components of the acceleration data that exhibits maximum acceleration variability, thereby increasing the likelihood that the identified combination will exhibit clear acceleration magnitude peaks corresponding to respective ejections of blood from the subject's left ventricle while allowing for flexibility in accelerometer orientation on the wrist. The principal component analysis can be accomplished by calculating the three-dimensional eigenvector associated with the maximum eigenvalue of the covariance matrix of the measured acceleration vector samples within a time window. The components of this eigenvector are used as the coefficients in the linear combination PCA-1 of the acceleration components. The resulting linear combination time samples can then be evaluated to identify peaks corresponding to respective ejections of blood from the subject's left ventricle. The PCA procedure is repeated for subsequent time windows of interest that contain measured acceleration data. In act 360, identified time points for the arrival of blood pressure pulses to the wrist are correlated with respective time points for the ejection of blood from the user's left ventricle (i.e., acceleration peaks identified in the combination of the three component acceleration vector data). For example, each time point for the arrival of a blood pressure pulse can be correlated with a respective time point for the ejection of blood from the left ventricle that falls within a preselected preceding time span (e.g., from 100 ms to 300 ms prior to the arrival of the blood pressure pulse to the wrist. Any suitable preceding time span can be used. And the preceding time span used can be customized to a particular subject to reflect individual variations in pulse wave velocity related characteristics, such as relative differences in arterial stiffness.

Figure 18:
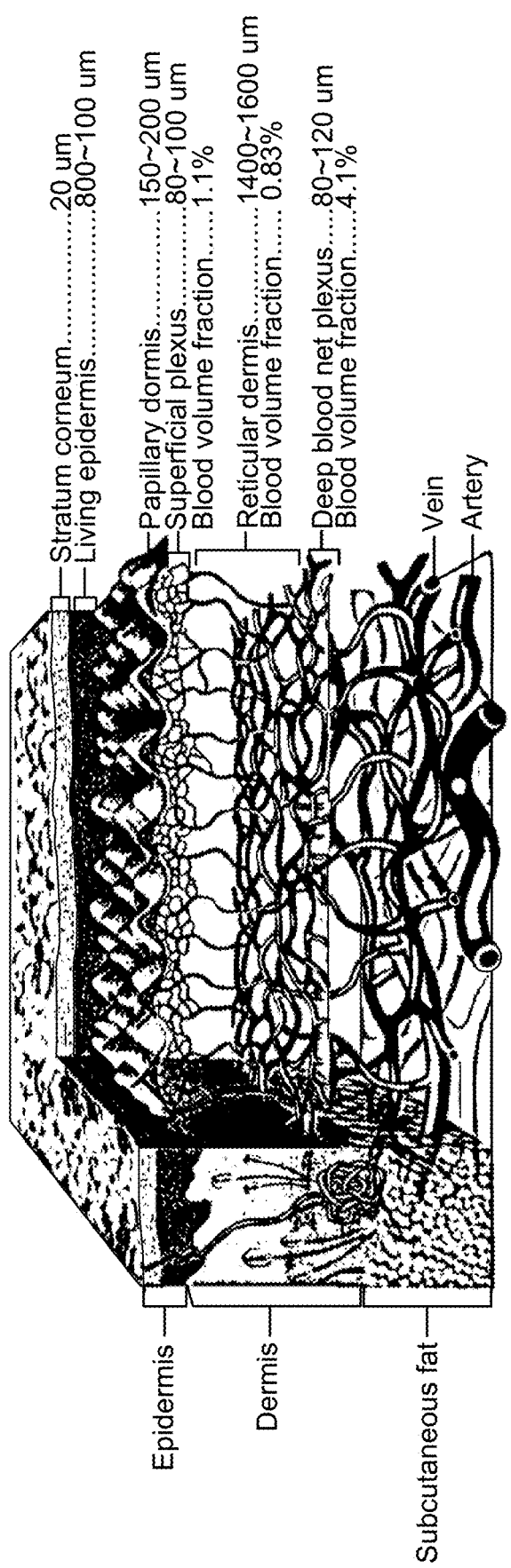
FIG. 18 illustrates a cross-section of tissue layers between a wrist skin surface and an underlying artery of a subject.

FIG. 18 illustrates subsurface layers of a subject. The illustrated layers include: 1) the stratum corneum (about 20 μm thick), 2) the living epidermis (80 to 100 μm thick), 3) the papillary dermis (150 to 200 μm thick), 4) the superficial plexus (80 to 100 μm thick with a blood volume fraction of about 1.10/), 5) the reticular dermis (1400 to 1600 μm thick with a blood volume faction of about 0.83%), and 6) the deep blood net plexus (80 to 120 μm thick with a blood volume fraction of about 4.1%). Upon arrival to the wrist, the blood pressure pulse arrives at the deep blood net plexus layer before propagating to the overlying layers. As vasomotion (vasodilation and vasoconstriction) plays an important role in regulating blood flow in arterioles and capillaries further downstream in the arterial tree, using the PPG sensor to detect the arrival of the blood pressure pulse in the deep blood net plexus layer may increase the strength of the correlation between blood pressure and PIT by reducing vasomotion induced variability of PTT in shallower layers more subject to vasomotion induced variation in pulse wave velocity of the blood pressure pulse.

Figure 19:
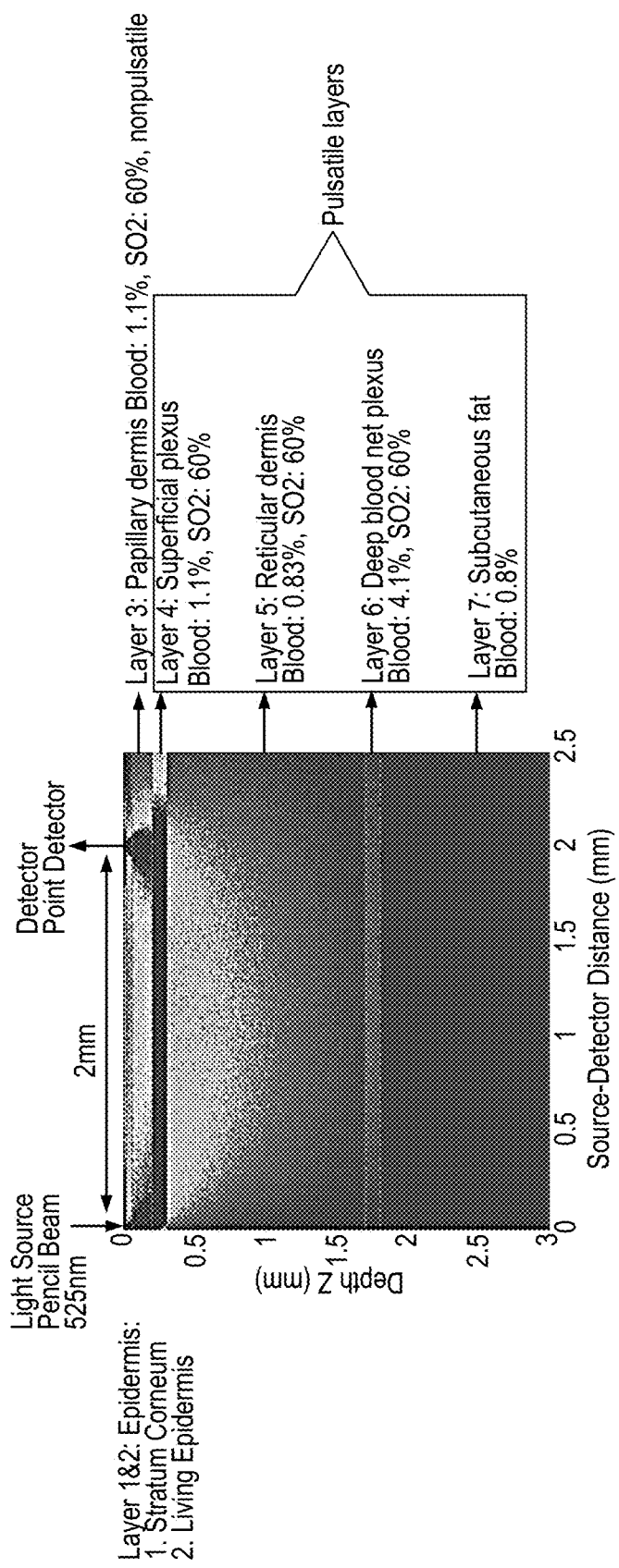
FIGS. 19-21 illustrate detection of different mean penetration depths of light emitted by a PPG sensor having returning light detectors disposed at different distances from each of two light sources of the PPG sensor according to embodiments of the present invention.
Figure 20:
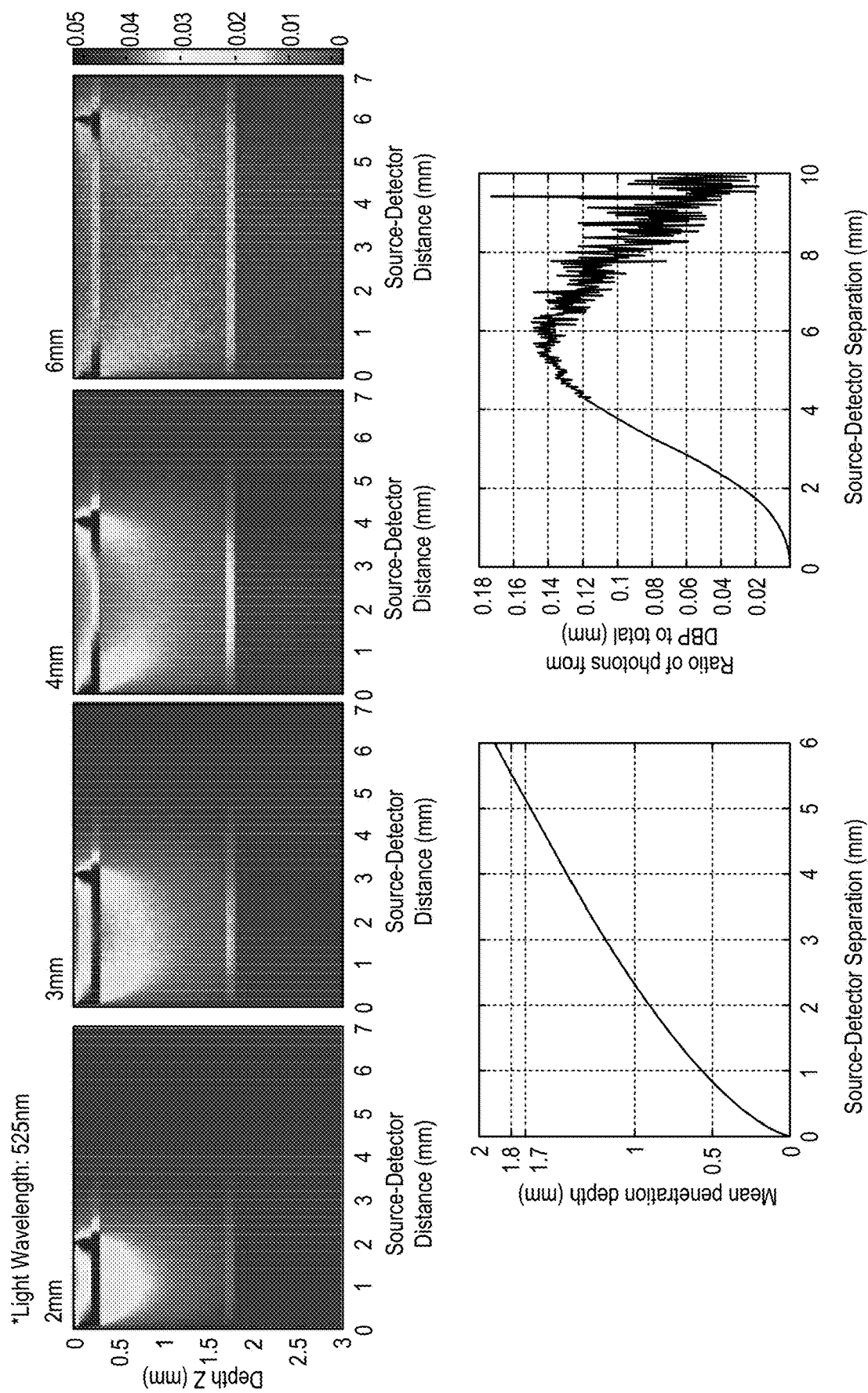
Figure 21:
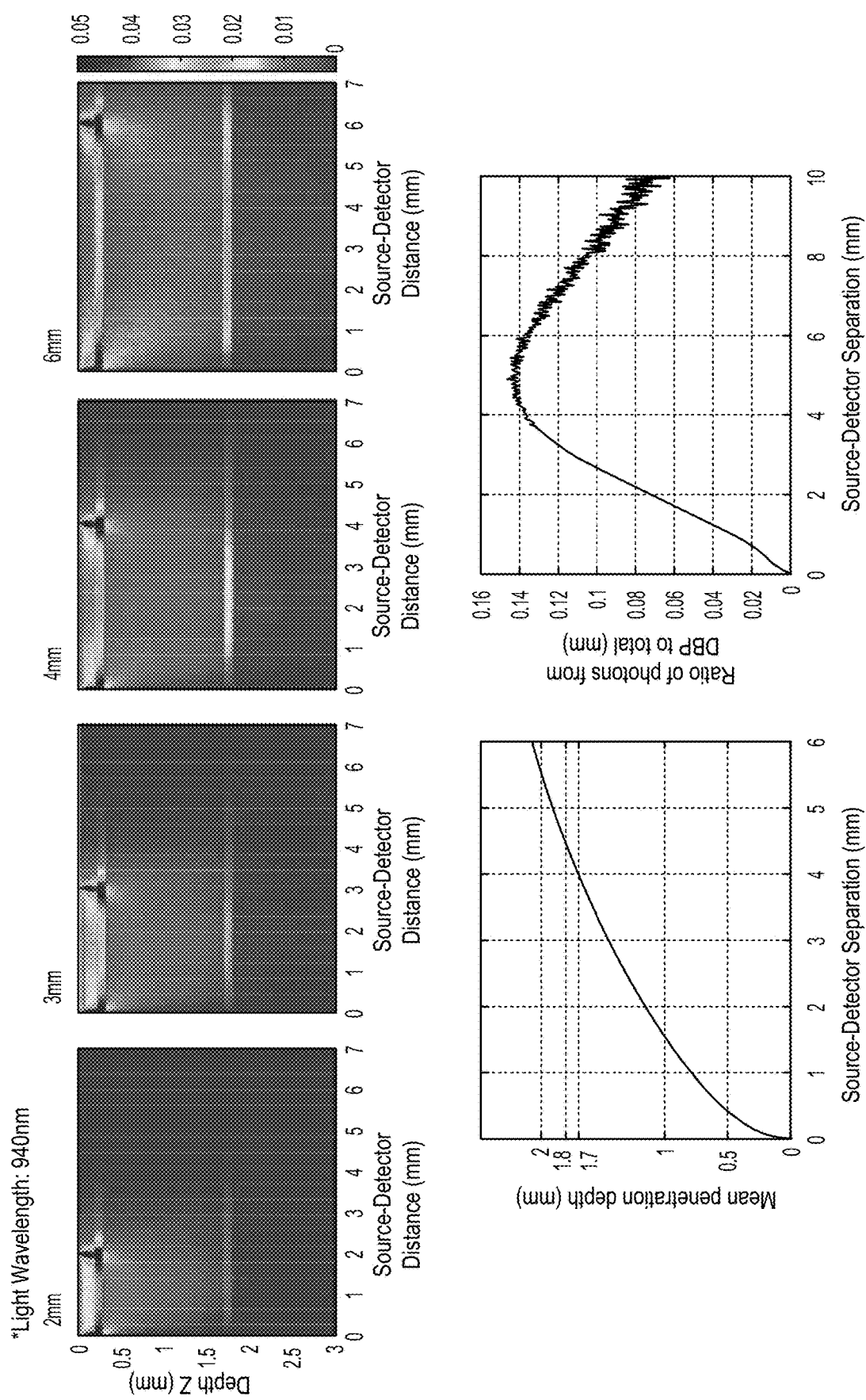
Figure 22:
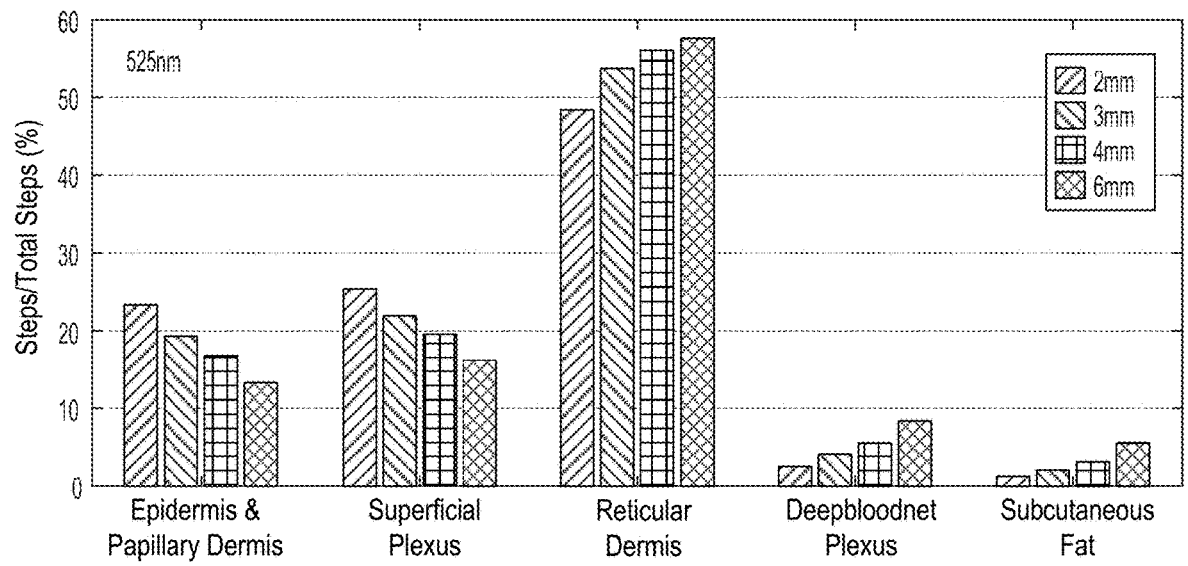
FIGS. 22-23 show relative contribution by subsurface layer to returning light detected by the light detectors disposed at different distances for two different light source wavelengths according to embodiments of the present invention.
Figure 23:
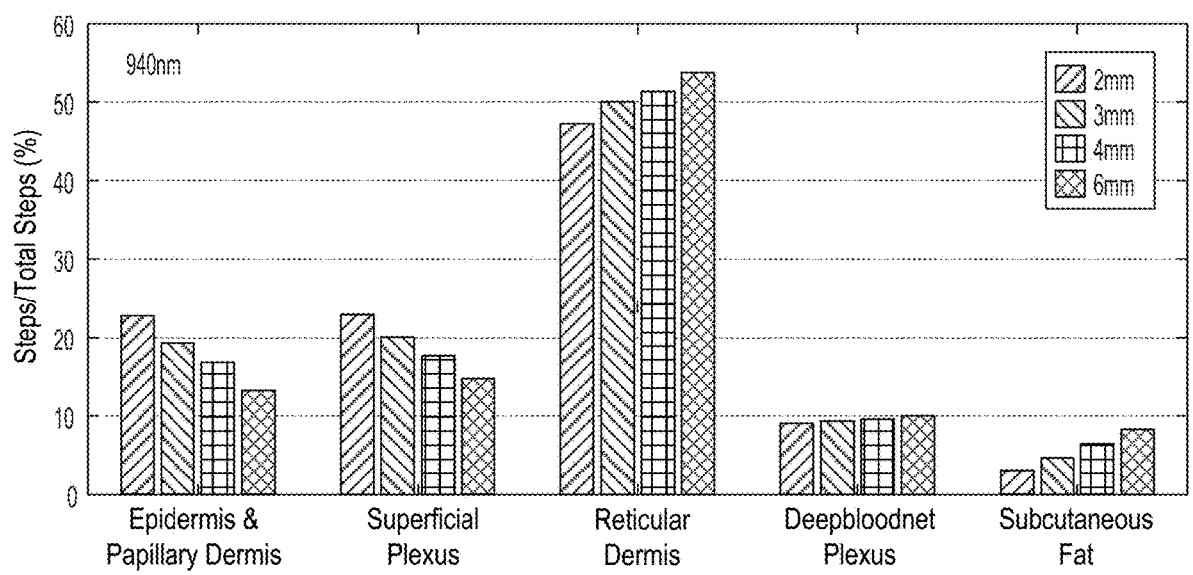
Figure 24:
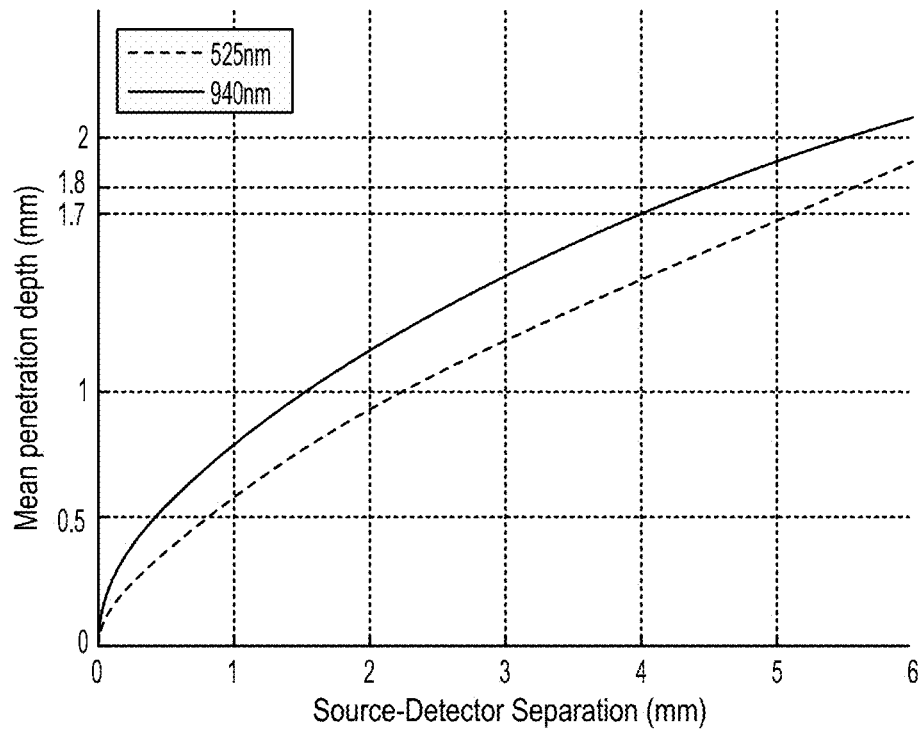
FIG. 24 illustrates variation of mean penetration depth as a function of source-detector separation for two different source light wavelengths according to embodiments of the present invention.
Figure 25:
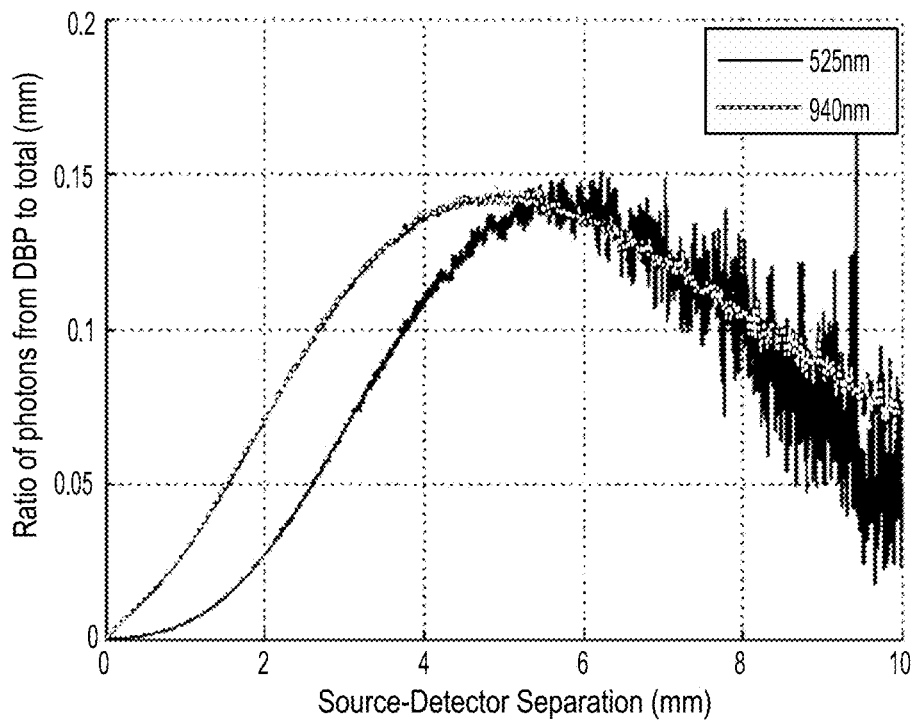
FIG. 25 illustrates variation of the ratio of photons from the deep blood plexus (DBP) layer as a function of source-detector separation for two different source light wavelengths according to embodiments of the present invention.

FIGS. 19 through 21 illustrate detection of different mean penetration depths of light emitted by a PPG sensor having returning light detectors disposed at different distances from each of two light sources of the PPG sensor, in accordance with many embodiments. FIG. 19 illustrates distribution of sensing depths for a combination of a 525 nm light source and a point detector disposed 2 mm from the 525 nm light source. FIG. 20 illustrates distributions of sensing depths for the combination of a 525 nm light source and point detectors disposed at 2 mm, 3 mm, 4 mm, and 6 mm from the 525 nm light source, as well as corresponding graphs of mean penetration depth and ratio of photons from the deep blood net plexus layer to the total detected returned light as a function of source-detector separation. FIG. 21 illustrates distributions of sensing depths for the combination of a 940 nm light source and point detectors disposed at 2 mm, 3 mm, 4 mm, and 6 mm from the 940 nm light source, as well as corresponding graphs of mean penetration depth and ratio of photons from the deep blood net plexus layer to the total detected returned light as a function of source-detector separation. FIGS. 22 and 23 show contribution of the total detected returned light for each layer for each wavelength and source-detector separation. FIGS. 24 and 25 show combined graphs corresponding to the graphs of FIGS. 20 and 21.

Using the data illustrated in FIGS. 19 through 25, the signals from the detectors 116, 118, 120, 122, 316, 318, 320, 322 generated for each of the light wavelengths generated by the light sources 112, 114, 312, 314 can be processed to detect arrival of the blood pressure pulse within a selected layer (e.g., with the deep blood net plexus layer). For example, arrival of the blood pressure pulse within the reticular dermis layer can be detected first due to the large percentage of the returning light incident on the detectors 116, 118, 120, 122, 316, 318, 320, 322 that returns from the reticular dermis layer. Once the arrival time to the reticular dermis layer is determined, the signals during a suitable time interval prior to the arrival time to the reticular dermis layer can be combined and/or processed to focus attention on detecting the earlier arrival of the blood pressure pulse to the deep blood plexus layer. Typically, infrared (e.g., 940 nm wavelength) light penetrates deeper into the skin compared to visible light such as green (e.g., 525 nm wavelength) or red (e.g., 660 nm wavelength). Hence, a PPG waveform recorded from infrared light corresponds to light reflected from deeper blood vessels, while a PPG waveform recorded from green light corresponds to light reflected from capillaries near the skin surface. Since the blood pulse arrives at deeper blood vessels earlier than capillaries near the skin surface, the blood pulse appears in the infrared PPG before the green PPG at the same location (e.g., on the wrist). A cross correlation of infrared and green PPG signals can be used to determine the relative delay between the arrival of the blood pulse at deeper blood vessels and the arrival of the blood pulse at capillaries near the skin surface.

The PPG signal can first be filtered in one of several ways, for example with a low-pass filter or with a regression filter. The pulse arrival can be detected as the peak of the amplitude of the PPG signal, or the "zero crossing point". Alternatively, the PPG signal can be differentiated with respect to time and the differentiated signal used to determine a pulse arrival time. This signal processing can be performed on single pulses, leading to PTTs for each heartbeat. Or, the processing can be performed on signals that are an average from more than one pulse. One multi-beat averaging method is to first transform the signals (ICG or ECG, and also PPG) into the frequency domain using a Fourier Transform. Then a cross-correlation between the two transformed signals will give a PTT value.

Figure 26:
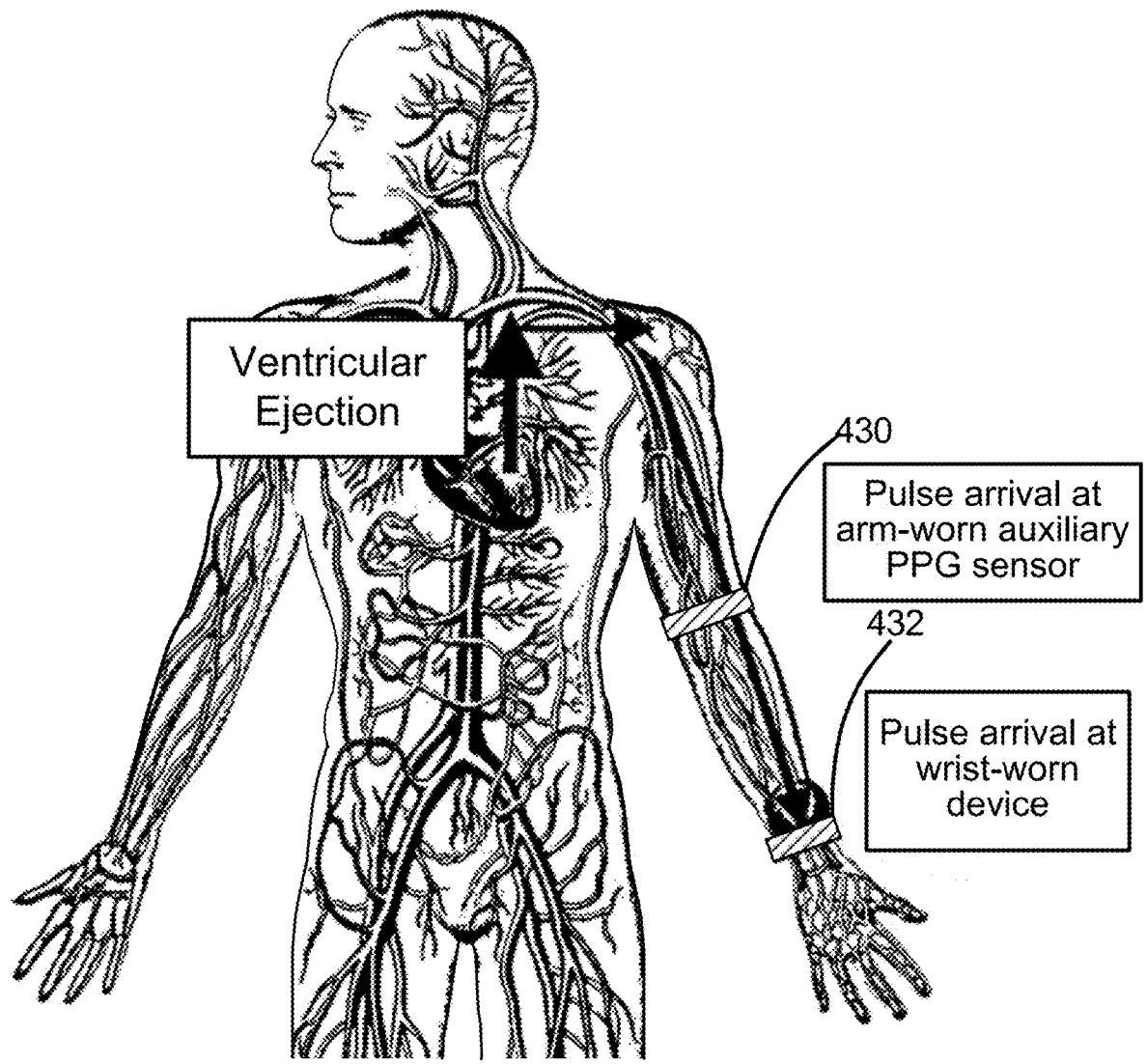
FIG. 26 illustrates a propagation path of a blood pressure pulse from ejection from the left ventricle past an auxiliary PPG sensor to a wrist on which a wrist-worn blood-pressure measurement device is worn according to embodiments of the present invention.

FIG. 26 illustrates another approach for measuring a PTT that can be used to generate one or more blood pressure values for a subject. The PTT measured in this approach is for the propagation of a blood pressure pulse from an arm-worn auxiliary device 430 to arrival at a wrist-worn device 432. The auxiliary device 430 and the wrist-worn device 432 can use any suitable approach for detecting the arrival of the blood-pressure pulse, such as via a PPG sensor as described herein.

Figure 27:
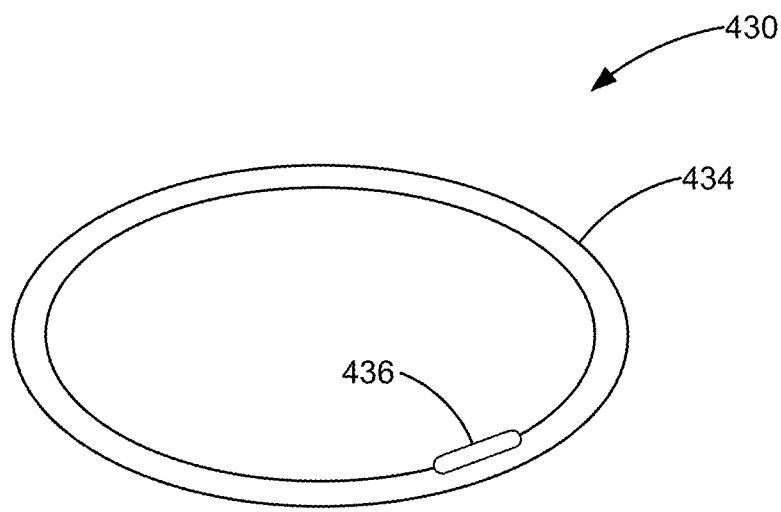
FIG. 27 is a schematic side view of an arm-worn auxiliary PPG sensor for a wrist-worn blood-pressure measurement device according to embodiments of the present invention.
Figure 28:
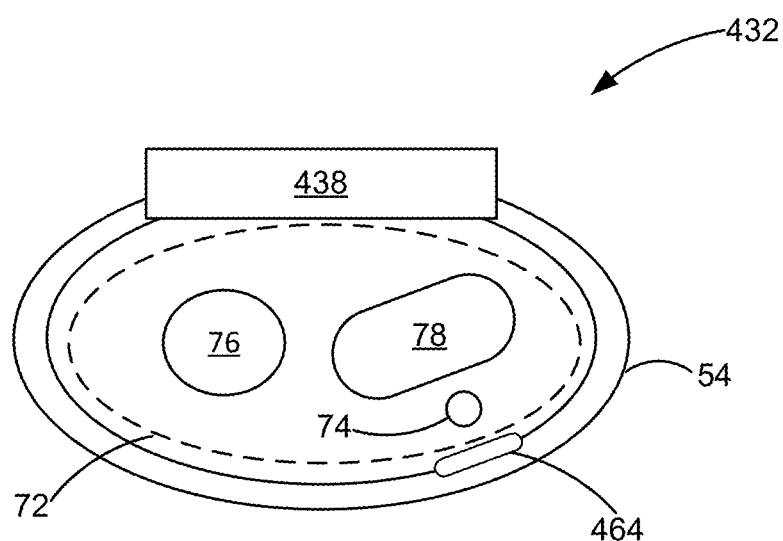
FIG. 28 is a cross-sectional view of another wrist-worn blood-pressure measurement device that can be used with the auxiliary PPG sensor of FIG. 27 according to embodiments of the present invention.

FIGS. 27 and 28 show side views of the auxiliary device 430 and the wrist-worn device 432. The auxiliary device 430 includes an arm-worn elongate band 434 and an auxiliary PPG sensor 436 coupled to the band 434. The auxiliary device 430 can include one or more reference features or marks to as to enable reliable positioning and/or orientation of the auxiliary PPG sensor 436 relative to a selected underlying artery so as to detect arrival of the blood pressure pulse within the selected underlying artery. The wrist-worn device 432 can be configured similar to any of the wrist-worn devices described herein with respect to the PPG sensor 464 and can have a main unit 438 that is configured similar to any of the main units described herein with respect to all relevant functionality thereof.

Figure 29:
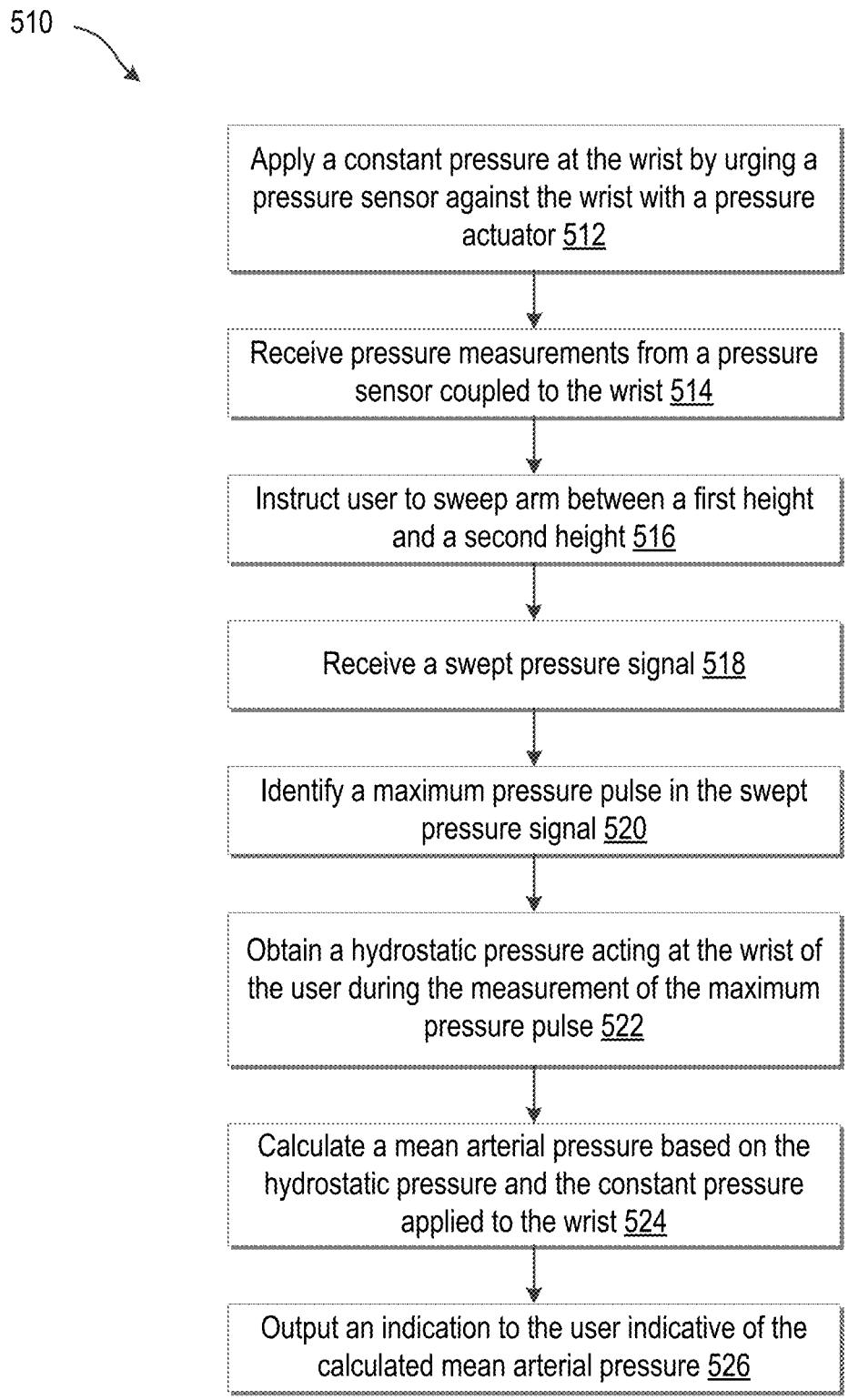
FIG. 29 illustrates a method for calculating a mean arterial pressure of a user according to embodiments of the present invention.

FIG. 29 illustrates an exemplary method 510 for calculating a mean arterial pressure with a wrist-worn pressure sensor. At step 510, after the wrist-worn device is coupled with a user's wrist, a constant pressure may be applied to the wrist with a pressure sensor coupled with a pressure actuator. Pressure measurements from the wrist may be received from the pressure sensor once it is urged against the wrist 514. The user may then be instructed to sweep their arm between a first height and a second height 516 to vary the hydrostatic pressure experienced at the wrist. As the user sweeps their arm from the first height to the second height, a swept pressure signal may be received from the pressure sensor where the pressure pulses vary in amplitude due to the changes in hydrostatic pressure experienced at the wrist as the user moves their arm. The swept pressure signal may be analyzed to identify a maximum pressure pulse in the swept pressure signal 520. A hydrostatic pressure associated with the maximum pressure pulse is obtained 522 after identifying the maximum pressure pulse. A mean arterial pressure may then be calculated 524 based on the obtained hydrostatic pressure and the constant pressure applied to the wrist. An indication may then be outputted 526 to provide a user an indication of the obtained mean arterial pressure. It will be appreciated however that a PPG sensor of the wrist-worn devices described above may alternatively be utilized, instead of a pressure sensor, to provide optical volume waveform signals, wherein a maximum volume waveform signal is identified to determine the mean arterial pressure according to FIG. 29.

The exemplary method 510 utilizes the changes in hydrostatic pressure for applanation of an artery of the user. In many embodiments, the method 510 may be used for applanation of the radial artery or other superficial artery with sufficient bony support of a user. As the wrist changes in height relative to the heart of the user, the amount of hydrostatic pressure will vary and apply different amounts of pressure at the wrist of the user for applanation of the target artery. This exemplary method 510 for calculating mean arterial pressure is counterintuitive as many prior non-invasive methods of measuring and monitoring blood pressure teach away from arm movement during blood pressure monitoring. More specifically, many prior methods require or suggest that a user maintain their arm in preferred position throughout the measurement and/or monitoring of the user's blood pressure. Further, some methods of monitoring or measuring blood pressure may require wrist harnesses that lock the user's wrist in a preferred orientation while the measurements are taken. A method where the user may obtain blood pressure measurements and/or monitoring without the need for bulky wrist harnesses may provide a more convenient method in which users can easily measure their own arterial pressure on the go and outside of a clinic setting.

In many embodiments, after the user has coupled the device to their wrist, a constant pressure may be applied 512 by urging a pressure sensor against the wrist of the user. The constant pressure may be applied by a number of different ways. For example, wrist-worn device straps may be manually tightened (e.g., a Velcro strap, adjustable strap, or the like etc.) or mechanically tightened (e.g., through a ratcheting mechanism, or the like, etc.). The straps can be tightened using micro-linear actuator, or electroactive polymer (artificial muscles). In many embodiments a pressure actuator may be used to urge the pressure sensor against the wrist of the user. For example, solenoids, linear actuators, fluid bladders or the like may be coupled with a pressure sensor and actuated to urge the pressure sensor against the wrist and may also be actuated to reduce an amount of pressure applied.

In some embodiments, the applied constant pressure could be selected in the range 80-120 mmHg, which is close to the range of mean arterial pressures of interest. The use of applanation tonometry to determine mean arterial pressure requires that the transmural pressure equals zero, P_transmural=0. The transmural pressure acting across an arterial wall is defined as the difference between the internal pressure and external pressure, P_transmural=P_internal−P_external. Under the assumption of negligible resistance from the aorta to large peripheral arteries, the internal pressure P_internal at a peripheral artery is the sum of the central aortic blood pressure and the hydrostatic pressure at the peripheral artery relative to the aorta. Hence, the internal pressure of a peripheral artery that is below the aorta is greater than the blood pressure of the aorta; similarly, the internal pressure of a peripheral artery that is above the aorta is less than the blood pressure of the aorta. For a constant external pressure, the transmural pressure is largest when the peripheral artery is at its lowest point and smallest when the peripheral artery is at its highest point. When the artery is at its lowest point, the transmural pressure is typically greater than zero. As the artery is raised from its lowest point, the transmural pressure decreases until it reaches zero and begins to become negative. It follows that for a constant external pressure P_external, the transmural pressure will reach zero at a height that depends on the central aortic blood pressure. As the central aortic blood pressure increases, the transmural pressure equals zero at increasing peripheral artery heights. Conversely, as the central aortic blood pressure decreases, the transmural pressure equals zero at decreasing peripheral artery heights. For example, a constant pressure may be applied at the wrist such that transmural pressure at the wrist is positive when the user's arm is at a resting position (e.g., by the user's side when standing). The constant pressure may also be configured to allow the transmural pressure to turn negative after the user raises their arm a height relative to the user's heart. With such a configuration, an applanation of a target artery where the arterial wall is flattened and transmural pressure turns to zero. Here, the arterial pressure is perpendicular to the surface may occur at a height between the resting position where transmural pressure is positive state and the raised position where transmural pressure is negative. At the this height of the wrist, the hydrostatic pressure acting on the user's wrist and the constant pressure applied at the wrist may applanate the artery such that the arterial pressure is the only pressure detected by the pressure sensor (e.g., a desired applanation).

Figure 29A:
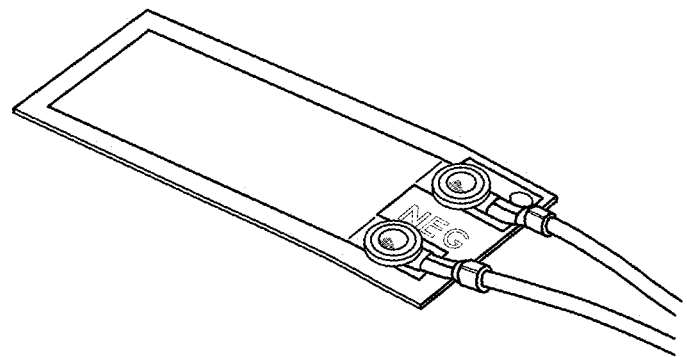
FIG. 29A shows a piezoelectric film sensor according to embodiments of the present invention.
Figure 29B:
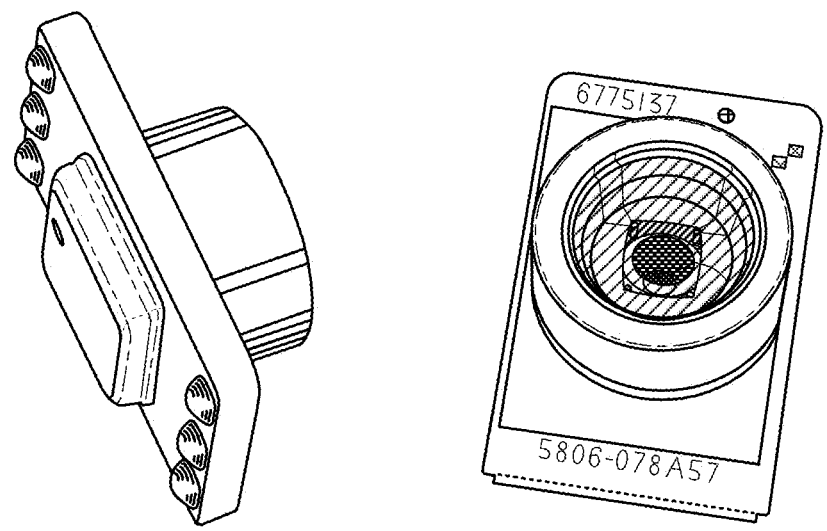
FIG. 29B shows a piezoelectric pressure sensor according to embodiments of the present invention.

Once the pressure sensor is coupled with the wrist of the user, a pressure signal/measurement may be received from the pressure sensor 514. The received pressure signal may correspond to an arterial pressure of the user. In some embodiments, the pressure sensor may be a capacitive pressure sensor, a piezoelectric film pressure sensor, a piezoresistive microelectromechanical system (MEMS) pressure sensor, bladder fluid or gas pressure sensor, or the like. FIG. 29A shows an exemplary piezoelectric film sensor that may be used with embodiments of the present invention described herein. FIG. 29B shows an exemplary piezoresistive pressure sensor that may be used with embodiments of the present invention described herein.

In some embodiments a piezoelectric film pressure sensor may be preferable as the film may be thin and may better conform to the contours of the user's wrists. When using a piezoelectric film pressure sensor, some embodiments may actuate the piezoelectric film pressure sensor with a fluid bladder. A fluid bladder pressure sensor identifying an applied pressure by the fluid bladder may be used to measure static pressure while the piezoelectric film pressure sensor measures dynamic pressure. The piezoelectric film measures the dynamic pressure oscillations from the artery, while the fluid bladder pressure sensor measures the static applied pressure from the fluid bladder.

In some embodiments a piezoresistive may be preferable as the film may also conform to the contours of the user's wrist and may further measure a static and dynamic pressure.

In many embodiments, an array of pressure sensors may be used to ensure that at least one of the pressure sensors of the array is positioned at a preferable location relative the target artery of the user. For example, in some embodiments, a 12×1 array, two 12×1 arrays, a 3×4 array, two 3×4 arrays, or the like of pressure sensors may be applied transverse to the radial artery of the wrist. In some embodiments, a single pressure actuator may be used to urge the entire array of sensors against the target artery. In other embodiments, multiple pressure actuators may be used to urge portions of the array of sensors against the target artery. For example, some embodiments of the wrist-worn device may have each pressure sensor coupled with a pressure actuator such that each individual pressure sensor may be individually urged against and away from the wrist by a desired amount and at different times. Further details of exemplary devices are discussed further below.

The user may be instructed to sweep their arm between a first height and a second height 516. The first height and second heights may be, for example, a resting position where the user's arm rests against their side when standing and a raised position where the user's arm is raised above their head. In many embodiments, it may be preferable to instruct that the user slowly sweep their hand to different heights so that a plurality of pressure pulses may be measured at different heights. Further, while not essential, it may be preferable to instruct the user to maintain their arm in an extended position or straight orientation (e.g., where the elbow is locked) so that a wrist height measurement, relative to the user's shoulder, may be calculated using an angle of the arm and a shoulder-to-wrist length.

As the user moves their arm to different heights, a swept pressure signal may be received 518. The swept pressure signal may include a plurality of pressure pulses that vary in amplitude due to changing hydrostatic pressure experienced at the wrist at the different heights.

As discussed above, a desired applanation of a target artery where the arterial wall is flattened and the arterial pressure is perpendicular to the surface may occur at a desired height between the first wrist height (e.g., resting position where the arm is positioned by the user's side) where the transmural pressure is positive and a second wrist height (e.g., a raised position above the resting position) where the transmural pressure is negative or vice-versa. At this desired height where the transmural pressure is zero, the hydrostatic pressure acting on the user's wrist and the constant pressure applied at the wrist may applanate the artery such that the arterial pressure stress is measured by the pressure sensor. Accordingly, in a height swept pressure signal with a plurality of pressure pulses measured at different heights, the desired applanation of the target artery is associated with the pressure pulse with the largest amplitude (i.e., "maximum pressure pulse"). Thus, after receiving the swept pressure signal 518, a maximum pressure pulse in the swept pressure signal is identified 520 as it is associated with the desired applanation of the target artery and a corresponding hand height, location, and/or orientation may be recorded for calculating a hydrostatic pressure.

To calculate a mean arterial pressure 524, the applied constant pressure and a hydrostatic pressure acting on the wrist during the measurement of the maximum pressure pulse are obtained. The mean arterial pressure (MAP) may be calculated by the following formula:

$$MAP = P_{applied} - P_{hydrostatic}, \quad (8)$$

where: $P_{applied}$ is the constant pressure applied at the wrist and $P_{hydrostatic}$ is the hydrostatic pressure acting on the wrist during the measurement of the maximum pressure pulse.

$P_{hydrostatic}$ may be calculated by:

$$P_{hydrostatic} = \rho g h, \quad (8a)$$

where: $\rho$ is the density of blood, g is the gravitational constant, and h is the height difference between the heart and the wrist of the user ("heart-to-wrist height"). The average density of blood is approximately 1060 kg/m³. The gravitational constant is approximately 9.8 m/s². The height difference, h, may be defined as:

$$h = \text{Height}_{heart} - \text{Height}_{wrist}, \quad (9)$$

where h is obtained in centimeters (cm) and where MAP is outputted in mmHg, equation (1) may be rewritten to:

$$MAP(mmHg) = Pressure_{applied} - 0.78\left(\frac{mmHg}{cm}\right) * h(cm), \quad (10)$$

Accordingly, MAP may be calculated by obtaining the constant pressure applied at the wrist and by obtaining the heart-to-wrist height of the user that is associated with the measurement of the maximum pressure pulse.

Figure 30:
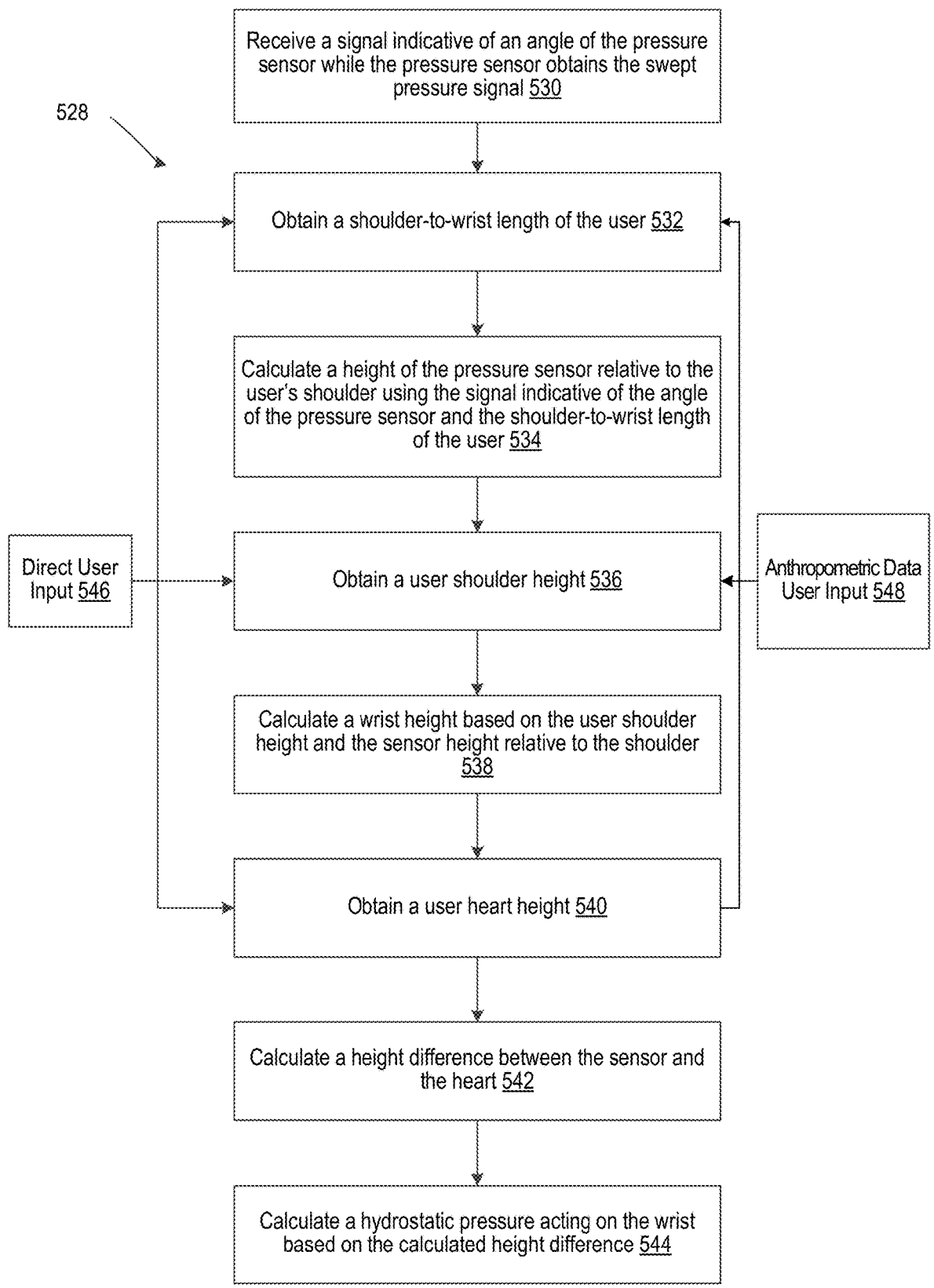
FIG. 30 illustrates a method for determining a hydrostatic pressure acting on the wrist of a user according to embodiments of the present invention.

FIG. 30 illustrates an exemplary method 528 of calculating the hydrostatic pressure at the wrist 522. At step 530, a signal indicative of an angle of the pressure sensor may be received while the pressure sensor obtains the swept pressure signal. A shoulder-to-wrist length of user may be obtained 532. A height of the sensor relative to the user's shoulder may be calculated 534 using the signal indicative of the angle of the pressure sensor and the obtained shoulder-to-wrist length. A height of the user's shoulder may then be obtained 536 for use in calculating a wrist height 38 based on the shoulder height and the sensor height relative to the shoulder. A user's heart height may then be obtained 540. A height difference between the pressure sensor/wrist and the heart may then be calculated 542 based on the obtained user heart height 540 and the calculated wrist height 538. Using the calculated height difference, a hydrostatic pressure acting on the wrist at the height of the sensor may be calculated 544 and used to calculate the MAP 524 (e.g., using equation 10).

In some embodiments, an accelerometer may be coupled with the wrist-worn device and may output an angle of the pressure sensor 530 while receiving the swept pressure signal. The received angle information 530 may be used with an obtained shoulder-to-wrist height 532 to identify a height of the pressure sensor and wrist of the user relative to the shoulder of the user. For example, a shoulder-to-wrist height (Height$_{shoulder-to-wrist}$) may be calculated with the following:

$$\text{Height}_{shoulder-to-wrist} = l_{shoulder-to-wrist} * \sin \theta_{wrist}; \quad (11)$$

where: $l_{shoulder-to-wrist}$ is the length of the shoulder to the wrist of the user, and theta is the angle of the wrist/pressure sensor relative to horizontal identified by the accelerometer.

Optionally, if the accelerometer returned an angle, $\varphi$, of the pressure sensor 530 relative to vertical (e.g., where an arm raised straight up returns an angle of 0° and an arm position straight down returns an angle of 180°), shoulder-to-wrist height may be calculated with the following:

$$\text{Height}_{shoulder-to-wrist} = l_{shoulder-to-wrist} * \cos \varphi_{wrist}. \quad (12)$$

The length of the shoulder to the wrist of the user may be obtained 532 directly from a user input 546 for use in equation (11) or (12). For example, a user interface may be provided that requests the user to input a shoulder-to-wrist length. In response to a user input indicative of the shoulder-to-wrist length, the device may store the received user input for use in equation (11) and/or (12).

In some embodiments of the invention, the user may input anthropometric data 548 and the length of the shoulder to the wrist of the user may be estimated based on the user inputted anthropometric data. For example, in some embodiments, a user may input a gender and a height. In further embodiments, other anthropometric data may be obtained such as a user's age, weight, ethnicity, etc. Based on received anthropometric data, shoulder-to-wrist length may be estimated. For example, in some embodiments, a shoulder-to-wrist length of a male user may be estimated as approximately 30%-36% of the user's inputted height, and in some embodiments preferably about 330%-34% of the user's inputted height and in further embodiments, even more preferably about 33.4%-33.5% of the user's inputted height. For some embodiments, a shoulder-to-wrist length of a female user may be estimated as approximately 31%-37% of the user's inputted height, and in some embodiments, even more preferably about 33%-35% of the user's inputted height, and in further embodiments, even more preferably about 33.3%-34.5% of the user's inputted height.

Thereafter, a user's wrist height ($Height_{wrist}$) may be calculated 538 by obtaining a user shoulder height 536 with the following:

$$Height_{wrist} = Height_{shoulder} + Height_{shoulder\text{-}to\text{-}wrist} \quad (13)$$

Optionally, equation (13) may be substituted into equation (9) to provide:

$$h = Height_{heart\text{-}wrist} = Height_{heart} - (Height_{shoulder} + Height_{shoulder\text{-}to\text{-}wrist}). \quad (14)$$

In a similar manner to receiving a shoulder to wrist length, a shoulder height may be requested and received through a user input 546 or may be estimated using received anthropometric data 548. For example, in some embodiments, a shoulder height of a male user may be estimated as approximately between 80%-84% of the user's height, and in further embodiments, preferably between about 81.5%-82.5% of the user's height, and even more preferably about 81.9%-82% of the users height. For a female user, a shoulder height may be estimated as approximately between 81.5%-83.5% of the user's inputted height, and in further embodiments, preferably between 82%-83% of the user's inputted height, and even more preferably about 82.4%-82.6% of the user's inputted height.

To calculate for $Height_{heart\text{-}wrist}$ using equation (13) or equation (14), a user heart height 540 may be obtained directly through user input 542 (user inputted and stored for subsequent use) or may be estimated based on anthropometric data inputted by the user 548 (e.g., gender, height, or the like). In some embodiments, a height of the user's heart may be estimated as approximately 70-75% of the user inputted height, in further embodiments, preferably about 72%-73% of the user inputted height and even more preferably about 72.5% of the user inputted height.

Once $Height_{heart\text{-}wrist}$ is obtained, a hydrostatic pressure acting on the wrist may be calculated 544 using equation (8a) and a MAP may be calculated 524 using equation (10).

After calculating an MAP for a user, the method 510 may then proceed to output an indication to the user that is indicative of the calculated MAP 526. The output may comprise the calculated MAP. Alternatively, the output may be a general indicator that indicates where the calculated MAP falls on a spectrum (e.g., good MAP, intermediate MAP, bad MAP). The output may be audio (e.g., a voice or other audio indicator) or visual. For example, the output may be outputted to a display of the device or LEDs may be illuminated to provide the indication. In some embodiments, the output may be communicated to a separate wearable device coupled with the wrist-worn blood pressure monitoring device. For example, in some embodiments, the wrist-worn blood pressure monitoring device may be coupled with a separate wrist-worn electronics device. The separate device may include a separate power source, processor, communications port, memory, and inputs/outputs, etc. In further embodiments, the output may be transmitted (e.g., wirelessly) to a mobile device of a user. For example, an indication of the calculated MAP may be transmitted to a smartphone, or other portable electronic device (e.g., tablets, PDAs, laptops, or the like) for recordation, analysis, and documentation.

In some embodiments, the wrist-worn blood pressure monitor may output or otherwise transmit received sensor signals (e.g., wrist angle, pressure signal, swept pressure signal or the like) to a separate device for further processing and recordation. This may be advantageous in reducing the processing power needed in the wrist-worn device, thereby allowing the device to have a smaller footprint and may allow the device to be operated for longer periods of time due to a lower power consumption. Further, by transmitting the data to a secondary device (e.g., watch, phone, tablet, or the like) on-board storage and battery requirements may be reduced, thereby further allowing the device to have a smaller footprint.

While generally discussed as instructing the user to actively, intentionally, and/or knowingly carry out the arm sweep for generating the swept pressure pulse, other embodiments may be passive where the pressure signals may be received throughout a period of time as the user carries out daily activities. Other sensor data (e.g., accelerometer data) may indicate the movement of the sensor to different heights and may indicate the receipt of a swept pressure signal. The passively received swept pressure signal (e.g., where the user does not carry out the arm sweep in response to instructions), may then be analyzed for calculating a MAP of the user per the methods described above.

Optionally, in some embodiments, an accelerometer and gyroscope on the wrist could be used to trace the trajectory of the wrist during daily movements and, hence, determine the height between the wrist and the shoulder, the heart-to-wrist height can then be determined by a single measurement of the shoulder-to-heart height.

Figure 31C:
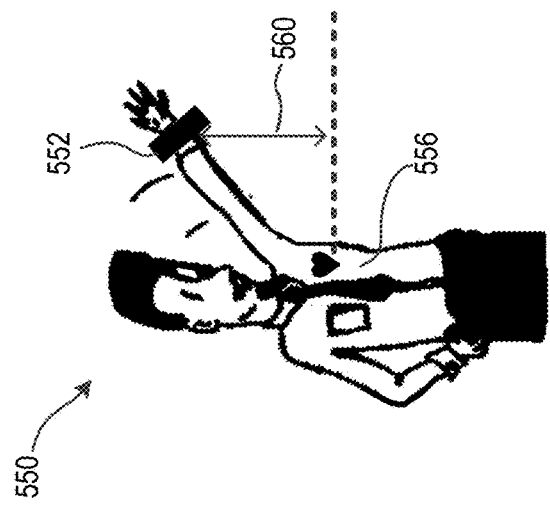
FIGS. 31A-31C illustrate a method of changing the hydrostatic pressure at the wrist of the user according to embodiments of the present invention.
Figure 31B:
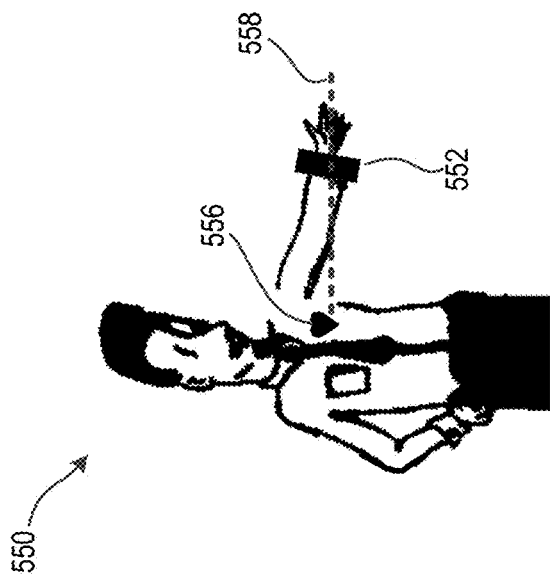
Figure 31A:
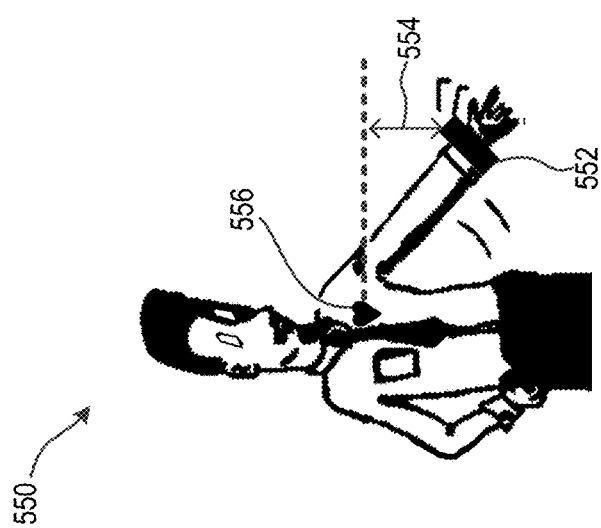

FIGS. 31A-31C illustrate a user 550 sweeping his arm for producing the swept pressure signal for the exemplary method 510. FIG. 31A illustrates the user 550 with a wrist-worn device 552 at a first height 554 relative to his heart 556 where the wrist/wrist-worn device 552 is below the user's heart 556. FIG. 31B illustrates the user 550 with the wrist-worn device 552 at an height 558 where the wrist/wrist-worn device 552 is approximately equal to a height of his heart 556. FIG. 31C illustrates the user 550 with the wrist-worn device 552 at a second height 560 relative to his heart 556 where the wrist/wrist-worn device 552 is above the user's heart 556.

In FIG. 31A, $Height_{heart\text{-}wrist}$ has a positive value as the heart height is greater than the wrist height. Accordingly, per equation (8a), the user 550 experiences a positive hydrostatic pressure at the wrist when the wrist is below the heart 556 of the user. For example, using equation (8a), the user experiences +40 mmHg of hydrostatic pressure at the wrist when the wrist is about 51.28 cm below the heart 556. Thus if the desired applanation of the target artery (or a measurement of the maximum pressure pulse) occurs when the wrist is below the heart height 556, the calculated MAP is less than the applied pressure.

In FIG. 31B, $Height_{heart\text{-}wrist}$ is approximately zero. Accordingly, per equation (8a), at this height, no hydrostatic pressure acts on the wrist relative to the heart 556. If the desired applanation of the target artery (or a measurement of the maximum pressure pulse) occurs when the wrist height is equal to the heart height, the calculated MAP is equal to the applied pressure.

In FIG. 31C, Height$_{heart-wrist}$ has a negative value as the heart height is less than the wrist height, (see equation (9)). Accordingly, per equation (8a), the user 550 experiences a negative hydrostatic pressure at the wrist relative to the heart when the wrist is above the heart 556 of the user 550. For example, using equation (8a), the user experiences −40 mmHg of hydrostatic pressure at the wrist when the wrist is about 51.28 cm above the heart 556. If the desired applanation of the target artery (or a measurement of the maximum pressure pulse) occurs when the wrist is above the heart height 556, the calculated MAP is greater than the applied pressure.

In many embodiments, the transmural pressure at a low end of the arm sweep may be positive where the wrist and device are positioned below the heart (e.g., FIG. 31A) and may be negative at a high end of the arm sweep where the wrist and device are positioned above the heart (e.g., FIG. 31C). In such instances, the desired applanation of the target artery and measurement of the maximum pressure pulse will occur at an intermediate height between the low end of the arm sweep and the high end of the arm sweep where the transmural pressure is zero.

Figure 32:
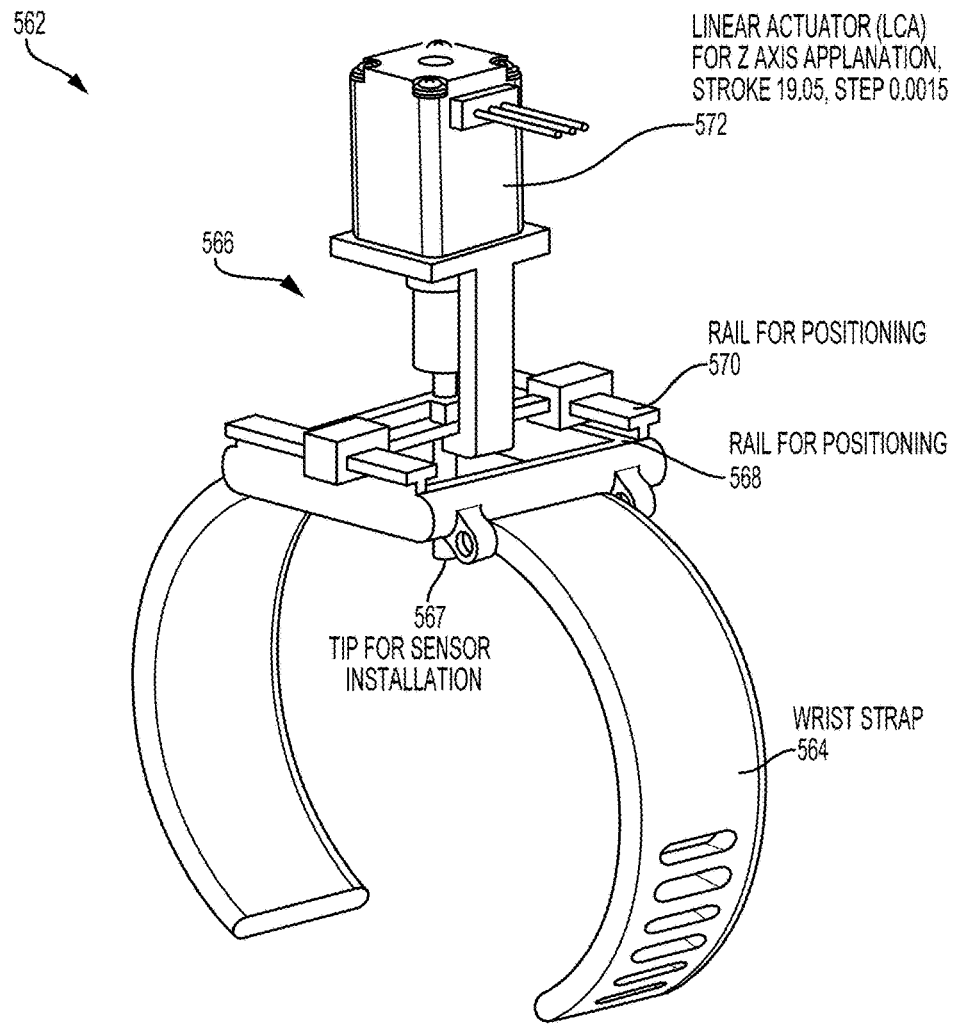
FIGS. 32-35 illustrate various applanation tonometry devices for measuring pressure pulses at the wrist of the user according to embodiments of the present invention.

FIG. 32 shows an exemplary device 562 for monitoring and/or measuring blood pressure of a user. The device 562 may include a wrist strap 564 and an actuator system 566 supported by the wrist strap 564. The actuator system 566 may include a tip 567 for coupling with a pressure sensor (not shown) and may be configured to position the pressure sensor at a desired location relative to a coupled wrist.

The wrist strap 564 may be provided for coupling with a wrist of the user. While illustrated as configured to partially wrap around a user's wrists, other embodiments may fully wrap around a user's wrist. As discussed above, wrist strap 564 may be tightened around the wrist of a user to apply the constant pressure during an MAP measurement. The wrist strap 564 may include clasps, ratcheting mechanisms, or other engagement/tightening features for coupling and/or tightening the device 562 with a wrist of the user.

In some embodiments, the wrist strap 564 may be configured to couple with/modify a separate wearable device with a strap. For example, the wrist strap 564 may couple to the inner surface/contact surface of a strap of a separate wearable device. In some embodiments, the separate device may also be a wrist worn device, such as a watch or the like.

Actuator system 566 may be supported relative to a wrist of the user via wrist strap 564. The actuator system 566 may provide a number of degrees of freedom to a pressure sensor coupled a tip 567 of the actuator system 566 relative to the wrist so that a pressure sensor may be preferentially placed at a desired location on the wrist and with a desired amount of pressure. For example, as illustrated actuator system 566 includes a first rail 568 for positioning a coupled pressure sensor perpendicular or transverse to a coupled wrist of a user. Actuator system 566 may further include a second rail 570 for positioning the tip 567 along the length of a target artery. Further, actuator system 566 may include a linear actuator 572 for urging a pressure sensor coupled thereto against a wrist of a user (e.g., for applying the constant pressure for measuring MAP). In some embodiments, the 2 rail system can be replaced by an automatic step controlled linear stage positioning system. And the linear actuator 572 can be replaced with a voice coil actuator (VCA) or a piezoelectric stack actuator.

The exemplary device 562 may be configured to carry out the exemplary method 510. In some embodiments, the exemplary device 562 may be used to monitor blood pressure using applanation tonometry where the actuator 572 is configured to perform a pressure sweep in the Z direction (i.e. into the wrist) for identifying an MAP and then actuated to apply a preferred pressure so that the pressure sensor provides continuous blood pressure monitoring.

Figure 33:
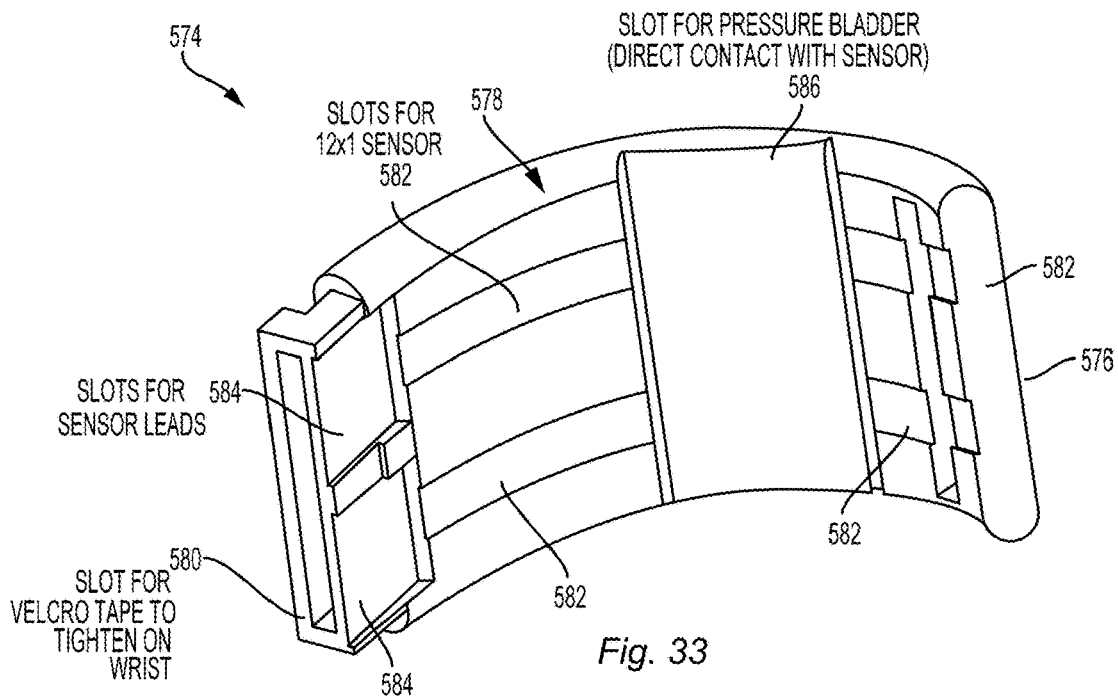

FIG. 33 illustrates another exemplary) device 574 for monitoring and/or measuring blood pressure of a user. The device 574 may include a housing 576 with a curved configuration with an inner surface 578 configured to match the curvature of the underside of the wrist of a user. Housing 576 may include slots or engagement features 580 for coupling with a wrist strap (not shown). The housing 576 may include recessed surfaces/slots 582 for receiving a sensor array and corresponding recessed surfaces/slots 584 for receiving sensor leads of a received sensor array. Further, in some embodiments, housing 576 may include a recessed surface/slot 586 for receiving a pressure actuator for urging a received sensor array against a wrist of a user.

Slots 580 may be configured to receive a wrist strap for coupling the device 574 to a wrist of the user. The slot may, for example, receive a hook-and-loop fastener strap (e.g., Velcro® tape, or the like) for securing the device 574 to the wrist.

The recessed surface 582 may be configured for receiving a pressure sensor array. In some embodiments the pressure sensor array may comprise capacitive pressure sensors, piezoresistive MEMS pressure sensors, piezoelectric film pressure sensors, or the like. In some embodiments a 12×1 pressure sensor array may be received. The recessed surface 582 may align a received sensor array parallel with the wrist strap so that the sensor array traverses the target artery (e.g., radial artery). This may ensure that at least one of the pressure sensors of the pressure sensor array is positioned over the target artery. In the illustrated embodiment, two recessed surfaces 582 are provided for two 12×1 sensor arrays. While illustrated with two recessed surfaces 582 for receiving 12×1 sensor arrays, it should be understood that other embodiments may include single recessed surface 582 or may include three or more recessed surfaces 582 for receiving sensor arrays. Further, while the recessed surfaces 582 are described as configured to receive 12×1 sensor arrays, it should be understood that embodiments are not limited to receiving 12×1 sensor arrays. Embodiments may have recessed surfaces to receive other sensor arrays configurations (e.g., 2×1 sensor arrays, 3×3 sensor arrays, 4×4 sensor arrays, 4×3 sensor arrays, 4×6 sensors arrays or the like). Examples of array geometries include, but are not limited to, rectangular, hexagonal, and arrays with staggered rows or columns.

Recessed surface 586 may be further recessed than recessed surface 582 so that the received pressure actuator may urge the received pressure sensors against the wrist of the user. In some embodiments, the recessed surface 586 may be configured to receive a fluid bladder pressure actuator. The fluid bladder actuator may be configured to be filled with various amounts of fluid to urge a received pressure sensor against a wrist with vary amounts of pressure. Some embodiments may include a fluid bladder pressure sensor for providing a signal indicative of the fluid pressure within the bladder. The recessed surface 586 and the received fluid bladder may extend transverse to the recessed surfaces 582 so that a single fluid bladder may be actuated to urge a plurality of received pressure sensor arrays against the wrist of the user with a single actuation. The bladder actuator in recessed surface 586 may also be configured as an array of bladders to actuate the pressure sensor or sensor array.

The device 574 may be configured to carry out the exemplary method 510. In some embodiments, the exemplary device 574 may be used to monitor blood pressure using applanation tonometry where a received pressure actuator in recess 586 is configured to perform a pressure sweep in the Z direction for identifying an MAP and then actuated to apply a preferred pressure so that the pressure sensor(s) provide continuous blood pressure monitoring.

Figure 34:
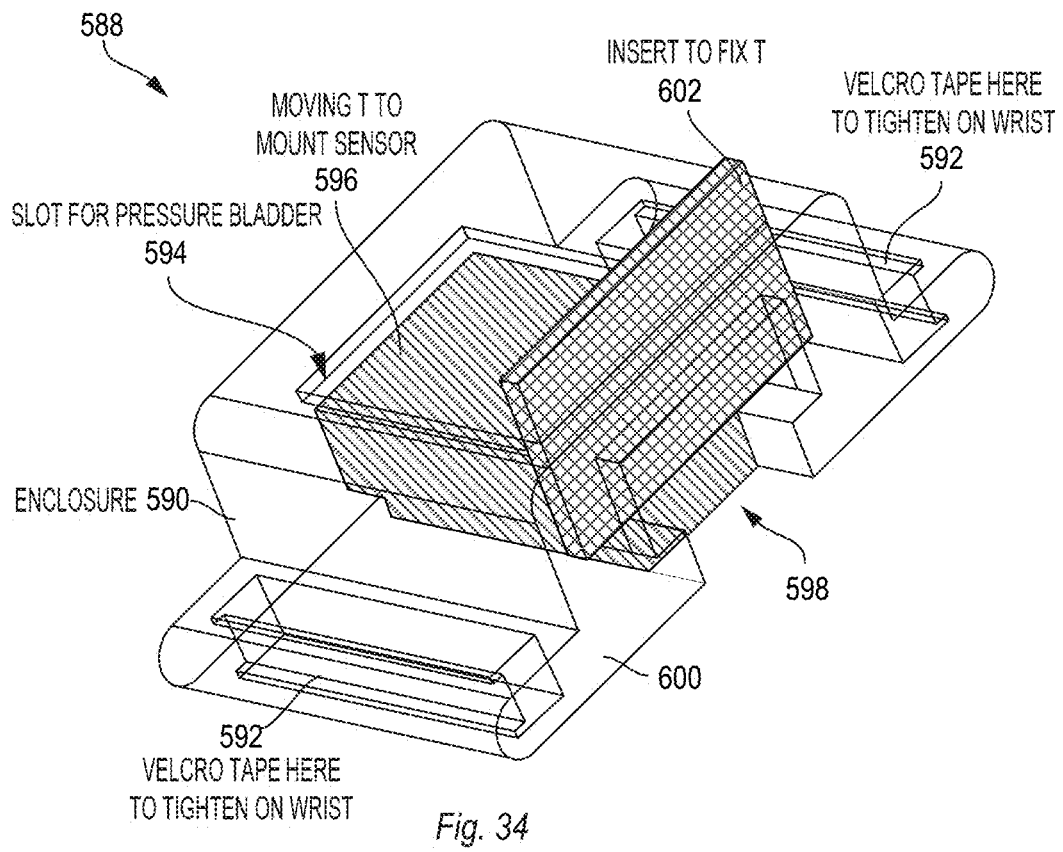

FIG. 34 illustrates another exemplary device 588 for monitoring and/or measuring blood pressure of a user. Exemplary device 588 may include an enclosure 590 having slots 592 for receiving a wrist strap for coupling the device 588 to a wrist of a user. Enclosure 590 may include a slot 594 for receiving a pressure bladder or other type of actuator. Enclosure 590 may further house a driver 596 and disposed between the received pressure actuator and pressure sensor. The device 588 may further include a pressure sensor (not shown) coupled to a surface of the driver 596 that is opposite a surface that couples with the received pressure actuator. The pressure sensor or pressure sensor array can be attached to the moving part 596, then be urged against artery.

Similar to the embodiment 574 illustrated in FIG. 33, device 588 may receive straps through slots 592 for coupling the device 588 with a wrist of the user. Further, the received straps may be used to tighten or to urge the device 588 and a pressure sensor of the device 588 against the wrist of the user. The enclosure 590 may position a driver 596 between a pressure actuator (e.g., a fluid bladder) and a pressure sensor. The driver 596 may be configured to evenly distribute forces from the pressure actuator across the pressure sensor. This may be preferred when device 588 couples with a plurality of pressure sensors and where the pressure actuator comprises a pressure bladder. In some embodiments, a pressure bladder surface may project and retract unevenly or otherwise have a bulge that applies different amounts of pressure depending on a contact location along the bladder surface. Thus, with a pressure sensor array, some pressure sensors may be applied to a wrist with a different pressure compared to other pressure sensors in the array. A rigid driver 596 disposed between a fluid bladder and one or more pressure sensors of device 588 may alleviate these issues by evenly distributing pressure from the fluid bladder across the pressure sensor array.

In the illustrated embodiment, the driver 596 may have a cross section that generally resembles a "T," however other configurations are possible. The enclosure 590 may include a T opening 598 in a sidewall 600 of the enclosure 590. The opening 598 may be dimensioned to receive driver 596 during assembly of enclosure 590. Once the driver 596 is inserted within the enclosure 590, an insert 602 may be positioned between the driver 596 and the opening 598 to secure the driver 596 within the enclosure 590.

Device 588 may couple with capacitive, piezoelectric film, piezoresistive pressure sensors or the like for measuring pressure. Further while discussed as using a fluid bladder as a pressure actuator, other actuators may be used (e.g., linear actuators, solenoids or the like). In some embodiments, utilizing one or more fluid bladders, fluid bladder pressure sensors may be used to provide a signal indicative of a fluid pressure with the one or more bladders.

Similar to the embodiments described above, the device 588 may be used to carry out method 510. Further in some embodiments, the exemplary device 588 may be used to monitor blood pressure using applanation tonometry where a received pressure actuator (e.g., fluid bladder) in slot 584 is configured to perform a pressure sweep in the Z direction by urging driver 596 and coupled pressure sensors against the wrist for identifying an MAP and then actuated to apply a preferred pressure so that the pressure sensor(s) provide continuous blood pressure monitoring.

Figure 35:
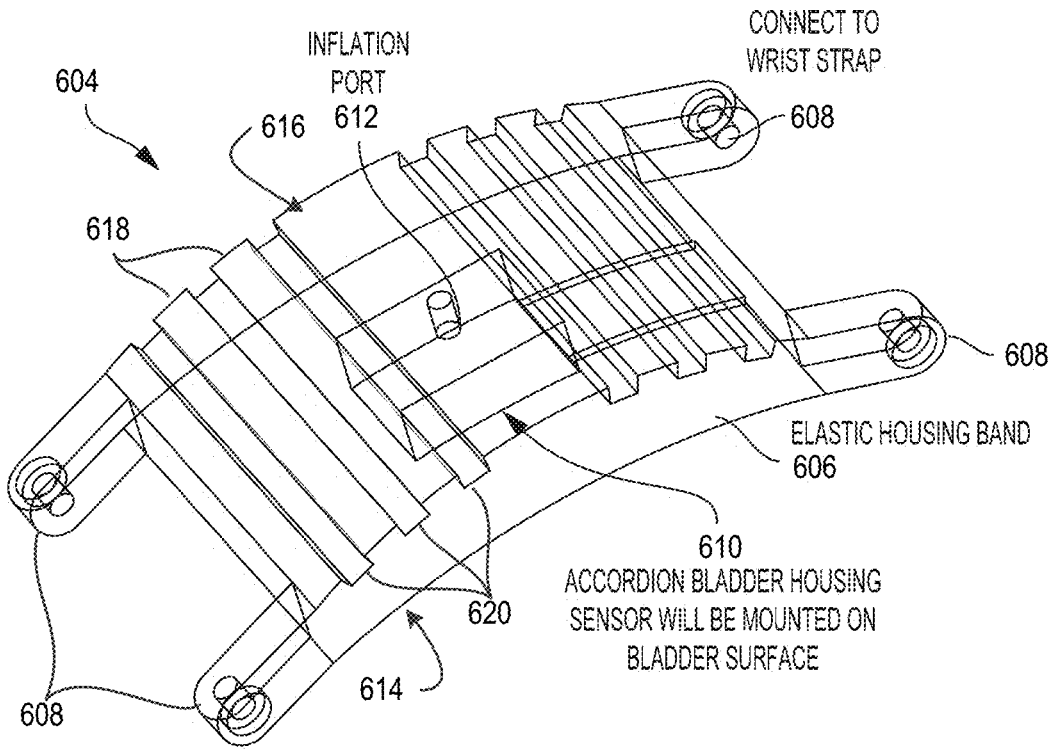

FIG. 35 illustrates yet another exemplary device 604 for measuring or monitoring blood pressure of a user. The exemplary device 604 includes an elastic housing band 606 configured to couple with a wrist of a user. The elastic housing band 606 may include engagement features 608 for coupling to a wrist strap. The elastic housing band 606 may further define a housing for receiving a fluid bladder 610. An inflation port 612 may extend from the fluid bladder housing 610 to an outer surface of the elastic housing band 606.

Elastic housing band 606 may generally have a curved configuration with an inner surface 614 configured to match the curvature of a user's wrist. The outer surface of the elastic housing band 606 may include ribs 618 and grooves 620 that run transverse to a length of the elastic housing band 606. The ribs 618 and grooves 620 may be configured to provide additional flexibility in elastic housing band 606, thereby allowing elastic housing band 606 to better conform to the curvature of a user's wrists.

Fluid bladder housing 610 may be configured to receive a fluid bladder. In many embodiments the device 604 may include an accordion bladder for urging one or more pressure sensors against the wrist of the user. An accordion bladder may avoid applying varying pressure along a contact face of the bladder and may thereby provide even distribution of pressure along a pressure sensor or pressure sensor array.

Figure 36:
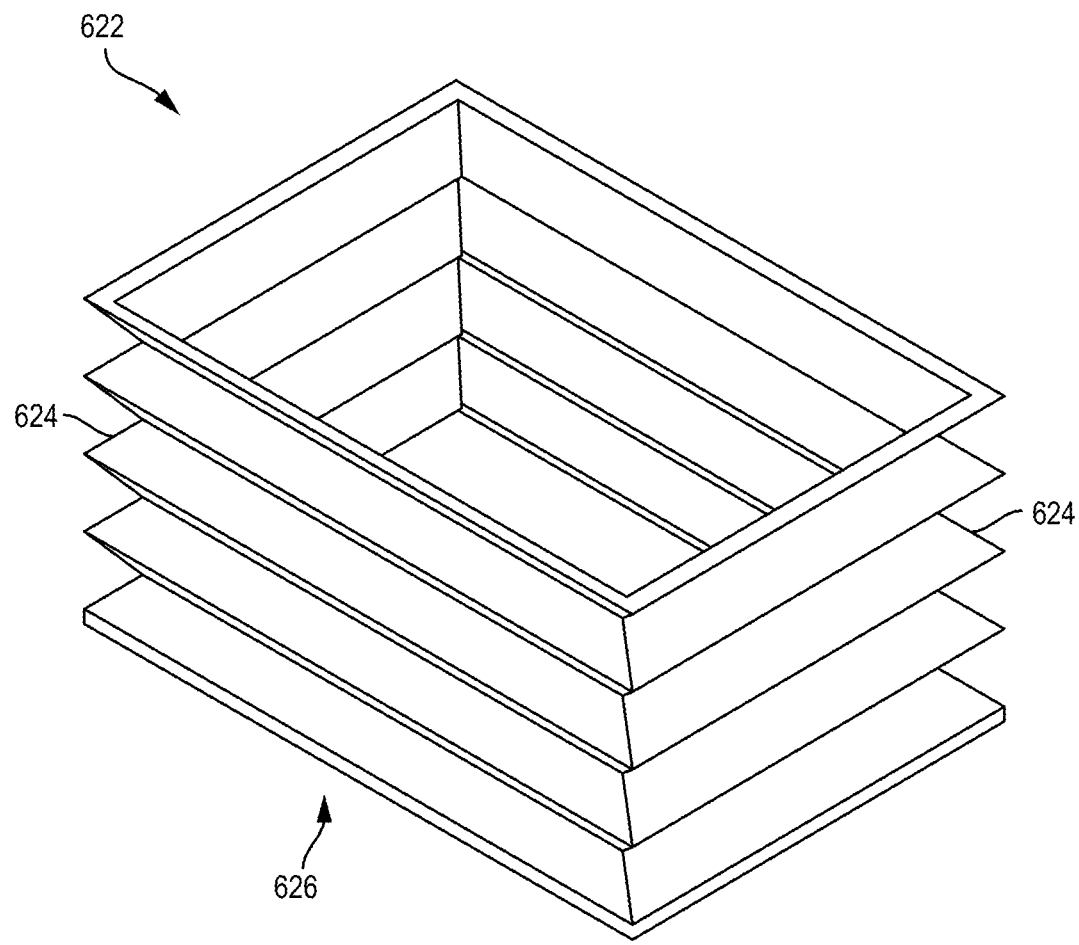
FIG. 36 illustrates a fluid bladder according to embodiments of the present invention.

FIG. 36 illustrates an exemplary accordion bladder 622. Accordion bladder 622 may have side walls 624 that generally define a volume for receiving fluid for expanding accordion bladder 622 a desired amount. The defined volume may be in fluid communication with inflation port 622. The side walls 624 may be generally defined by a plurality of pleats or bellows that expand and contract with the filling and removal of fluid from the bladder 622. Accordion bladder 622 may further include a generally flat distal face 626 for coupling with a pressure sensor or pressure sensor array. Due to the accordion configuration of the bladder 622, fluid filling of the bladder 622 projects the distal face 626 of the bladder 622 linearly and evenly, thus increasing surface contact between the bladder 622 and a pressure sensor or array of sensors and reducing a bladder intramural stress. In this case the fluid pressure inside the bladder will be evenly exerted on surface 626 and been acting directly on the sensor or sensor array, and in turn to the artery. Pressure may then be applied to the pressure sensor/pressure sensor array and the wrist evenly. Accordingly, in some embodiments, a need for a driver disposed between the pressure actuator and the pressure sensor/pressure sensor array may be avoided by using such a bladder 622. The accordion type bladder can be made of thermoplastics (e.g. nylon, polyethylene, Teflon, etc.).

Device 604 may couple with capacitive, piezoelectric film, piezoresistive MEMS pressure sensors or the like for measuring pressure. Further while discussed as using a fluid bladder as a pressure actuator, other actuators may be used (e.g., linear actuators, solenoids or the like). In some embodiments, utilizing one or more fluid bladders, fluid bladder pressure sensors may be used to provide a signal indicative of a fluid pressure with the one or more bladders and the signal may be used for calibrating one or more pressure sensors of the device.

Similar to the embodiments described above, the device 604 may be used to carry out method 510. Further in some embodiments, the exemplary device 604 may be used to monitor blood pressure using applanation tonometry where a received pressure actuator (e.g., accordion fluid bladder) in fluid bladder housing 610 is configured to perform a pressure sweep in the Z direction by urging a coupled pressure sensor/pressure sensor array against the wrist for identifying an MAP and then actuated to apply a preferred pressure so that the pressure sensor(s) provide continuous blood pressure monitoring.

Figure 37:
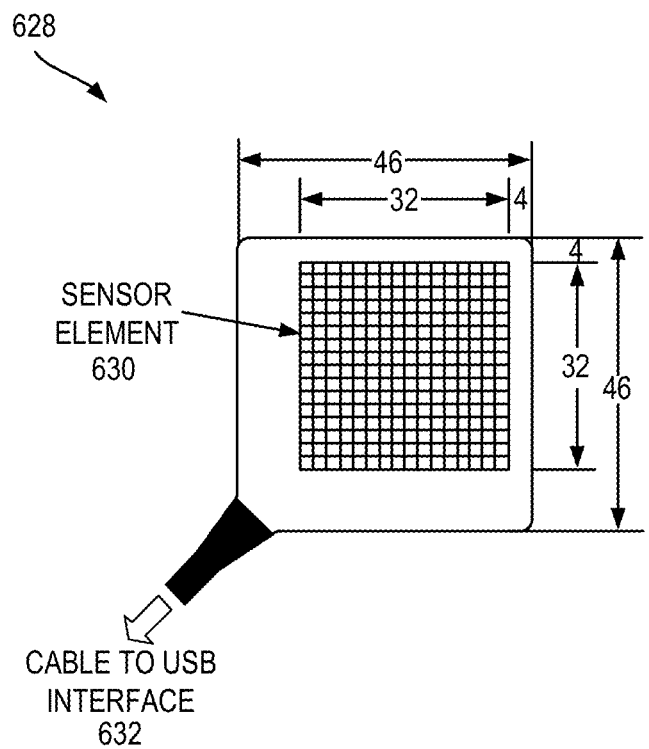
FIGS. 37-39 illustrate various pressure sensor arrays that may be used with embodiments of the present invention.

FIG. 37 shows an exemplary pressure sensor array 628 that may be used with the devices and methods described above. Pressure sensor array 628 may be 46 mm×46 mm in dimension and may comprises a plurality of capacitive pressure sensors 630 arranged in a 16×16 array. The pressure sensor array 628 may include a cable 632 to couple the pressure sensor array to a processing device (controller).

Each element may be approximately 2 mm×2 mm in size, thus providing an active area size of 32 mm×32 mm. The thickness of the active area may be approximately 1 mm. A scan rate may be up to 39 Hz.

Figure 38:
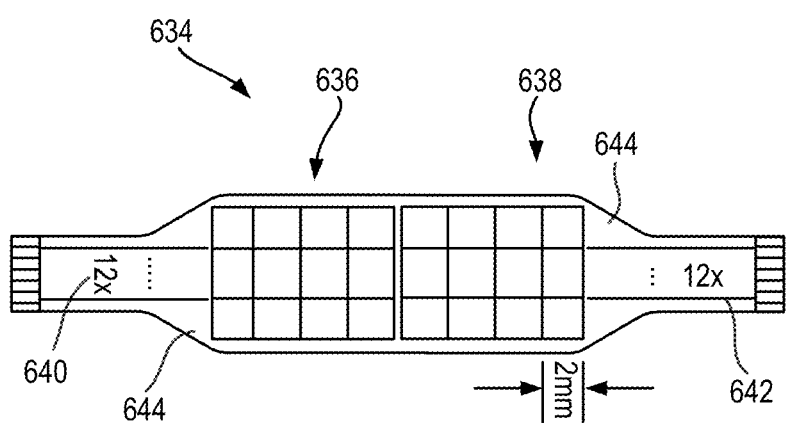

FIG. 38 illustrates another exemplary pressure sensor array 634. The array 634 comprises a first array 636 and a second array 638. The first array 636 may comprise a 4×3 capacitive pressure sensor array and the second array 638 may similarly comprise a 4×3 capacitive pressure sensor array. Each pressure sensor may be 2×2 mm. Accordingly the array 634 may have an active area size of 16 mm×6 mm. The wiring 640 associated with the first array 636 may be routed to a first side of the pressure sensor array 634 and the wiring 642 associated with the second array 638 may be routed to a second side of the pressure sensor array 634. Wiring 640, 642 may each comprise twelve wires that correspond to each of the pressure sensors in the respective arrays.

The first array 636 and the second array 638 may be symmetric so that the application of this sensor array 634 against the user's wrist may also symmetric. This type of array 634 may reduce the cantilever beam loading situation (when sensor array with only one side wiring structure is been pressed against artery, the array will undergo a bending mode between sensor array and wiring pack) and provide a more symmetric load on the sensor array 634.

The wiring 640, 642 for the sensor array 634 may be backed by a fabric material 644 (e.g., a cloth material). A fabric backing material 644 may facilitate installation within a monitoring device and may also reduce undesired bending or stretching loads being applied to the sensor array 634.

Figure 39:
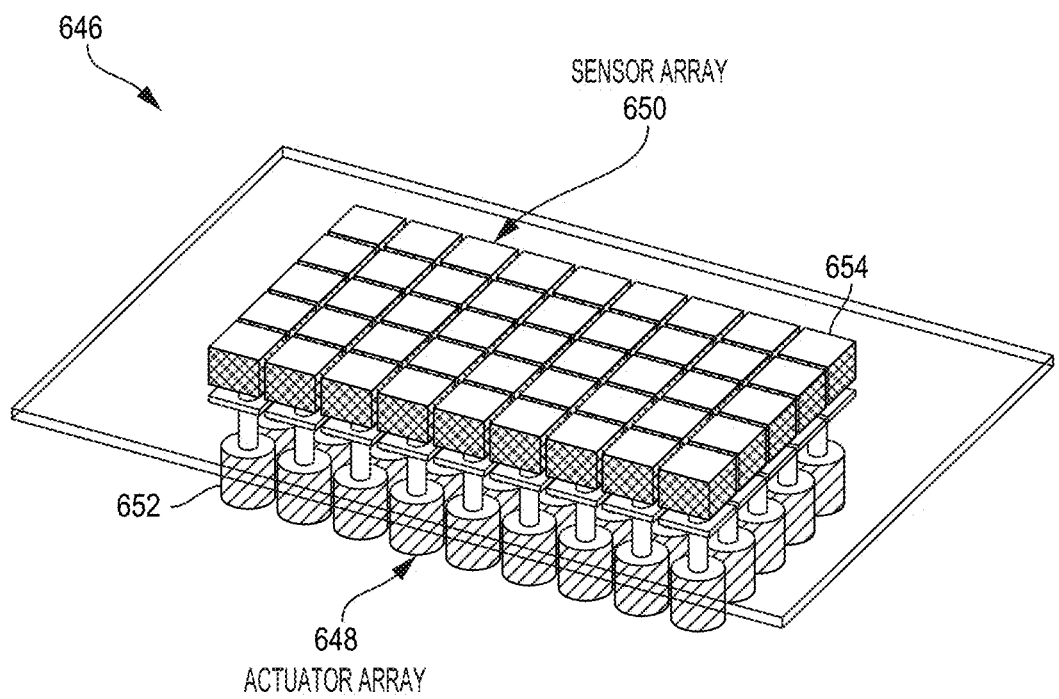

FIG. 39 illustrates an exemplary pressure actuator-pressure sensor assembly 646 that may be used with the devices and methods disclosed herein. Assembly 646 may include an actuator array 648 coupled with a sensor array 650. Each actuator 652 of the actuator array 648 may be coupled to a pressure sensor 654 in the pressure sensor array 650. Each of the actuators 652 in the pressure actuator array 648 may be individually controlled to urge each of the pressure sensors 654 of the pressure sensor array 650 against a wrist/target artery of the user by different amounts. For example, different sensors may be urged different distances or amounts depending on the curvature, contours, or location on the wrist where the sensor is to be urged against. Thus some embodiments, may be configured to tailor to different user wrist curves and contours and may thereby provide more accurate pressure measurements. Accordingly, subsets of the pressure sensor array may be urged against different portions of the wrist. Based on pressure sensor readings, a preferred sensor, sensor location, or sensor signal may be identified and used for blood pressure measurements and/or monitoring.

In some instances when a constant actuation pressure (e.g., 80 mmHg) is applied, the sensor array element with the largest static pressure value may be different from the element with the largest dynamic pressure value. In such instances, the actuator can be moved or a different actuator can be used at a different position until the same element exhibits the largest static pressure as well as the largest dynamic pressure when a constant actuation pressure is applied.

While the array of actuators 648 is illustrated as a 5×9 array and the array of sensors 650 similarly illustrated as a 5×9 array, other array sizes are possible (e.g., smaller or larger). Further, the actuators 652 are illustrated as linear actuators, however other actuators may be used, including but not limited to, fluid bladders, rails actuators, solenoids, or the like. The pressure sensors 654 may be capacitive, piezoresistive, piezoelectric film sensor or the like. The pressure sensor array can be mounted entirely with some backing material to the linear actuator array, or individual elements may be mounted on individual actuators to form the entire array.

Figure 40:
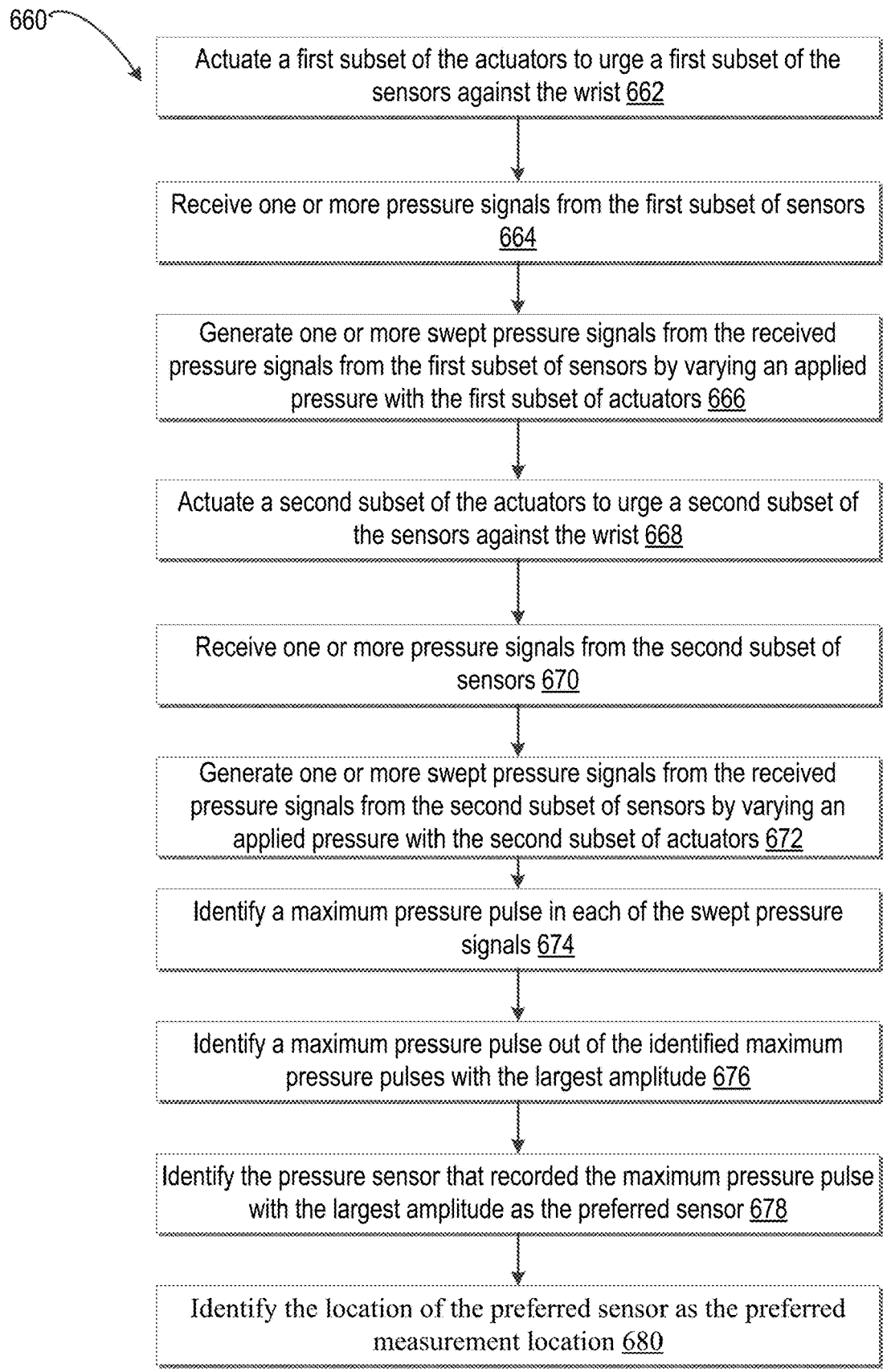
FIG. 40 illustrates a method of selectively actuating subsets of the plurality of pressure sensors against a wrist of a user according to embodiments of the present invention.

FIG. 40 illustrates an exemplary method 660 of operating the exemplary assembly 646 of FIG. 39. At step 662, a first subset of the actuators are activated to urge a first subset of the sensors against the wrist. Pressure signals from the first subset of pressure sensors may then be received 664. One or more swept pressure signals may be received by varying an applied pressure with the first subset of actuators 666. Thereafter, a second subset of the actuators may be activated to urge a second subset of the sensors against the wrist 668. One or more pressure signals from the second subset of sensors may then be received 670. One or more swept pressure signals may be generated by varying the applied pressure with the second subset of actuators 672. A maximum pressure pulse may then be identified in each of the swept pressure signals 674. A maximum pressure pulse with the largest amplitude out of the identified maximum pressure pulses may then be identified 676. In some embodiments, the method may include identifying the pressure sensor that recorded the maximum pressure pulse with the largest amplitude 678 and identifying a location of the identified sensor relative to the wrist of the user 680. In some embodiments, the identified sensor and the identified location may be a preferred sensor and location that most closely identifies a blood pressure of the user and may be used for MAP measurements and blood pressure monitoring via applanation tonometry.

The first/second subset of actuators and the first/second subset of pressure sensors may be a single actuator and a single pressure sensor or may be more than one actuator and more than one sensor. In some embodiments, the first subset of actuators and sensors may be a first half of an array of actuator-sensor assemblies, while the second subset of actuators and sensors may be a second half of the array of actuator-sensor assemblies. In some embodiments, the first subset may be a quarter of an array of actuator-sensor assemblies, and the second subset may be another quarter of the array of actuator-sensor assemblies. Where the first subset and the second subset of actuator-sensor assemblies are less than the total number of actuator-sensor assemblies of the device, the method 660 may be repeated for additional subsets of actuator-sensor assemblies that remain.

While discussed as generating the swept pressure signal by varying the pressure applied by a coupled actuator, a swept pressure signal may, in some embodiments be generated by a change in height of the wrist relative to the heart of the user similar to embodiments described above. However, in many embodiments, a passive method (i.e., that does not require user arm movement) may be preferable as such methods may be performed with little to no inconvenience to the user.

Further, in some embodiments, prior to receiving the one or more pressure signals from the second subset of sensors 670, the first subset of sensors may be retracted away from the wrist.

Additionally, while method 660 is described with steps for processing the data by identifying a maximum pressure pulse with the largest amplitude out of a plurality of identified maximum pressure pulses within each pressure signal, other methods of signal analysis may be provided.

Figure 41:
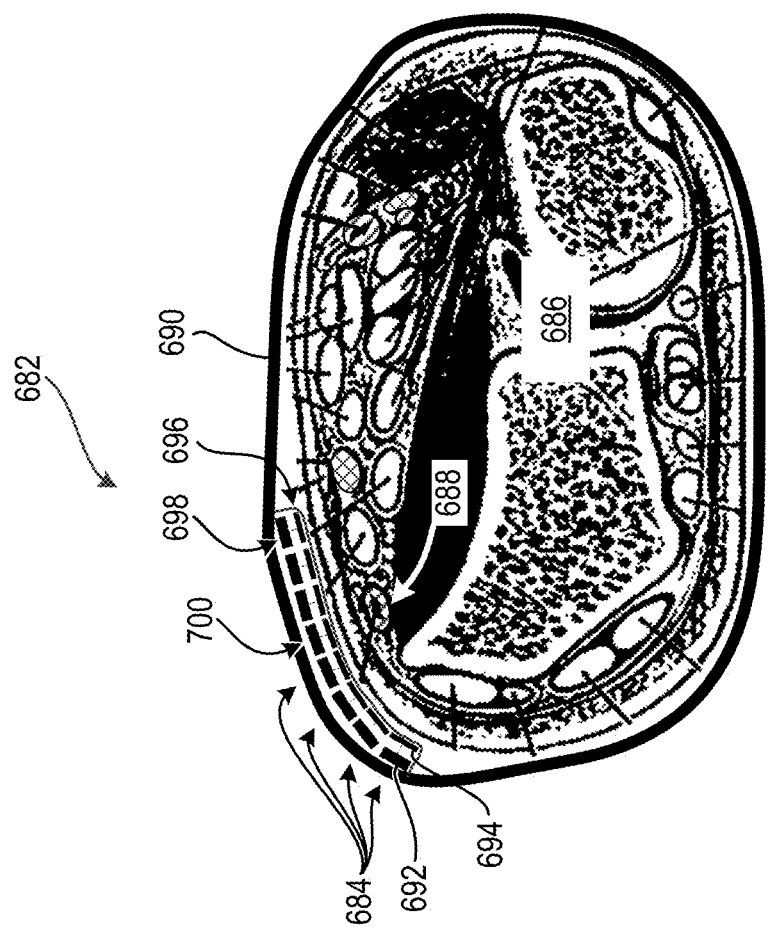
FIG. 41 illustrates the coupling of a device having a plurality of sensors and a plurality of actuators to a wrist of a user according to embodiments of the present invention.

FIG. 41 illustrates the coupling of a device 682 having a plurality of sensor-actuator assemblies 684 to a wrist 686 of a user according to embodiments of the present invention. The device 682 may be configured to measure the blood pressure of a user through applanation of the radial artery 688.

The device 682 includes a strap 690 extends around the wrist 686 and supports each of the plurality sensor-actuator assemblies 684 against the wrist 686. The sensor-actuator assemblies 684 may comprise an actuator 692 coupled with a pressure sensor 694. The plurality of sensor-actuator assemblies 684 may couple with the wrist 686 at a device skin interface 696.

The actuators 692 may be configured to selectively and/or sequentially urge regions of the skin interface 696 adjacent the respective actuators 692 and disposed between the actuators 692 and the wrist against the wrist 686 of the user. The coupled pressure sensor 694 may measure pressure experienced between the actuators 692 and the wrist 686 and provide a respective pressure signal to a processor (not shown). Accordingly, the skin interface 696 may comprise a plurality of regions along the wrist 686. While illustrated as a cross-section, it should be understood that skin interface 696 may comprise an array of regions that correspond to an array of actuators 692.

As illustrated, the skin interface 696 of the device 682 is generally disposed over the radial artery 688. While the radial artery 688 has a small footprint, a sensor or sensor array that covers a large region of the wrist circumference may ensure that the sensor or at least one sensor of a sensor array is positioned and/or oriented over the radial artery 688 in a desired manner. In some embodiments, given that not all sensors 694 of the device 682 are in a preferred position (e.g., where the face of the sensor is perpendicular to a pressure pulse from the target artery), it may be preferable to identify a preferred sensor 694 and a preferred region for applanation of the radial artery 688. This may be carried out by analyzing and comparing the signals from the plurality of sensors 694. For example, the sensors 694 disposed further from the radial artery 688 may provide weaker pressure signals that are not as meaningful for determining a blood pressure of a user.

In the illustrated embodiment with a plurality of sensors 694, the actuators 692 may be selectively and/or sequentially activated to urge different regions of the skin interface 696 against the wrist 686 in order to identify a preferred region for applanation of the radial artery 688. The preferred region for applanation of the radial artery 688 may be identified based on pressure signals received from the one or more sensors 694 of the device 682. For example, the skin interface region disposed between sensor-actuator assembly 698 may be urged against the wrist 686 and a signal may be received from the corresponding sensor 694 of sensor-actuator assembly 698. Additionally, the skin interface region disposed between the sensor-actuator assembly 700 may be urged against the wrist 686 and a signal may be received from the corresponding sensor 694 of the sensor-actuator assembly 700. The signals from the sensor of assembly 698 and the sensor of assembly 700 may then be compared to determine which signal is stronger and/or preferred. Given that the sensor-actuator assembly 700 is positioned closer to radial artery 688 and that the surface face of the sensor of assembly 700 is more perpendicular to pressure pulses from the radial artery 688, the signal from the sensor of assembly 700 may be stronger and preferred in comparison to the signal of the sensor of assembly 698 as it is further from the radial artery 688 and oriented at an angle relative to pressure pulses from the artery 688 and may suffer from increased signal loss.

The regions of the skin interface 696 may be selectively urged such that subsets of the regions of the skin interface 696 are urged against the wrist 686 at a time. The subsets of regions may be urged by multiple actuators 692 where a subset of the actuators 692 are activated (e.g., half the actuators, a quarter of the actuators, a single actuator etc.). Accordingly, in some embodiments the subsets of regions may each be urged selectively and sequentially by a single actuator 692 for identifying a preferred region and sensor 694.

FIG. 42 illustrates the selective actuation of a single region of a skin interface 710 against a wrist of a user according to embodiments of the present invention. Device 701 may include pressure sensors 702 that may be coupled with one of a plurality of actuators 704. The actuators 704 may be supported adjacent the wrist by a strap 706. The sensors 702 may couple with the skin 708 of the user via skin interface 710. As illustrated in FIG. 42, in some embodiments, a single region of the skin interface 710 disposed between an actuator 704 and the wrist may be urged against the wrist for applanation of the artery 712 using a single actuator 704. While applanating the artery 712 with the single actuator 704, the remaining actuators 704 may not be actively urging respective regions of the skin interface 710 against the wrist. This manner of actuation of regions of the skin interface 710 against the wrist may be performed selectively and sequentially in order to identify a preferred region for applanation of the artery 712 and a preferred sensor signal from one of the sensors 702.

FIG. 43 illustrates device 701 selectively actuating more than one region of a skin interface 710 against a wrist of the user according to embodiments of the present invention. As illustrated in FIG. 43, a subset of regions (e.g., the right half the regions) of the skin interface 710 positioned between actuators 704 and the wrist are urged against a wrist of a user by activating two of the actuators 704 while the other two actuators 704 may not be actively urging respective regions of the skin interface 710 against the wrist. In some embodiments, pressure signals may only be processed from the advanced pressure sensors 702. In some embodiments, pressure signals may only be received from the advanced pressure sensors 702. In some embodiments, the received pressure signals may be processed to identify a blood pressure of the user or compared to identify a preferred pressure sensor 702 between the two advanced pressure sensors 702 and a preferred region for applanation. In such a method, processing time may be reduced as only a subset of pressure signals may be received from the subset urged regions.

While FIG. 41-FIG. 43 illustrate devices with a plurality of individual sensors 702, other embodiments may utilize a sensor system comprising a pressure film sensor. For example, FIG. 44 illustrates a device 800 that includes a pressure film sensor 802 that may be coupled with a plurality of actuators 804. The actuators 804 may be supported adjacent the wrist by a strap 806. The sensor 802 may couple with the skin 808 of the user via skin interface 810. As illustrated in FIG. 44, in some embodiments, a single region of pressure film sensor 802 and a single region of the skin interface 810 may be urged against the wrist for applanation of the artery 812 using a single actuator 804. While applanating the artery 812 with the single actuator 804, the remaining actuators 804 may not be actively urging respective regions of the pressure film sensor 802 and the skin interface 810 against the wrist. This selective actuation of regions of the pressure film sensor 802 against the wrist may be performed selectively and sequentially in order to identify a preferred region of the pressure film sensor 802 and skin interface 810 for applanation of the artery 812.

FIG. 45 illustrates device 800 selectively actuating a subset of regions of a skin interface 810 and pressure film sensor 802 against a wrist of the user according to embodiments of the present invention. As illustrated in FIG. 45, a subset of regions (e.g., the right half the regions) of the skin interface 810 are urged against a wrist of a user by activating two of the actuators 804 on the right while the other two actuators 804 on the left may not be actively urging the respective regions of the pressure film sensor 802 against the wrist. Regions of the pressure film sensor 802 may be selectively and/or sequentially urged against the wrist to identify a preferred region of the skin interface 810 for applanation of the target artery 812 and a preferred region of the pressure film sensor 802 for receiving pressure signals.

Figure 46A:
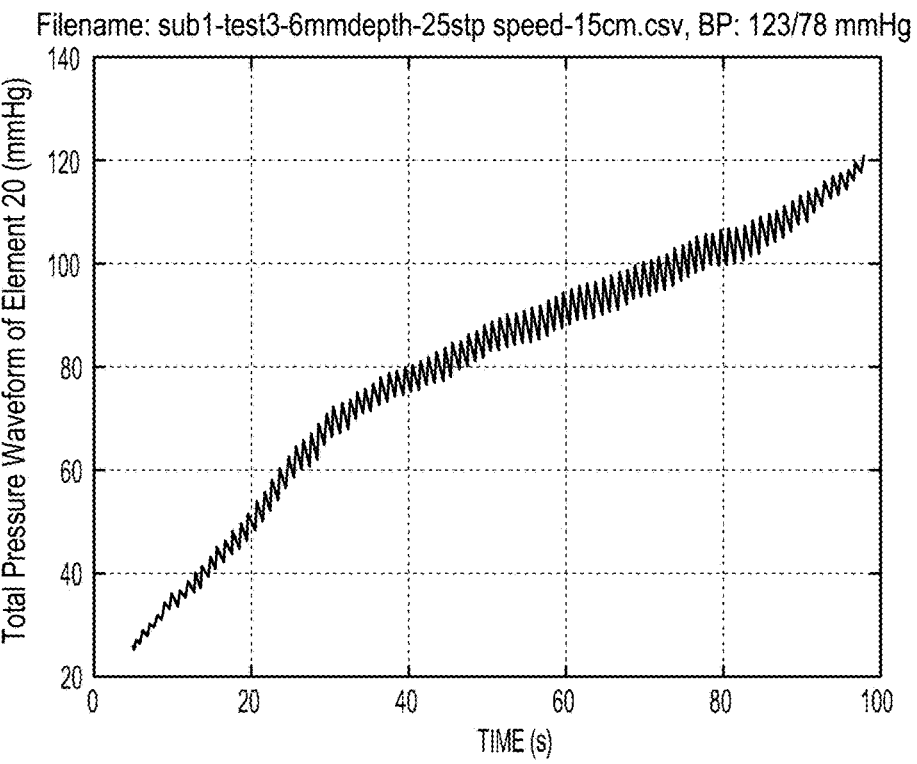
FIGS. 46A-46C show pressure sensor data obtained from an array of pressure sensors applied to a user according to embodiments of the present invention.
Figure 46B:
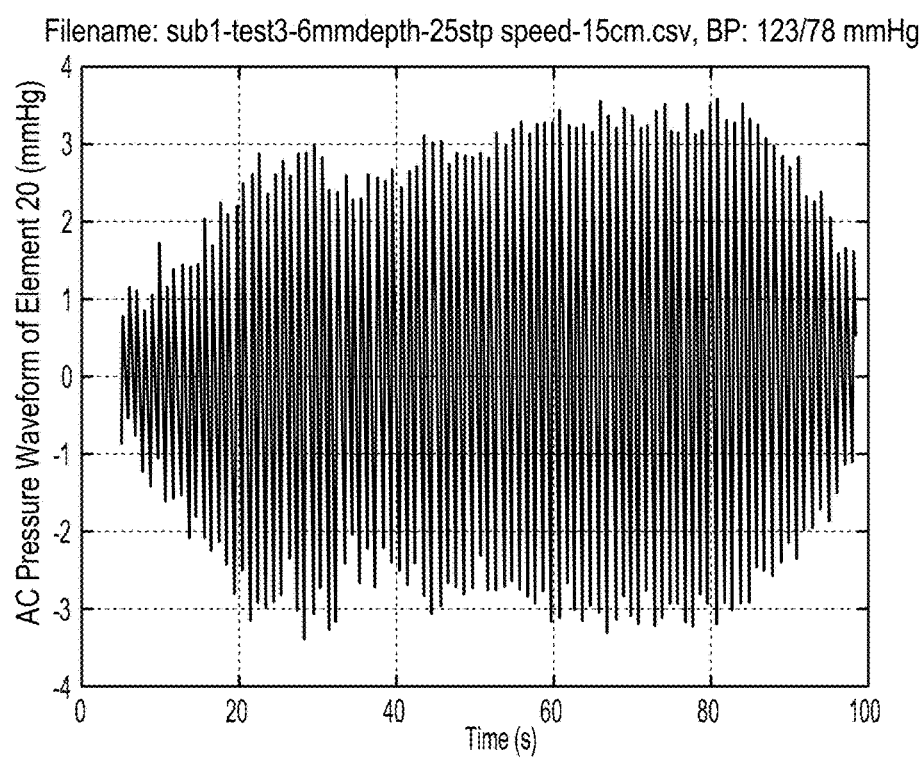
Figure 46C:
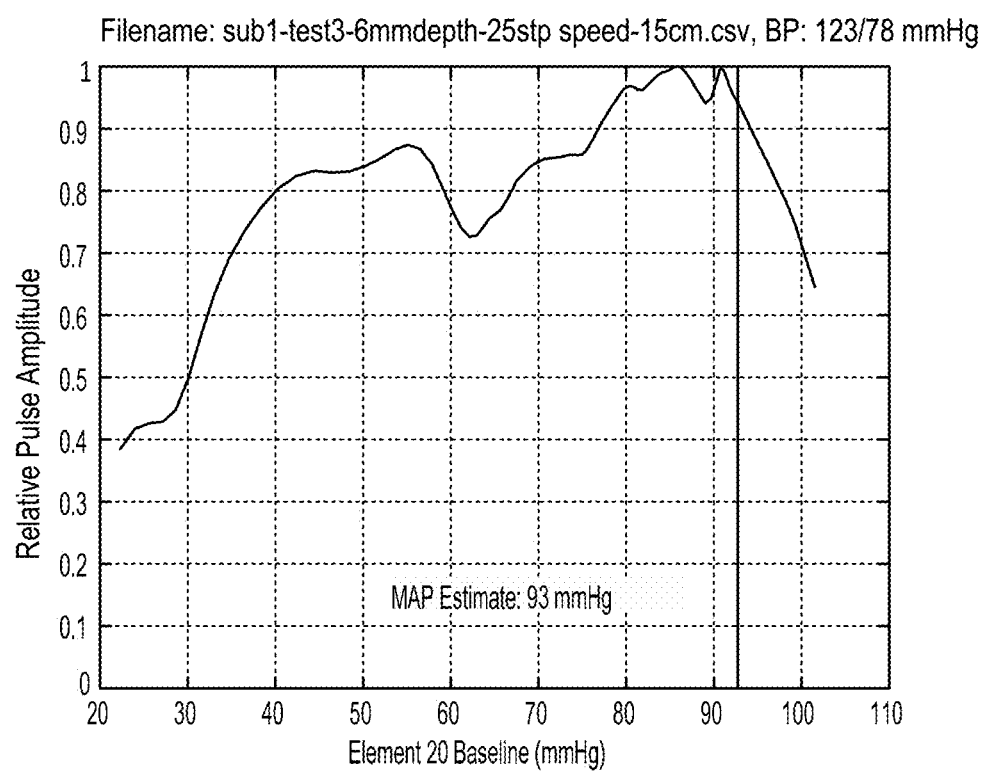

FIG. 46A-46C show sensor data obtained from an array of pressure sensors applied to a user according to embodiments of the present invention. The data was received from a 1×12 array of pressure sensors applied to a subject's wrist at the radial artery. The pressure actuator was a linear actuator that traveled approximately 6 mm perpendicularly to the wrist surface with a speed of 25 steps/s (each step was approximately 38 μm). The wrist was approximately 15 cm below the heart. The reference blood pressure taken from an oscillometric brachial monitor was systolic blood pressure (123 mmHg) and diastolic blood pressure (78 mmHg). The reference mean arterial pressure was estimated by mean arterial pressure=⅓*(systolic blood pressure)+⅔*(diastolic blood pressure). The total (i.e., AC and baseline) pressure waveform from the sensor element with the strongest pulsatile (i.e., AC) component is illustrated in the pressure vs. time chart shown in FIG. 46A. The AC pressure waveform versus time for the same sensor element is illustrated in FIG. 46B. FIG. 46C shows the relative AC amplitude vs. baseline from the same sensor element. Element 20 had the largest pressure amplitude measurements while the remaining received relatively weaker pressure signals Accordingly, element 20 may be a preferred sensor and may be considered to be placed at a preferred region and/or orientation adjacent the target artery. Thus, in some embodiments, a blood pressure measurement may be calculated based on this pressure signal alone.

Figure 47:
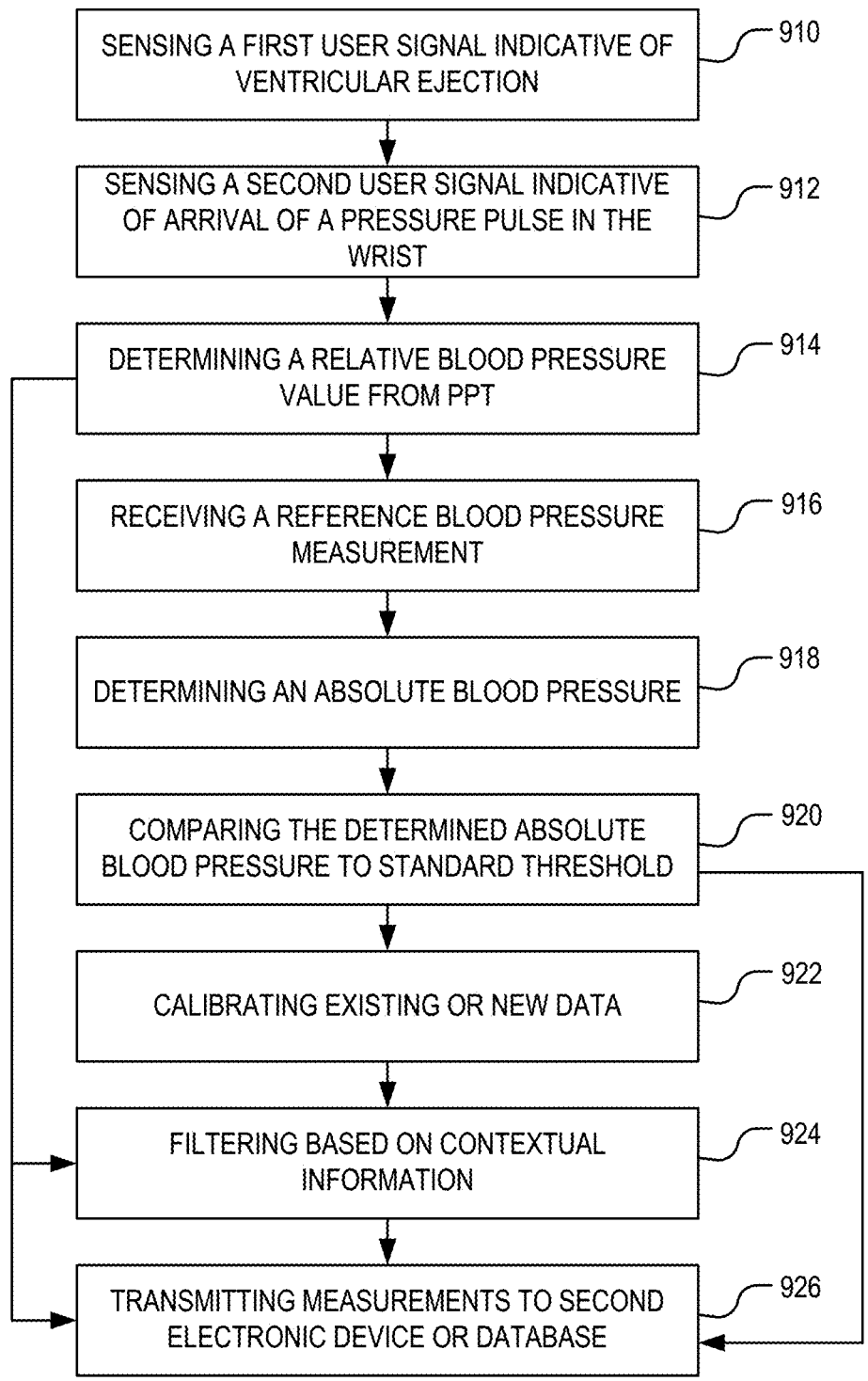
FIG. 47 illustrates a method of calibrating relative blood pressure signals according to embodiments of the present invention.

FIG. 47 illustrates a method of calibrating relative blood pressure signals according to embodiments of the present invention. As described above, relative blood pressure values may be calibrated with a reference measurement to determine blood pressure values on an absolute scale. At step 910, a first sensor of a wrist-worn device non-invasively engaging the skin on the wrist of the user, senses a first user signal indicative of ventricular ejection of blood from the heart of the user. The first sensed ventricular ejection signal has an associated ventricular ejection time. At step 912, a second sensor of the wrist-worn device non-invasively engaging the skin on the wrist of the user, senses a second user signal indicative of arrival of a pressure pulse in the wrist. The second sensed pressure pulse signal is associated with the first sensed ventricular ejection signal and has an associated pulse arrival time. A relative blood pressure value may be then determined in response to a first PTT identified from a difference between the ventricular ejection time and the pulse arrival time per step 914.

At step 916, an absolute reference blood pressure measurement obtained in coordination with the relative blood pressure may be received from an accurate reference measurement device. The absolute reference blood pressure measurement may be obtained from a variety of sources including volume oscillometry (as described herein), an oscillometric cuff, or an input by the user. In step 918, the absolute blood pressure of the relative blood pressure value may then be determined in response to a difference between the relative blood pressure and the absolute reference blood pressure. The determined absolute blood pressure may be compared to a standard performance threshold (e.g., reference measurement) per step 920. For example, if the difference between the threshold value is greater than ±5 mmHg mean error or ±8 mmHg sigma error, a blood pressure index of the relative blood pressure values may be transmitted instead of the absolute blood pressure values per step 926. In addition, a plurality of relative blood pressure values determined prior to or subsequent the first PTT may further be calibrated based on the difference between the relative blood pressure associated with the first PTT and the absolute reference blood pressure for backward or retroactive calibration of existing data or forward calibration of new data per step 922.

The blood pressure signals may be filtered based on contextual information associated with the user per step 924. As described above, contextual filtering may be based on a variety of information that may provide context for any measured blood pressure changes or artifacts. Accordingly, the filtered blood pressure signals may be masked, discarded, or automatically annotated. The plurality of calibrated and/or non-filtered blood pressure values may then be transmitted to a second electronic device (e.g., watch, mobile device, tablet, or computer) or database for further processing (e.g., absolute blood pressure tracking), storage (e.g., electronic medical record), retrieval by other devices or programs (e.g., health software application), and/or display to the user or their health care professional per step 926. It will be appreciated that in some situations, PTT measurements from step 914 may be directly filtered per step 924 and/or transmitted per step 926 directly to the second electronic device or database in a non-calibrated (e.g., non-manipulated) format. The second electronic device or database may be better suited in some instances to store individual calibration equations and process the PTT measurements to determine absolute blood pressure values. As discussed above, the second electronic device or database may not only process the PTT measurements (e.g., calibration of relative blood pressure signals), but also allow for storage of the data in a variety of formats (e.g., non-calibrated PTT measurements, trending data, absolute blood pressure values), retrieval of the data by other devices or programs, and/or display of the data.

Figure 48:
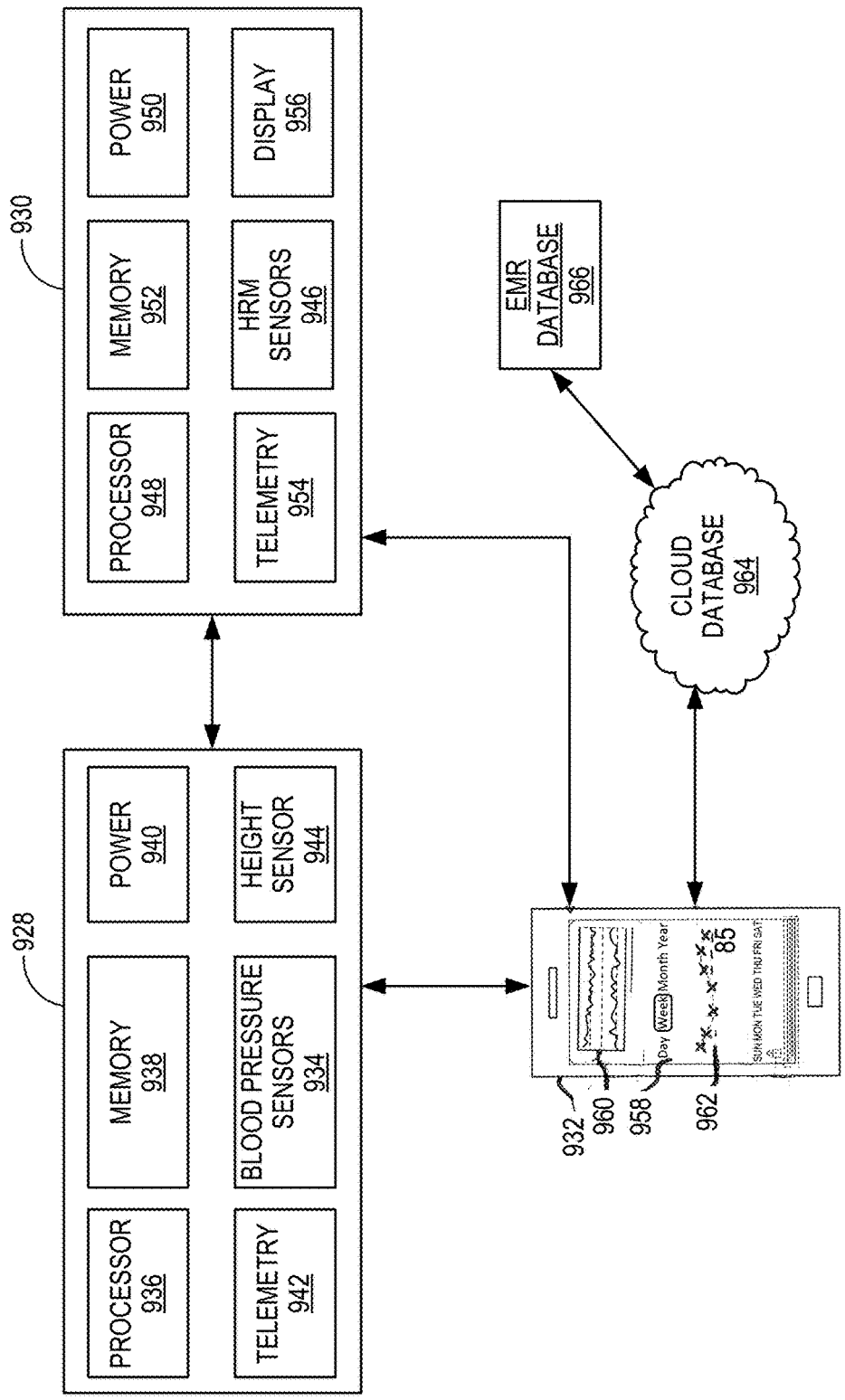
FIG. 48 illustrates a schematic diagram of an overall system including a wrist-worn band, wrist-worn electronic device, and a mobile phone according to embodiments of the present invention.

FIG. 48 illustrates a schematic example of an overall system including a first wrist-worn band 928, a second wrist-worn electronic device (e.g., watch 930), and a third non-wrist device (e.g., a mobile device 932) according to embodiments of the present invention. The first wrist-worn band 928 may comprise any one of the blood pressure monitoring sensor arrangements disclosed herein and is configured to non-invasively engage the skin on the wrist of the user. The elongate band 928 is releasably coupleable to a second wrist-worn watch 930 as described in greater detail below. At least one PTT or pressure sensor 934 may be coupled to the elongate band 928, the sensor non-invasively engaging the skin over the wrist of the user for measuring user signals from the cardiovascular system of the user. In addition, a height sensor 944 may be coupled to the elongate band 928 so as to account for any hydrostatic pressure effects associated with the measured cardiovascular user signals. One or more processors 936 may be coupled to the elongate band 928 and the at least one PTT or pressure sensor 934 for determining relative or absolute blood pressure signals based on the user signals. The one or more processors 936 can be implemented in any suitable form, including one or more field-programmable gate arrays (FPGA). The elongate band 928 may further include memory 938, such as read only memory (ROM) and/or random access memory (RAM). A power source 940 may also be coupled to the elongate band 928 and the processor 936 or the at least one PTT or pressure sensor 934 for providing power to the wrist-worn band 928. A telemetry/wireless interface 942 (e.g., Bluetooth or WiFi) may also be coupled to the elongate band 928 and the processor 936.

The second wrist-worn watch 930 may comprise one or more heart rate monitor sensor(s) 946, a second processor 948, a second power source 950, a second memory 952, a second telemetry interface 954, and/or a user display 956 that are enclosed within a distinct and separate housing from the first wrist-worn blood pressure monitoring band 928. The first wrist-worn band 928 may easily communicate (e.g., transmit blood pressure values, receive updated instructions, such as new calibration equations, etc.) with the second wrist-worn watch 930 via WiFi or Bluetooth. Still further, the telemetry interface 942 of the elongate band 928 may be configured to communicate not only with the second wrist-worn watch 930, but also with the third non-wrist device (mobile device 932). For example, the telemetry interface 942 of the elongate band 928 may be configured to transmit the relative or absolute blood pressure signals to a health application software 958 on the mobile device 932. The mobile device 932 may in turn display the relative blood pressure signals 960 and/or the absolute blood pressure signals 962 in a graphical format dictated by the health application software 958 for a time period of a day, week, month, or year. The blood pressure graphs 960, 962 may then be viewable by the user or a health care professional for use in diagnostic or therapeutic decision making. Still further, the mobile device 932 may be configured to receive the blood pressure signals from the wrist-worn band 928 and/or wrist-worn watch 930 and in turn re-transmit this data to a cloud database 964 for further processing, storage, or retrieval by other devices or programs. For example, the blood pressure measurements may be transmitted specifically to an electronic health or medical record database 966.

Figure 49A:
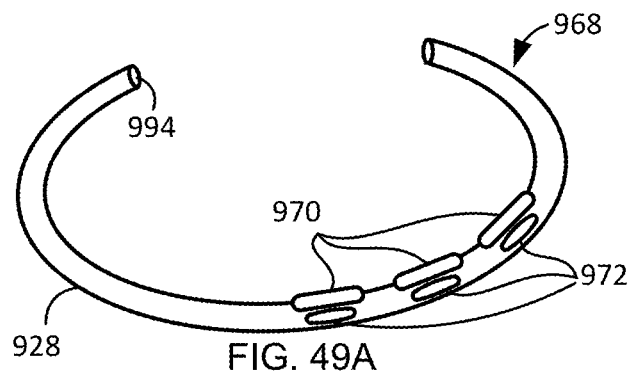
FIGS. 49A-49C schematically illustrate a plurality of wrist-worn bands for coupling to a wrist-worn electronic device according to embodiments of the present invention.
Figure 49B:
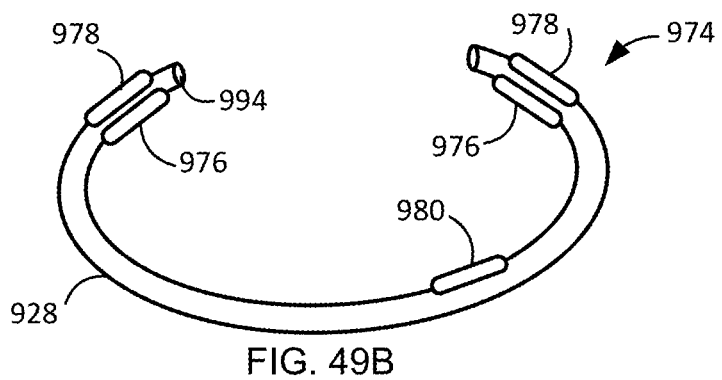
Figure 49C:
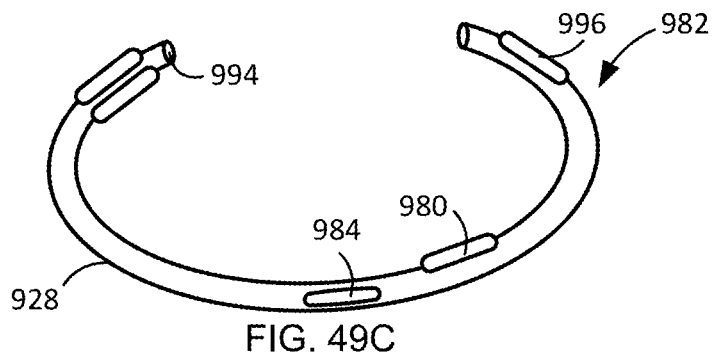

Referring now to FIGS. 49A-49C, providing bands 928 that are releasably coupleable to the watch 930 provides for user customization of the watch 930 based on the desired sensor monitoring (e.g., absolute, relative, passive, active, etc.). For example, a first applanation tonometry band 968 as illustrated in FIG. 49A may comprise a plurality of pressure sensors 970 and actuators 972 for measuring absolute blood pressure values. The pressure sensors 970 may comprise pressure transducers as illustrated or still further a piezo-electric film or piezoresistive film for sensing. The pressure sensors 970 are configured to non-invasively engage an anterior surface of the wrist of the user and be positioned over a radial artery so as to passively or actively measure the absolute blood pressure signals. The actuators 972 urge each of the pressure sensors 970 against the wrist of the user by applying a constant or variable pressure thereto.

FIGS. 49B and 49C illustrate bands 974, 982 for measuring relative blood pressure values. As described above, the least one PTT sensor may comprise first and second sensors. The first sensor is configured to measure a first user signal indicative of ventricular ejection of blood from the heart of the user, the first sensed ventricular ejection signal having an associated ventricular ejection time. The second sensor is configured to measure a second user signal indicative of arrival of a pressure pulse in the wrist, the second sensed pressure pulse signal associated with the first sensed ventricular ejection and having an associated pulse arrival time, wherein the relative blood pressure signal is determined from a difference between the ventricular ejection time and the pulse arrival time. The first sensor may comprises at least one (or combination thereof) ICG, ECG, BCG, PCG, and/or SCG sensor coupled to the elongate band. The second sensor may comprise at least one PPG sensor or physical pressure pulse sensor coupled to the elongate band.

With reference to FIG. 49B, a second band 974 may comprise an ICG/PPG sensor arrangement for measuring relative blood pressure values. In particular, the at least one ICG sensor may comprise at least a first pair of dry electrodes 976 non-invasively engaging glabrous skin on an anterior surface of the wrist of the user and a second pair of dry electrodes 978 contacted by at least two separate fingers (or a thumb, palm, or wrist) of a hand opposite a hand on which the device is worn to provide cross-body dynamic impedance measurements. The PPG sensor 980 may comprise at least one infra-red, red, or green optical source and a detector positioned over a radial artery of the wrist (or the finger or arm) of the user. With reference to FIG. 49C, a third band 982 may comprise a BCG/PPG sensor arrangement for passive monitoring of relative blood pressure values. The BCG sensor 984 may comprise an accelerometer non-invasively engaging an anterior surface of the wrist so as to passively measure a relative blood pressure. At least one height sensor 996 may be coupled to the elongate band 982 so as to account for hydrostatic pressure effects. The user may selectively choose between the first 968, second 974, or third bands 982 for the desired sensor monitoring and may further interchange the bands at any time period as desired via a releasable coupling feature 994. The at least one releasable connection or coupling feature 994 of the elongate bands 968, 974, or 982 may help secure the selected band 986 to the heart rate monitor watch device 930.

Figure 50:
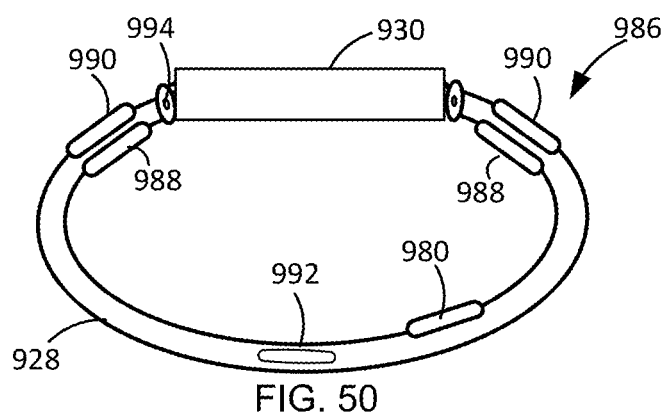
FIG. 50 schematically illustrates an active band releasably coupleable to a wrist-worn electronic device according to embodiments of the present invention.

As shown in FIG. 50, a fourth selected band 986 is releasably coupleable to the watch device 930 and includes two types of sensor monitoring arrangements. An ECG sensor arrangement is provided for cross-body electrical potential measurements and a SCG sensor arrangement for comparison of the ECG measurement to another active measurement that has little or no error due to hydrostatic pressure changes as the SCG measurement is made at the chest which is relatively aligned with a height of the heart. The ECG sensor comprises a first pair of dry electrodes 988 non-invasively engaging glabrous skin on an anterior surface of the wrist of the user and a second pair of dry electrodes 990 contacted by at least two separate fingers (or a thumb, palm, or wrist) of a hand opposite a hand on which the device is worn. The SCG sensor 992 comprises an accelerometer and the accelerometer 992, wrist-worn band 986 and/or hand of the wrist-worn device non-invasively engage the sternum.

It will be appreciated that personal information data may be utilized in a number of ways to provide benefits to a user of a device. For example, personal information such as health or biometric data may be utilized for convenient authentication and/or access to the device without the need of a user having to enter a password. Still further, collection of user health or biometric data (e.g., blood pressure measurements) may be used to provide feedback about the user's health and/or fitness levels. It will further be appreciated that entities responsible for collecting, analyzing, storing, transferring, disclosing, and/or otherwise utilizing personal information data are in compliance with established privacy and security policies and/or practices that meet or exceed industry and/or government standards, such as data encryption. For example, personal information data should be collected only after receiving user informed consent and for legitimate and reasonable uses of the entity and not shared or sold outside those legitimate and reasonable uses. Still further, such entities would take the necessary measures for safeguarding and securing access to collected personal information data and for ensuring that those with access to personal information data adhere to established privacy and security policies and/or practices. In addition, such entities may be audited by a third party to certify adherence to established privacy and security policies and/or practices. It is also contemplated that a user may selectively prevent or block the use of or access to personal information data. Hardware and/or software elements or features may be configured to block use or access. For instance, a user may select to remove, disable, or restrict access to certain health related applications that collect personal information, such as health or fitness data. Alternatively, a user may optionally bypass biometric authentication methods by providing other secure information such as passwords, personal identification numbers, touch gestures, or other authentication methods known to those skilled in the art.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

While the exemplary embodiments have been described in some detail, by way of example and for clarity of understanding, those of skill in the art will recognize that a variety of modifications, adaptations, and changes may be employed.

What is claimed is:

1. An electronic band assembly comprising:
   an elongate band configured to be releasably coupled with a wrist-worn watch or a wrist-worn heart rate monitor to form a wrist-worn assembly configured for extending around a wrist of a user and non-invasively engaging skin on the wrist of the user;
   impedance cardiogram (ICG) electrodes configured for use in measuring cross-body impedance of the user, wherein the ICG electrodes comprising a first pair of electrodes and a second pair of electrodes, wherein the first pair of electrodes is mounted to the elongate band for engaging the skin on the wrist of the user, and wherein the second pair of electrodes is externally mounted to the elongate band for contacting by two fingers of a hand of the user on an arm opposite to the wrist of the user on which the wrist-worn assembly is worn;
   a blood pressure pulse sensor configured to generate a blood pressure pulse signal indicative of arrival of blood pressure pulses at the wrist;
   a controller coupled to the elongate band, wherein the ICG electrodes are connected to the controller, wherein the controller measures the cross-body impedance of the user via the electrodes, wherein the controller processes the cross-body impedance to determine a ventricular ejection time for a ventricular ejection of blood from a heart of the user, wherein the controller is connected to the blood pressure pulse sensor, wherein the controller processes the blood pressure pulse signal to determine an arrival time at the wrist of a blood pressure pulse generated by the ventricular ejection, wherein the controller determines a pulse transit time (PTT) of the blood pressure pulse from the heart to the wrist based on the ventricular ejection time and the arrival time, and wherein the controller determines a relative or absolute blood pressure of the user based on the PTT;
   a power source coupled to the elongate band and the controller; and
   a telemetry interface coupled to the elongate band and the controller, wherein the telemetry interface is configured to communicate with the wrist-worn watch or the wrist-worn heart rate monitor via wireless communication.

2. The device electronic band assembly of claim 1, wherein the wrist-worn watch or the wrist-worn heart rate monitor comprises a housing encasing a second controller, second power source, and second telemetry interface, wherein the elongate band further comprises at least one connection feature for securing the elongate band to the housing.

3. The electronic band assembly of claim 1, wherein the blood pressure pulse sensor comprises at least one photoplethysmogram (PPG) sensor or physical pressure pulse sensor coupled to the elongate band, wherein the at least one PPG sensor comprises at least one infra-red, red, or green optical source and a detector configured to be positioned over a radial artery of the wrist of the user, wherein the physical pressure pulse sensor comprises at least one pressure transducer, accelerometer, or strain gauge configured to be positioned over a radial artery of the wrist of the user.

4. The electronic band assembly of claim 1, further comprising at least one height sensor, barometric pressure sensor, gyroscope, or accelerometer coupled to the elongate band so as to generate output that is processed to determine a height difference between the electronic band assembly and the heart of the user that is used to account for hydrostatic pressure effects in the determination of the relative or absolute blood pressure of the user.

5. The electronic band assembly of claim 1, wherein the telemetry interface is configured to transmit the relative or absolute blood pressure signals to an electronic device other than the wrist-worn watch or the wrist-worn heart rate monitor.

6. The electronic band assembly of claim 1, wherein the telemetry interface of the elongate band is configured to transmit the relative or absolute blood pressure signals to an electronic health or medical record or health application software.

7. The electronic band assembly of claim 1, wherein the telemetry interface of the elongate band is configured to transmit trending data for a time period based on the relative or absolute blood pressure, wherein the time period comprises one or more days, weeks, months, or years.

\* \* \* \* \*